(12) United States Patent
Lee et al.

(10) Patent No.: US 6,190,882 B1
(45) Date of Patent: Feb. 20, 2001

(54) MAMMALIAN CIRCADIAN RHYTHM-LIKE GENE

(75) Inventors: Cheng-Chi Lee; Urs Albrecht; Gregor Eichele; Zhong Sheng Sun, all of Houston, TX (US)

(73) Assignee: Research Development Foundation, Carson City, NV (US)

( * ) Notice: Under 35 U.S.C. 154(b), the term of this patent shall be extended for 0 days.

(21) Appl. No.: 09/150,460

(22) Filed: Sep. 9, 1998

Related U.S. Application Data

(60) Provisional application No. 60/065,957, filed on Nov. 4, 1997, and provisional application No. 60/058,256, filed on Sep. 9, 1997.

(51) Int. Cl.[7] ...................................................... C12P 21/06

(52) U.S. Cl. ..................... 435/69.1; 435/320.1; 435/325; 435/252.3; 435/348; 435/6; 536/23.1; 530/350

(58) Field of Search ........................... 435/6, 69.1, 320.1, 435/325, 257.3, 348; 536/23.1; 530/350

(56) References Cited

PUBLICATIONS

Tei, AB002107 Mar., 1997.*
Tei, AB002108 Mar., 1997.*
Citri et al., Nature 326:42–47 Mar., 1987.*

* cited by examiner

*Primary Examiner*—Karen Cochrane Carlson
(74) *Attorney, Agent, or Firm*—Benjamin Aaron Adler

(57) ABSTRACT

The present invention provides DNA encoding a RIGUI protein selected from the group consisting of: (a) isolated DNA which encodes a RIGUI protein; (b) isolated DNA which hybridizes to isolated DNA of (a) above and which encodes a RIGUI protein; and (c) isolated DNA differing from the isolated DNAs of (a) and (b) above in codon sequence due to the degeneracy of the genetic code, and which encodes a RIGUI protein. Also provided is a vector capable of expressing the DNA adapted for expression in a recombinant cell and regulatory elements necessary for expression of the DNA in the cell. Further, a host cell transfected with the vector disclosed herein the vector expressing a RIGUI protein.

18 Claims, 11 Drawing Sheets

(8 of 11 Drawing Sheet(s) Filed in Color)

FIG. 2-2

```
              Basic Region    Helix 1        Loop           Helix 2

Consensus    .KE.■R..■.R.RR.K.N...■■A..■■.P.....DK...■RL..S.L

NPAS2        AKRA■RNKSEKKRRDQFNVLIK■SSM■G---NTRKMDKPT-V■EKVIGFL
Clock        AKRV■RNKSEKKRRDQFNVLIK■GSM■G---NARKMDKST-V■QKSIDFL
DRO.TRH      RKEK■RD-■ARSRRGKENFEFY■AKM■LPAAITSQLDKASIIRLLTISYL
MOUSE.SIM1   MKEK■KN-■ARTRREKENSEFY■AKL■LPSAITSQLDKAASIIRLTTSYL
HUMAN.HIFa   RKEK■RD-■ARSRRSKESEVFY■AHQ■LPHNVSSHLDKAS-VMRLTISYL
MOUSE.EPAS   RKEK■RD-■ARCRRSKETEVFY■AHE■LPHSVSSHLDKAS-IMRLAISFL
MOUSE.AHR    AEGIKSNPSKRHRDRLNTELDR■ASL■FPQDVINKLDKLS-V■RLSVSYL
HUMAN.ARNT   ARENHSEIERRRRNKMTAYIT■SDMV■TCSALARKPDKL/T-I■RMAVSHM
RIGUI        SGCS■EQS■RARTQKELMTALR■KLR■PER-RGKGRSGTLAT■QYALACV
```

FIG. 3

SEQUENCE LISTING

<160> NUMBER OF SEQ ID NOS: 21

<210> SEQ ID NO 1
<211> LENGTH: 20
<212> TYPE: DNA
<213> ORGANISM: artificial sequence
<220> FEATURE:
<223> OTHER INFORMATION: Primer used for the STS-PCR mapping of RIGUI

<400> SEQUENCE: 1
ctcccatctg gggaggaggt                                                    20

<210> SEQ ID NO 2
<211> LENGTH: 20
<212> TYPE: DNA
<213> ORGANISM: artificial sequence
<220> FEATURE:
<223> OTHER INFORMATION: Primer used for the STS-PCR mapping of RIGUI

<400> SEQUENCE: 2
ggaccatctc caggagtcca                                                    20

<210> SEQ ID NO 3
<211> LENGTH: 6614
<212> TYPE: DNA
<213> ORGANISM: artificial sequence
<220> FEATURE:
<223> OTHER INFORMATION: Nucleotide sequence of 6.6 kb cDNA of human
      RIGUI

<400> SEQUENCE: 3
ggctggagcg gcggcgggca ggcgtgcgga ggacactcct gcgaccaggt actggctgtg        60
atcgaacttc tcaaccctca gagacttaga tcttccacct cactccctca gccaagcctc       120 caggcccct cgtgcatccg tggtggcctc tctgccttct ctgttctgtt ctccccatgg        180
cccagacatg agtggccccc tagaaggggc tgatggggga ggggaccccca ggcctgggga     240 atcattttgt cctggggcg tcccatcccc tgggccccca cagcaccggc cttgcccagg       300
ccccagcctg gccgatgaca ccgatgccaa cagcaatggt tcaagtgcca atgagtccaa      360
cgggcatgag tctagaggcg catctcagcg gagctcacac agctcctcct caggcaacgg     420
caaggactca gccctgctgg agaccactga gagcagcaag agcacaaact ctcagagccc     480
atccccaccc agcagttcca ttgcctacag cctcctgagt gccagctcag agcaggacaa     540
cccgtccacc agtggctgca gcagtgaaca gtcagcccgg gcaaggactc agaaggaact     600
catgacagca cttcgagagc tcaagcttcg actgccgcca gagcgccggg gcaagggccg     660
ctctgggacc ctggccacgc tgcagtacgc actggcctgt gtcaagcagg tgcaggccaa    720
ccaggaatac taccagcagt ggagcctgga ggagggcgag ccttgctcca tggacatgtc     780
cacctatacc ctggaggagc tggagcacat cacgtctgag tacacacttc agaaccagga     840
taccttctca gtggctgtct ccttcctgac gggccgaatc gtctacattt cggagcaggc       900
agccgtcctg ctgcgttgca agcgggacgt gttccgggt accgcttct ctgagctcct       960 ggctccccag gatgtgggag tcttctatgg ttccactgct ccatctcgcc tgcccacctg    1020
gggcacaggg gcctcagcag gttcaggcct cagggacttt acccaggaga gtccgtctt     1080 ctgccgtatc agaggaggtc ctgaccggga tccaggggcct cggtaccagc cattccgcct   1140
aaccccgtat gtgaccaaga tccgggtctc agatgggccc cctgcacagc cgtgctgcct   1200

-continued

```
gctgattgca gagcgcatcc attcgggtta cgaagctccc cggataccccc ctgacaagag   1260
gattttcact acgcggcaca cacccagctg cctcttccag gatgtggatg aaagggctgc   1320
cccctgctg ggctacctgc cccaggacct cctgggggcc ccagtgctcc tgttcctgca    1380
tcctgaggac cgacccctca tgctggctat ccacaagaag attctgcagt tggcgggcca   1440
gccctttgac cactcccta tccgcttctg tgcccgcaac ggggagtatg tcaccatgga    1500
caccagctgg gctggctttg tgcacccctg gagccgcaag gtagccttcg tgttgggccg   1560
ccacaaagta cgcacggccc ccctgaatga ggacgtgttc actcccccgg ccccccagccc  1620
agctccctcc ctggacactg atatccagga gctgtcagag cagatccacc ggctgctgct   1680
gcagcccgtc cacagcccca gccccacggg actctgtgga gtcggcgccg tgacatcccc   1740
aggccctctc cacagccctg ggtcctccag tgatagcaac ggggtgatg cagaggggcc    1800
tgggcctcct cgccagtga ctttccaaca gatctgtaag gatgtgcatc tggtgaagca    1860
ccagggccag cagctttta ttgagtctcg ggcccggcct cagtcccggc ccgcctccc    1920
tgctacaggc acgttcaagg ccaaggccct tccctgccaa tccccagacc cagagctgga   1980
ggcgggttct gctcccgtcc aggccccact agccttggtc cctgaggagg ccgagaggaa   2040
agaagcctcc agctgctcct accagcagat caactgcctg acagcatcc tcaggtacct    2100
ggagagctgc aacctcccca gcaccactaa gcgtaaatgt gcctcctcct cctcctatac   2160
cacctcctca gcctctgacg acgacaggca gaggacaggt ccagtctctg tggggaccaa   2220
gaaagatccg ccgtcagcag cgctgtctgg ggaggggggcc accccacgga aggagccagt   2280
ggtgggaggc accctgagcc cgctcgcccct ggccaataag gcggagagtg tggtgtccgt   2340
caccagtcag tgtagcttca gctccaccat cgtccatgtg ggagacaaga gcccccggga   2400
gtcagacatc atcatgatgg aggacctgcc tggcctagcc ccaggcccag ccccagccc    2460
agccccagc cccacagtag cccctgaccc agccccagac gcctaccgtc cagtggggct    2520
gaccaaggcc gtgctgtccc tgcacacaca gaaggaagag caagccttcc tcagccgctt   2580
ccgagacctg gcaggctgc gtggactcga cagctcttcc acagtccct cagcccttgg    2640
cgagcgaggt agccacctgg ggcctcctgg agcctgccct ctgcccagtc taggactgga   2700
ttgttggggg gtgggtctta agggaggtgt ttctgctcca gggacccagg ctggtgttgc   2760
ttccaccact aggccctgcc tagggacagg cccctcgcta gcttctcccc actaggatgg   2820
ggttccgggc tgcagccaga ggagggcagc ctgggggat ggcactggga tgggcaggca    2880
gaggtgctgt ctccaggtaa gcgacttcag gcctagcctg ggggcagggg caggaagtat   2940
gcccacttag gagtcagttg tcactgatga agagacatgc atagattctg gccaactct    3000
gggtggggtc tgggcttcaa gggcaggtgg aaggcagccc ctccaggtgc ctgagggaga   3060
tcccctgcag gcagacgcag gactcaggac tgggctttcc agccccactc tttactccat   3120
tgcaagctag gcagaatacg gcctcgatgg gcaggaggaa tgcctaggct ggcagtgccc   3180
acaggagttt ggcggaccag agccatctgt ccatgtgtcc atggactcac cctgcttcct   3240
ccatctgcca gcatgcctcc atcttccgca cacccccagc tcgaccctc gtgtaacctc    3300
tccctggcct tgttcctttc tcaataaatc cccttgtccc tggctcctgt gattcttccc   3360
tgaaggtgcc ccacctcctg agtcccccgt tctgtgtggg ttgagaagct ctctctggga   3420
ccttggcctg tcctctccct ggtcagcgtg tcagggcagt gtgggtagca ggggtactaa   3480
ccccaggttg aggtccttgc taaccctagt ctctccccac aggctgccac cacggccccg   3540
cacccccaag ccgccgacac cactgccgat ccaaagccaa gcgctcacgc caccaccaga   3600
```

-continued

```
accctcgggc tgaagcgccc tgctatgtct cacacccctc acccgtgcca ccctccaccc    3660
cctggcccac cccaccagcc actaccccct tcccagcggt tgtccagccc taccctctcc    3720
cagtgttctc tcctcgagga ggcccccagc ctcttccccc tgctcccaca tctgtgcccc    3780
cagctgcttt cccgcccct ttggtgaccc caatggtggc cttggtgctc cctaactatc    3840
tgttcccaac cccatccagc tatccttatg gggcactcca gaccctgct gaagggcctc    3900 ccactcctgc ctcgcactcc ccttctccat ccttgcccgc cctcccccg agtcctcctc    3960 accgcccgga ctctccactg ttcaactcga gatgcagctc tccactccag ctcaatctgc    4020
tgcagctgga ggagctcccc cgtgctgagg gggctgctgt tgcaggaggc cctgggagca    4080
gtgccgggcc cccacctccc agtgcggagg ctgctgagcc agaggccaga ctgtgagcac    4140
tgacccctgc gtctgcctgc cagccccac cccagccccg ccctctgcc accctgtgct    4200 gcctgctgtc tctgccaggc tggcgtctca gcctccagga ggtggaggga gtccccagct    4260
gaatttctga atgaggcaga aattggctac ctcctctttg aagggacagt cctgtctgtc    4320
tgacaggtgg tgaggacatc tcaataactt ctgagagac atctgtcact tggaaagggt    4380
ctggcctcac atccccactc ttcgccagct ttcttctctc tcagcctggc cctactgtca    4440
cgaagtgggg agcagagacc actggggttg gatgtgcctc tccccacaac cagtaagagc    4500
agttgaaggg aggcctaggt gctgacccct ccatccctcc ttgccccct cccctcctcc    4560 aggcggaggt cactgagtcc tccaatcagg acgcactttc cggctccagt gacctgctcg    4620
aacttctgct gcaagaggac tcgcgctccg gcacaggctc cgcagcctcg ggctccttgg    4680
gctctggctt gggctctggg tctggttcag gctcccatga aggggcagc acctcagcca    4740 gcatcactcg tgagtacccc gcctccagca tctcccaggg tagggcagtg attggggagc    4800
cgggagccca ggccccgtct tggcggagct tcctaaggcc actgggatgg acatgtggcc    4860
tttgagggag gccttgtgag gtcccaggag tgggcatgca gccggcctga ctcccattgg    4920 tctgccccc acttcacagg cagcagccag agcagccaca caagcaaata ctttggcagc    4980
atcgactctt ccgaggctga ggctggggct gctcggggcg gggctgagcc tggggaccag    5040
gtgattaagt acgtgctcca ggatcccatt tggctgctca tggccaatgc tgaccagcgc    5100
gtcatgatga cctaccaggt gccctccagg gacatgacct ctgtgctgaa gcaggatcgg    5160
gagcggctcc gagccatgca gaagcagcag cctcggtttt ctgaggacca gcggcgggaa    5220
ctgggtgctg tgcactcctg ggtccggaag ggccaactgc ctcgggctct tgatgtgatg    5280
gtgagagaag cctgggacgg ggagaaaaaa gaattgagct caagttcaag ggggagaaaa    5340
aagaattgag ctcaagttca aggggagaa aaagaattg agctcaagtt caagggatcg    5400
aggccaagag ctgatctcct tgatgtcctt ggatcattaa ttctgaagaa tgttgattcc    5460
actaaatttg ctgtggatta tagaatatta agccgcgtga gtctttgcag aacttttcac    5520
agcctatcct atgctaatat gcattgtgac tgtcctgtaa cggcatctgg gtagagggca    5580
caaggcactg tccaaccttg ttggaccgca ggtgcatctg tgtggactgg tgcttcttgg    5640
gagtacattt cgggaagcac agtgggctgg gggtgggaag ctgcgctggc aggttagcag    5700
tgagaaccct gtctgactct ctcatgtcca tttctctcac caaggcctgt gtggactgtg    5760
ggagcagcac ccaagatcct ggtcaccctg atgacccact cttctcagag ctggatggac    5820
tggggctgga gccatggaa gagggtggag gcgagcaggg cagcagcggt ggcggcagtg    5880
gtgagggaga gggctgcgag gaggcccaag gcggggccaa ggcttcaagc tctcaggact    5940
```

-continued

| | |
|---|---|
| tggctatgga ggaggaggaa gaagcaggag ctcatccagt ccagccttac ctacagcagg | 6000 |
| aaactgcacc agctagactc cattctggga ccatctccag gagtccatga gaggctttct | 6060 |
| tctcctatgt cccaattctc agaactcaga tgtggctaga ccaaccagtg ggaaactgcc | 6120 |
| ccagcttctc ccaccatagg gggccggacc cccatcacca gcctaggatc cagggggctgc | 6180 |
| ctctggcctc ttagggagca gagagcagaa ctccgcagcc cagcccagag gagtgtcacc | 6240 |
| tcccaccttt ggagaggaat ccttccctcc cctggacaaa gttgctgaca agctgctgaa | 6300 |
| gtggcctctc catattccag ctgagcctga atctgactct tgagggttgg ggctgcactt | 6360 |
| atttattgcg gggagacagc tctctctccc acctcctccc cagatgggag gagagcctga | 6420 |
| ggcccaagca ggacccgggg gttccagccc ctagctgctc tggagtgggg gaggttggtg | 6480 |
| gaccatggag tccctggtgc tgcccctcag gtgggaccca ggggttctca gctgtaccct | 6540 |
| ctgccgatgg catttgtgtt tttgatattt gtgtctgtta ctacttttt aatacaaaaa | 6600 |
| gataaaaacg ccaa | 6614 |

<210> SEQ ID NO 4
<211> LENGTH: 4656
<212> TYPE: DNA
<213> ORGANISM: artificial sequence
<220> FEATURE:
<223> OTHER INFORMATION: Nucleotide sequence of 4.7 kb cDNA of human RIGUI

<400> SEQUENCE: 4

| | |
|---|---|
| ggctggagcg gcggcgggca ggcgtgcgga ggacactcct gcgaccaggt actggctgtg | 60 |
| atcgaacttc tcaaccctca gagacttaga tcttccacct cactccctca gccaagcctc | 120 |
| caggcccct cgtgcatccg tggtggcctc tctgccttct ctgttctgtt ctccccatgg | 180 |
| cccagacatg agtggccccc tagaagggc tgatggggga ggggacccca ggcctgggga | 240 |
| atcattttgt cctggggcg tcccatcccc tgggcccccca cagcaccggc cttgcccagg | 300 |
| ccccagcctg gccgatgaca ccgatgccaa cagcaatggt tcaagtggca atgagtccaa | 360 |
| cgggcatgag tctagaggcg catctcagcg gagctcacac agctcctcct caggcaacgg | 420 |
| caaggactca gccctgctgg agaccactga gagcagcaag agcacaaact tcagagcccc | 480 |
| atccccaccc agcagttcca ttgcctacag cctcctgagt gccagctcag agcaggacaa | 540 |
| cccgtccacc agtggctgca gcagtgaaca gtcagcccgg gcaaggactc agaaggaact | 600 |
| catgacagca cttcgagagc tcaagcttcg actgccgcca gagcgccggg gcaagggccg | 660 |
| ctctggggacc ctggccacgc tgcagtacgc actggcctgt gtcaagcagg tgcaggccaa | 720 |
| ccaggaatac taccagcagt ggagcctgga ggagggcgag ccttgctcca tggacatgtc | 780 |
| cacctatacc ctggaggagc tggagcacat cacgtctgag tacacacttc agaaccagga | 840 |
| taccttctca gtggctgtct ccttcctgac gggccgaatc gtctacattt cggagcaggc | 900 |
| agccgtcctg ctgcgttgca gcgggacgt gttccggggt accgcttct ctgagctcct | 960 |
| ggctccccag gatgtgggag tcttctatgg ttccactgct ccatctcgcc tgcccacctg | 1020 |
| ggcacaggg gcctcagcag gttcaggcct cagggacttt acccaggaga agtccgtctt | 1080 |
| ctgccgtatc agaggaggtc ctgaccggga tccaggggcct cggtaccagc cattccgcct | 1140 |
| aaccccgtat gtgaccaaga tccgggtctc agatggggcc cctgcacagc cgtgctgcct | 1200 |
| gctgattgca gagcgcatcc attcggggtta cgaagctccc cggataccccc ctgacaagag | 1260 |
| gatttttcact acgcggcaca cacccagctg cctcttccag gatgtggatg aagggctgc | 1320 |

-continued

```
cccctgctg ggctacctgc cccaggacct cctgggggcc ccagtgctcc tgttcctgca    1380
tcctgaggac cgacccctca tgctggctat ccacaagaag attctgcagt tggcgggcca    1440 gcccttgac cactccccta tccgcttctg tgcccgcaac ggggagtatg tcaccatgga    1500
caccagctgg gctggctttg tgcacccctg gagccgcaag gtagccttcg tgttgggccg    1560
ccacaaagta cgcacggccc ccctgaatga ggacgtgttc actcccccgg ccccccagccc   1620 agctccctcc ctggacactg atatccagga gctgtcagag cagatccacc ggctgctgct    1680
gcagcccgtc cacagcccca gccccacggg actctgtgga gtcggcgccg tgacatcccc    1740
aggccctctc cacagccctg gtcctccag tgatagcaac gggggtgatg cagaggggcc     1800
tgggcctcct cgccagtga ctttccaaca gatctgtaag gatgtgcatc tggtgaagca     1860
ccagggccag cagcttttta ttgagtctcg ggcccggcct cagtcccggc ccgcctccc     1920 tgctacaggc acgttcaagg ccaaggccct tccctgccaa tccccagacc cagagctgga    1980
ggcgggttct gctcccgtcc aggccccact agccttggtc cctgaggagg ccgagaggaa    2040
agaagcctcc agctgctcct accagcagat caactgcctg gacagcatcc tcaggtacct    2100
ggagagctgc aacctcccca gcaccactaa gcgtaaatgt gcctcctcct cctcctatac    2160
cacctcctca gcctctgacg acgacaggca gaggacaggt ccagtctctg tggggaccaa    2220
gaaagatccg ccgtcagcag cgctgtctgg ggagggggcc accccacgga aggagccagt    2280
ggtgggaggc accctgagcc cgtccgcccc ggccaataag gcggagagtg tggtgtccgt    2340
caccagtcag tgtagcttca gctccaccat cgtccatgtg ggagacaaga agcccccgga    2400
gtcggacatc atcatgatgg aggacctgcc tggtctagcc ccaggcccag ccccagccc    2460 agccccagc cccacagtag cccctgaccc agccccagac gcctaccgtc cagtggggct     2520
gaccaaggcc gtgctgtccc tgcacacgca aaggaagag caagccttcc tcagccgctt     2580
ccgagacctg gcaggctgc gtggactcga cagctcttcc acagctccct cagcccttgg     2640
cgagcgaggc tgccaccacg gccccgcacc cccaagccgc cgacaccact gccgatccaa    2700
agccaagcgc tcacgccacc accagaaccc tcgggctgaa cgccctgct atgtctcaca    2760 ccctcaccc gtgccaccct caccccctg gcccaccca ccagccacta ccccttccc       2820 agcggttgtc cagcctacc ctctcccagt gttctctcct cgaggaggcc cccagcctct    2880
tccccctgct cccacatctg tgccccagc tgctttcccc gcccctttgg tgaccccaat    2940
ggtggccttg gtgctcccta actatctgtt cccaacccca tccagctatc cttatggggc    3000
actccagacc cctgctgaag ggcctccac tcctgcctcg cactcccctt ctccatcctt    3060
gcccgccctc ccccgagtc ctcctcaccg cccggactct ccactgttca actcgagatg    3120
cagctctcca ctccagctca atctgctgca gctggaggag ctccccgtg ctgaggggc    3180 tgctgttgca ggaggcccctg ggagcagtgc cgggcccca cctcccagtg cggaggctgc    3240
tgagccagag gccagactgg cggaggtcac tgagtcctcc aatcaggacg cactttccgg    3300
ctccagtgac ctgctcgaac ttctgctgca agaggactcg cgctccggca caggctccgc    3360
agcctcgggc tccttgggct ctggcttggg ctctgggtct ggttcaggct cccatgaagg    3420
gggcagcacc tcagccagca tcactcgcag cagccagagc agccacacaa gcaaatactt    3480
tggcagcatc gactcttccg aggctgaggc tgggctgct cggggcgggg ctgagcctgg    3540
ggaccaggtg attaagtacg tgctccagga tcccatttgg ctgctcatgg ccaatgctga    3600
ccagcgcgtc atgatgacct accaggtgcc ctccaggac atgacctctg tgctgaagca    3660
ggatcgggag cggctccgag ccatgcagaa gcagcagcct cggttttctg aggaccagcg    3720
```

```
gcgggaactg ggtgctgtgc actcctgggt ccggaagggc caactgcctc gggctcttga      3780
tgtgatggcc tgtgtggact gtgggagcag cacccaagat cctggtcacc ctgatgaccc      3840
actcttctca gagctggatg gactgggggct ggagcccatg aagagggtg gaggcgagca      3900
```

*Note: line 3900 shows "gactgggct" (corrected below)*

```
gcgggaactg ggtgctgtgc actcctgggt ccggaagggc caactgcctc gggctcttga      3780
tgtgatggcc tgtgtggact gtgggagcag cacccaagat cctggtcacc ctgatgaccc      3840
actcttctca gagctggatg gactgggggct ggagcccatg aagagggtg gaggcgagca      3900 gggcagcagc ggtggcggca gtggtgaggg agagggctgc gaggaggccc aaggcggggc      3960
caaggcttca agctctcagg acttggctat ggaggaggag aagaaggca ggagctcatc      4020 cagtccagcc ttacctacag caggaaactg caccagctag actccattct gggaccatct      4080
ccaggagtcc atgagaggct ttcttctcct atgtcccaat tctcagaact cagatgtggc      4140
tagaccaacc agtgggaaac tgccccagct tctcccacca taggggggcg accccccatc      4200
accagcctag gatccagggg ctgcctctgg cctcttaggg agcagagagc agaactccgc      4260
agcccagccc agaggagtgt cacctcccac ctttggagag gaatccttcc ctcccctgga      4320
caaagttgct gacaagctgc tgaagtggcc tctccatatt ccagctgagc ctgaatctga      4380
ctcttgaggg ttggggctgc acttatttat tgcggggaga cagctctctc tcccacctcc      4440
tccccagatg ggaggagagc ctgaggccca agcaggaccc gggggttcca gccctagct       4500 gctctggagt gggggaggtt ggtggaccat ggagtccctg gtgctgcccc tcaggtggga      4560 cccagggggtt ctcagctgta ccctctgccg atggcatttg tgtttttgat atttgtgtct     4620
gttactactt ttttaataca aaagataaa  aacgcc                                4656
```

<210> SEQ ID NO 5
<211> LENGTH: 3057
<212> TYPE: DNA
<213> ORGANISM: artificial sequence
<220> FEATURE:
<223> OTHER INFORMATION: Nucleotide sequence of 3.0 kb cDNA of human RIGUI

<400> SEQUENCE: 5

```
ggctggagcg gcggcgggca ggcgtgcgga ggacactcct gcgaccaggt actggctgtg        60
atcgaacttc tcaaccctca gagacttaga tcttccacct cactccctca gccaagcctc       120 caggcccct cgtgcatccg tggtggcctc tctgccttct ctgttctgtt ctccccatgg        180
cccagacatg agtggccccc tagaaggggc tgatggggga gggacccca ggcctgggga        240 atcattttgt cctgggggcg tcccatcccc tgggccccca cagcaccggc cttgcccagg       300
ccccagcctg gccgatgaca ccgatgccaa cagcaatggt tcaagtggca atgagtccaa       360
cgggcatgag tctagaggcg catctcagcg gagctcacac agctcctcct caggcaacgg       420
caaggactca gccctgctgg agaccactga gagcagcaag agcacaaact ctcagagccc       480
atccccaccc agcagttcca ttgcctacag cctcctgagt gccagctcag agcaggacaa       540
cccgtccacc agtggctgca gcagtgaaca gtcagcccgg caaggactc agaaggaact        600 catgacagca cttcgagagc tcaagcttcg actgccgcca gagcgccggg gcaagggccg       660
ctctgggacc ctggccacgc tgcagtacgc actggcctgt gtcaagcagg tgcaggccaa       720
ccaggaatac taccagcagt ggagcctgga ggagggcgag ccttgctcca tggacatgtc       780
cacctatacc ctgaggagc tggagcacat cacgtctgag tacacacttc agaaccagga       840
taccttctca gtggctgtct ccttcctgac gggccgaatc gtctacattt cggagcaggc       900
agccgtcctg ctgcgttgca gcgggacgt gttccgggt accgcttct ctgagctcct        960 ggctccccag gatgtgggag tcttctatgg ttccactgct ccatctcgcc tgcccacctg      1020
```

-continued

| | |
|---|---|
| gggcacaggg gcctcagcag gttcaggcct cagggacttt acccaggaga agtccgtctt | 1080 |
| ctgccgtatc agaggaggtc ctgaccggga tccagggcct cggtaccagc cattccgcct | 1140 |
| aaccccgtat gtgaccaaga tccgggtctc agatggggcc cctgcacagc cgtgctgcct | 1200 |
| gctgattgca gagcgcatcc attcgggtta cgaagctccc cggatacccc ctgacaagag | 1260 |
| gattttcact acgcggcaca cacccagctg cctcttccag gatgtggatg aaagggctgc | 1320 |
| cccctgctg gctacctgc ccaggacct cctgggggcc ccagtgctcc tgttcctgca | 1380 |
| tcctgaggac cgacccctca tgctggctat ccacaagaag attctgcagt ggcgggcca | 1440 |
| gccctttgac cactcccta tccgcttctg tgcccgcaac ggggagtatg tcaccatgga | 1500 |
| caccagctgg gctggctttg tgcacccctg agccgcaag gtagccttcg tgttgggccg | 1560 |
| ccacaaagta cgcacggccc cctgaatga ggacgtgttc actccccgg ccccagccc | 1620 |
| agctccctcc ctggacactg atatccagga gctgtcagag cagatccacc ggctgctgct | 1680 |
| gcagcccgtc cacagcccca gccccacggg actctgtgga gtcggcgccg tgacatcccc | 1740 |
| aggccctctc cacagccctg gtcctccag tgatagcaac ggggtgatg cagaggggcc | 1800 |
| tgggcctcct gcgccagtga ctttccaaca gatctgtaag gatgtgcatc tggtgaagca | 1860 |
| ccagggccag cagcttttta ttgagtctcg ggcccggcct cagtcccggc cccgcctccc | 1920 |
| tgctacaggc acgttcaagg ccaaggccct tccctgccaa tccccagacc cagagctgga | 1980 |
| ggcgggttct gctcccgtcc aggcccact agccttggtc cctgaggagg ccgagaggaa | 2040 |
| agaagcctcc agctgctcct accagcagat caactgcctg acagcatcc tcaggtacct | 2100 |
| ggagagctgc aacctcccca gcaccactaa gcgtaaatgt gcctcctcct cctcctatac | 2160 |
| cacctcctca gcctctgacg acgacaggca gaggacaggg ccagtctctg tggggaccaa | 2220 |
| gaaagatccg ccgtcagcag cgctgtctgg ggagggggcc accccacgga aggagccagt | 2280 |
| ggtgggaggc accctgagcc cgctcgccct ggccaataag gcgagagtg tggtgtccgt | 2340 |
| caccagtcag tgtagcttca gctccaccat cgtccatgtg ggagacaaga gcccccgga | 2400 |
| gtcggacatc atcatgatgg aggacctgcc tggtctagcc ccaggcccag ccccagccc | 2460 |
| gactccattc tgggaccatc tccaggagtc catgagaggc tttcttctcc tatgtcccaa | 2520 |
| ttctcagaac tcagatgtgg ctagaccaac cagtgggaaa ctgccccagc ttctcccacc | 2580 |
| atagggggcc ggaccccat caccagccta ggatccaggg gctgcctctg gcctcttagg | 2640 |
| gagcagagag cagaactccg cagcccagcc cagaggagtg tcacctccca cctttggaga | 2700 |
| ggaatccttc cctcccctgg acaaagttgc tgacaagctg ctgaagtggc ctctccatat | 2760 |
| tccagctgag cctgaatctg actcttgagg gttggggctg cacttattta ttgcggggag | 2820 |
| acagctctct ctcccacctc ctccccagat gggaggagag cctgaggccc aagcaggacc | 2880 |
| cgggggttcc agccctagc tgctctggag tggggaggt tggtggacca tggagtccct | 2940 |
| ggtgctgccc ctcaggtggg acccagggt tctcagctgt accctctgcc gatggcattt | 3000 |
| gtgttttga tatttgtgtc tgttactact tttttaatac aaaaagataa aaacgcc | 3057 |

<210> SEQ ID NO 6
<211> LENGTH: 1290
<212> TYPE: PRT
<213> ORGANISM: Homo sapiens
<220> FEATURE:
<223> OTHER INFORMATION: Protein sequence corresponding to RIGUI 4.7;
      Gene Bank
      Accession Number: AF022991

<400> SEQUENCE: 6

-continued

```
Met Ser Gly Pro Leu Glu Gly Ala Asp Gly Gly Asp Pro Arg
              5                  10                 15

Pro Gly Glu Ser Phe Cys Pro Gly Val Pro Ser Pro Gly Pro
             20                  25                 30

Pro Gln His Arg Pro Cys Pro Gly Pro Ser Leu Ala Asp Asp Thr
             35                  40                 45

Asp Ala Asn Ser Asn Gly Ser Ser Gly Asn Glu Ser Asn Gly His
             50                  55                 60

Glu Ser Arg Gly Ala Ser Gln Arg Ser Ser His Ser Ser Ser Ser
             65                  70                 75

Gly Asn Gly Lys Asp Ser Ala Leu Leu Glu Thr Thr Glu Ser Ser
             80                  85                 90

Lys Ser Thr Asn Ser Gln Ser Pro Ser Pro Pro Ser Ser Ile
             95                 100                105

Ala Tyr Ser Leu Leu Ser Ala Ser Ser Glu Gln Asp Asn Pro Ser
            110                 115                120

Thr Ser Gly Cys Ser Ser Glu Gln Ser Ala Arg Ala Arg Thr Gln
            125                 130                135

Lys Glu Leu Met Thr Ala Leu Arg Glu Leu Lys Leu Arg Leu Pro
            140                 145                150

Pro Glu Arg Arg Gly Lys Gly Arg Ser Gly Thr Leu Ala Thr Leu
            155                 160                165

Gln Tyr Ala Leu Ala Cys Val Lys Gln Val Gln Ala Asn Gln Glu
            170                 175                180

Tyr Tyr Gln Gln Trp Ser Leu Glu Glu Gly Glu Pro Cys Ser Met
            185                 190                195

Asp Met Ser Thr Tyr Thr Leu Glu Glu Leu Glu His Ile Thr Ser
            200                 205                210

Glu Tyr Thr Leu Gln Asn Gln Asp Thr Phe Ser Val Ala Val Ser
            215                 220                225

Phe Leu Thr Gly Arg Ile Val Tyr Ile Ser Glu Gln Ala Ala Val
            230                 235                240

Leu Leu Arg Cys Lys Arg Asp Val Phe Arg Gly Thr Arg Phe Ser
            245                 250                255

Glu Leu Leu Ala Pro Gln Asp Val Gly Val Phe Tyr Gly Ser Thr
            260                 265                270

Ala Pro Ser Arg Leu Pro Thr Trp Gly Thr Gly Ala Ser Ala Gly
            275                 280                285

Ser Gly Leu Arg Asp Phe Thr Gln Glu Lys Ser Val Phe Cys Arg
            290                 295                300

Ile Arg Gly Gly Pro Asp Arg Asp Pro Gly Pro Arg Tyr Gln Pro
            305                 310                315

Phe Arg Leu Thr Pro Tyr Val Thr Lys Ile Arg Val Ser Asp Gly
            320                 325                330

Ala Pro Ala Gln Pro Cys Cys Leu Leu Ile Ala Glu Arg Ile His
            335                 340                345

Ser Gly Tyr Glu Ala Pro Arg Ile Pro Pro Asp Lys Arg Ile Phe
            350                 355                360

Thr Thr Arg His Thr Pro Ser Cys Leu Phe Gln Asp Val Asp Glu
            365                 370                375

Arg Ala Ala Pro Leu Leu Gly Tyr Leu Pro Gln Asp Leu Leu Gly
            380                 385                390
```

-continued

```
Ala Pro Val Leu Leu Phe Leu His Pro Glu Asp Arg Pro Leu Met
            395                 400                 405

Leu Ala Ile His Lys Lys Ile Leu Gln Leu Ala Gly Gln Pro Phe
            410                 415                 420

Asp His Ser Pro Ile Arg Phe Cys Ala Arg Asn Gly Glu Tyr Val
            425                 430                 435

Thr Met Asp Thr Ser Trp Ala Gly Phe Val His Pro Trp Ser Arg
            440                 445                 450

Lys Val Ala Phe Val Leu Gly Arg His Lys Val Arg Thr Ala Pro
            455                 460                 465

Leu Asn Glu Asp Val Phe Thr Pro Pro Ala Pro Ser Pro Ala Pro
            470                 475                 480

Ser Leu Asp Thr Asp Ile Gln Glu Leu Ser Glu Gln Ile His Arg
            485                 490                 495

Leu Leu Leu Gln Pro Val His Ser Pro Ser Pro Thr Gly Leu Cys
            500                 505                 510

Gly Val Gly Ala Val Thr Ser Pro Gly Pro Leu His Ser Pro Gly
            515                 520                 525

Ser Ser Ser Asp Ser Asn Gly Gly Asp Ala Glu Gly Pro Gly Pro
            530                 535                 540

Pro Ala Pro Val Thr Phe Gln Gln Ile Cys Lys Asp Val His Leu
            545                 550                 555

Val Lys His Gln Gly Gln Gln Leu Phe Ile Glu Ser Arg Ala Arg
            560                 565                 570

Pro Gln Ser Arg Pro Arg Leu Pro Ala Thr Gly Thr Phe Lys Ala
            575                 580                 585

Lys Ala Leu Pro Cys Gln Ser Pro Asp Pro Glu Leu Glu Ala Gly
            590                 595                 600

Ser Ala Pro Val Gln Ala Pro Leu Ala Leu Val Pro Glu Glu Ala
            605                 610                 615

Glu Arg Lys Glu Ala Ser Ser Cys Ser Tyr Gln Gln Ile Asn Cys
            620                 625                 630

Leu Asp Ser Ile Leu Arg Tyr Leu Glu Ser Cys Asn Leu Pro Ser
            635                 640                 645

Thr Thr Lys Arg Lys Cys Ala Ser Ser Ser Tyr Thr Thr Ser
            650                 655                 660

Ser Ala Ser Asp Asp Arg Gln Arg Thr Gly Pro Val Ser Val
            665                 670                 675

Gly Thr Lys Lys Asp Pro Pro Ser Ala Ala Leu Ser Gly Glu Gly
            680                 685                 690

Ala Thr Pro Arg Lys Glu Pro Val Val Gly Gly Thr Leu Ser Pro
            695                 700                 705

Leu Ala Leu Ala Asn Lys Ala Glu Ser Val Val Ser Val Thr Ser
            710                 715                 720

Gln Cys Ser Phe Ser Ser Thr Ile Val His Val Gly Asp Lys Lys
            725                 730                 735

Pro Pro Glu Ser Asp Ile Ile Met Met Glu Asp Leu Pro Gly Leu
            740                 745                 750

Ala Pro Gly Pro Ala Pro Ser Pro Ala Pro Ser Pro Thr Val Ala
            755                 760                 765

Pro Asp Pro Ala Pro Asp Ala Tyr Arg Pro Val Gly Leu Thr Lys
            770                 775                 780

Ala Val Leu Ser Leu His Thr Gln Lys Glu Glu Gln Ala Phe Leu
```

```
                785                 790                 795
Ser Arg Phe Arg Asp Leu Gly Arg Leu Arg Gly Leu Asp Ser Ser
                800                 805                 810
Ser Thr Ala Pro Ser Ala Leu Gly Glu Arg Gly Cys His His Gly
                815                 820                 825
Pro Ala Pro Pro Ser Arg Arg His His Cys Arg Ser Lys Ala Lys
                830                 835                 840
Arg Ser Arg His His Gln Asn Pro Arg Ala Glu Ala Pro Cys Tyr
                845                 850                 855
Val Ser His Pro Ser Pro Val Pro Pro Ser Thr Pro Trp Pro Thr
                860                 865                 870
Pro Pro Ala Thr Thr Pro Phe Pro Ala Val Val Gln Pro Tyr Pro
                875                 880                 885
Leu Pro Val Phe Ser Pro Arg Gly Gly Pro Gln Pro Leu Pro Pro
                890                 895                 900
Ala Pro Thr Ser Val Pro Pro Ala Ala Phe Pro Ala Pro Leu Val
                905                 910                 915
Thr Pro Met Val Ala Leu Val Leu Pro Asn Tyr Leu Phe Pro Thr
                920                 925                 930
Pro Pro Ser Tyr Pro Tyr Gly Ala Asp Gln Thr Pro Ala Glu Gly
                935                 940                 945
Pro Pro Thr Pro Ala Ser His Ser Pro Ser Pro Ser Leu Pro Ala
                950                 955                 960
Leu Pro Pro Ser Pro Pro His Arg Pro Asp Ser Pro Leu Phe Asn
                965                 970                 975
Ser Arg Cys Ser Ser Pro Leu Gln Leu Asn Leu Leu Gln Leu Glu
                980                 985                 990
Glu Leu Pro Arg Ala Glu Gly Ala Ala Val Ala Gly Gly Pro Gly
                995                 1000                1005
Ser Ser Ala Gly Pro Pro Pro Ser Ala Glu Ala Ala Glu Pro
                1010                1015                1020
Glu Ala Arg Leu Ala Glu Val Thr Glu Ser Ser Asn Gln Asp Ala
                1025                1030                1035
Leu Ser Gly Ser Ser Asp Leu Leu Glu Leu Leu Leu Gln Glu Asp
                1040                1045                1050
Ser Arg Ser Gly Thr Gly Ser Ala Ala Ser Gly Ser Leu Gly Ser
                1055                1060                1065
Gly Leu Gly Ser Gly Ser Gly Ser His Glu Gly Gly Ser
                1070                1075                1080
Thr Ser Ala Ser Ile Thr Arg Ser Ser Gln Ser Ser His Thr Ser
                1085                1090                1095
Lys Tyr Phe Gly Ser Ile Asp Ser Ser Glu Ala Glu Ala Gly Ala
                1100                1105                1110
Ala Arg Gly Gly Ala Glu Pro Gly Asp Gln Val Ile Lys Tyr Val
                1115                1120                1125
Leu Gln Asp Pro Ile Trp Leu Leu Met Ala Asn Ala Asp Gln Arg
                1130                1135                1140
Val Met Met Thr Tyr Gln Val Pro Ser Arg Asp Met Thr Ser Val
                1145                1150                1155
Leu Lys Gln Asp Arg Glu Arg Leu Arg Ala Met Gln Lys Gln Gln
                1160                1165                1170
Pro Arg Phe Ser Glu Asp Gln Arg Arg Glu Leu Gly Ala Val His
                1175                1180                1185
```

-continued

```
Ser Trp Val Arg Lys Gly Gln Leu Pro Arg Ala Leu Asp Val Met
            1190                1195                1200

Ala Cys Val Asp Cys Gly Ser Ser Thr Gln Asp Pro Gly His Pro
            1205                1210                1215

Asp Asp Pro Leu Phe Ser Glu Leu Asp Gly Leu Gly Leu Glu Pro
            1220                1225                1230

Met Glu Glu Gly Gly Gly Glu Gln Gly Ser Ser Gly Gly Gly Ser
            1235                1240                1245

Gly Glu Gly Glu Gly Cys Glu Glu Ala Gln Gly Gly Ala Lys Ala
            1250                1255                1260

Ser Ser Ser Gln Asp Leu Ala Met Glu Glu Glu Glu Gly Arg
            1265                1270                1275

Ser Ser Ser Ser Pro Ala Leu Pro Thr Ala Gly Asn Cys Thr Ser
            1280                1285                1290
```

<210> SEQ ID NO 7
<211> LENGTH: 875
<212> TYPE: PRT
<213> ORGANISM: artificial sequence
<220> FEATURE:
<223> OTHER INFORMATION: Peptide sequence of largest deduced open
      reading frame from RIGUI 6.6

<400> SEQUENCE: 7

```
Met Ser Gly Pro Leu Glu Gly Ala Asp Gly Gly Gly Asp Pro Arg
             5                  10                  15

Pro Gly Glu Ser Phe Cys Pro Gly Gly Val Pro Ser Pro Gly Pro
            20                  25                  30

Pro Gln His Arg Pro Cys Pro Gly Pro Ser Leu Ala Asp Asp Thr
            35                  40                  45

Asp Ala Asn Ser Asn Gly Ser Ser Gly Asn Glu Ser Asn Gly His
            50                  55                  60

Glu Ser Arg Gly Ala Ser Gln Arg Ser Ser His Ser Ser Ser Ser
            65                  70                  75

Gly Asn Gly Lys Asp Ser Ala Leu Leu Glu Thr Thr Glu Ser Ser
            80                  85                  90

Lys Ser Thr Asn Ser Gln Ser Pro Ser Pro Pro Ser Ser Ser Ile
            95                  100                 105

Ala Tyr Ser Leu Leu Ser Ala Ser Ser Glu Gln Asp Asn Pro Ser
           110                  115                 120

Thr Ser Gly Cys Ser Ser Glu Gln Ser Ala Arg Ala Arg Thr Gln
           125                  130                 135

Lys Glu Leu Met Thr Ala Leu Arg Glu Leu Lys Leu Arg Leu Pro
           140                  145                 150

Pro Glu Arg Arg Gly Lys Gly Arg Ser Gly Thr Leu Ala Thr Leu
           155                  160                 165

Gln Tyr Ala Leu Ala Cys Val Lys Gln Val Gln Ala Asn Gln Glu
           170                  175                 180

Tyr Tyr Gln Gln Trp Ser Leu Glu Glu Gly Glu Pro Cys Ser Met
           185                  190                 195

Asp Met Ser Thr Tyr Thr Leu Glu Glu Leu Glu His Ile Thr Ser
           200                  205                 210

Glu Tyr Thr Leu Gln Asn Gln Asp Thr Phe Ser Val Ala Val Ser
           215                  220                 225

Phe Leu Thr Gly Arg Ile Val Tyr Ile Ser Glu Gln Ala Ala Val
```

-continued

```
                230                 235                 240
Leu Leu Arg Cys Lys Arg Asp Val Phe Arg Gly Thr Arg Phe Ser
                245                 250                 255
Glu Leu Leu Ala Pro Gln Asp Val Gly Val Phe Tyr Gly Ser Thr
                260                 265                 270
Ala Pro Ser Arg Leu Pro Thr Trp Gly Thr Gly Ala Ser Ala Gly
                275                 280                 285
Ser Gly Leu Arg Asp Phe Thr Gln Glu Lys Ser Val Phe Cys Arg
                290                 295                 300
Ile Arg Gly Gly Pro Asp Arg Asp Pro Gly Pro Arg Tyr Gln Pro
                305                 310                 315
Phe Arg Leu Thr Pro Tyr Val Thr Lys Ile Arg Val Ser Asp Gly
                320                 325                 330
Ala Pro Ala Gln Pro Cys Cys Leu Leu Ile Ala Glu Arg Ile His
                335                 340                 345
Ser Gly Tyr Glu Ala Pro Arg Ile Pro Pro Asp Lys Arg Ile Phe
                350                 355                 360
Thr Thr Arg His Thr Pro Ser Cys Leu Phe Gln Asp Val Asp Glu
                365                 370                 375
Arg Ala Ala Pro Leu Leu Gly Tyr Leu Pro Gln Asp Leu Leu Gly
                380                 385                 390
Ala Pro Val Leu Leu Phe Leu His Pro Glu Asp Arg Pro Leu Met
                395                 400                 405
Leu Ala Ile His Lys Lys Ile Leu Gln Leu Ala Gly Gln Pro Phe
                410                 415                 420
Asp His Ser Pro Ile Arg Phe Cys Ala Arg Asn Gly Glu Tyr Val
                425                 430                 435
Thr Met Asp Thr Ser Trp Ala Gly Phe Val His Pro Trp Ser Arg
                440                 445                 450
Lys Val Ala Phe Val Leu Gly Arg His Lys Val Arg Thr Ala Pro
                455                 460                 465
Leu Asn Glu Asp Val Phe Thr Pro Pro Ala Pro Ser Pro Ala Pro
                470                 475                 480
Ser Leu Asp Thr Asp Ile Gln Glu Leu Ser Glu Gln Ile His Arg
                485                 490                 495
Leu Leu Leu Gln Pro Val His Ser Pro Ser Pro Thr Gly Leu Cys
                500                 505                 510
Gly Val Gly Ala Val Thr Ser Pro Gly Pro Leu His Ser Pro Gly
                515                 520                 525
Ser Ser Ser Asp Ser Asn Gly Gly Asp Ala Glu Gly Pro Gly Pro
                530                 535                 540
Pro Ala Pro Val Thr Phe Gln Gln Ile Cys Lys Asp Val His Leu
                545                 550                 555
Val Lys His Gln Gly Gln Gln Leu Phe Ile Glu Ser Arg Ala Arg
                560                 565                 570
Pro Gln Ser Arg Pro Arg Leu Pro Ala Thr Gly Thr Phe Lys Ala
                575                 580                 585
Lys Ala Leu Pro Cys Gln Ser Pro Asp Pro Glu Leu Glu Ala Gly
                590                 595                 600
Ser Ala Pro Val Gln Ala Pro Leu Ala Leu Val Pro Glu Glu Ala
                605                 610                 615
Glu Arg Lys Glu Ala Ser Ser Cys Ser Tyr Gln Gln Ile Asn Cys
                620                 625                 630
```

```
Leu Asp Ser Ile Leu Arg Tyr Leu Glu Ser Cys Asn Leu Pro Ser
            635                 640                 645

Thr Thr Lys Arg Lys Cys Ala Ser Ser Ser Tyr Thr Thr Ser
            650                 655                 660

Ser Ala Ser Asp Asp Arg Gln Arg Thr Gly Pro Val Ser Val
            665                 670                 675

Gly Thr Lys Lys Asp Pro Pro Ser Ala Ala Leu Ser Gly Glu Gly
            680                 685                 690

Ala Thr Pro Arg Lys Glu Pro Val Val Gly Gly Thr Leu Ser Pro
            695                 700                 705

Leu Ala Leu Ala Asn Lys Ala Glu Ser Val Val Ser Val Thr Ser
            710                 715                 720

Gln Cys Ser Phe Ser Ser Thr Ile Val His Val Gly Asp Lys Lys
            725                 730                 735

Pro Pro Glu Ser Asp Ile Ile Met Met Glu Asp Leu Pro Gly Leu
            740                 745                 750

Ala Pro Gly Pro Ala Pro Ser Pro Ala Pro Ser Pro Thr Val Ala
            755                 760                 765

Pro Asp Pro Ala Pro Asp Ala Tyr Arg Pro Val Gly Leu Thr Lys
            770                 775                 780

Ala Val Leu Ser Leu His Thr Gln Lys Glu Glu Gln Ala Phe Leu
            785                 790                 795

Ser Arg Phe Arg Asp Leu Gly Arg Leu Arg Gly Leu Asp Ser Ser
            800                 805                 810

Ser Thr Ala Pro Ser Ala Leu Gly Glu Arg Gly Ser His Leu Gly
            815                 820                 825

Pro Pro Gly Ala Cys Pro Leu Pro Ser Leu Gly Leu Asp Cys Trp
            830                 835                 840

Gly Val Gly Leu Lys Gly Gly Val Ser Ala Pro Gly Thr Gln Ala
            845                 850                 855

Gly Val Ala Ser Thr Thr Arg Pro Cys Leu Gly Thr Gly Pro Ser
            860                 865                 870

Leu Ala Ser Pro His
            875

<210> SEQ ID NO 8
<211> LENGTH: 798
<212> TYPE: PRT
<213> ORGANISM: artificial sequence
<220> FEATURE:
<223> OTHER INFORMATION: Peptide sequence of largest deduced open
      reading frame from RIGUI 3.0

<400> SEQUENCE: 8

Met Ser Gly Pro Leu Glu Gly Ala Asp Gly Gly Asp Pro Arg
              5                  10                  15

Pro Gly Glu Ser Phe Cys Pro Gly Gly Val Pro Ser Pro Gly Pro
             20                  25                  30

Pro Gln His Arg Pro Cys Pro Gly Pro Ser Leu Ala Asp Asp Thr
             35                  40                  45

Asp Ala Asn Ser Asn Gly Ser Ser Gly Asn Glu Ser Asn Gly His
             50                  55                  60

Glu Ser Arg Gly Ala Ser Gln Arg Ser Ser His Ser Ser Ser Ser
             65                  70                  75

Gly Asn Gly Lys Asp Ser Ala Leu Leu Glu Thr Thr Glu Ser Ser
```

-continued

```
                80                  85                  90
Lys Ser Thr Asn Ser Gln Ser Pro Ser Pro Pro Ser Ser Ile
                95                 100                 105
Ala Tyr Ser Leu Leu Ser Ala Ser Ser Glu Gln Asp Asn Pro Ser
               110                 115                 120
Thr Ser Gly Cys Ser Ser Glu Gln Ser Ala Arg Ala Arg Thr Gln
               125                 130                 135
Lys Glu Leu Met Thr Ala Leu Arg Glu Leu Lys Leu Arg Leu Pro
               140                 145                 150
Pro Glu Arg Arg Gly Lys Gly Arg Ser Gly Thr Leu Ala Thr Leu
               155                 160                 165
Gln Tyr Ala Leu Ala Cys Val Lys Gln Val Gln Ala Asn Gln Glu
               170                 175                 180
Tyr Tyr Gln Gln Trp Ser Leu Glu Glu Gly Glu Pro Cys Ser Met
               185                 190                 195
Asp Met Ser Thr Tyr Thr Leu Glu Glu Leu Glu His Ile Thr Ser
               200                 205                 210
Glu Tyr Thr Leu Gln Asn Gln Asp Thr Phe Ser Val Ala Val Ser
               215                 220                 225
Phe Leu Thr Gly Arg Ile Val Tyr Ile Ser Glu Gln Ala Ala Val
               230                 235                 240
Leu Leu Arg Cys Lys Arg Asp Val Phe Arg Gly Thr Arg Phe Ser
               245                 250                 255
Glu Leu Leu Ala Pro Gln Asp Val Gly Val Phe Tyr Gly Ser Thr
               260                 265                 270
Ala Pro Ser Arg Leu Pro Thr Trp Gly Thr Gly Ala Ser Ala Gly
               275                 280                 285
Ser Gly Leu Arg Asp Phe Thr Gln Glu Lys Ser Val Phe Cys Arg
               290                 295                 300
Ile Arg Gly Gly Pro Asp Arg Asp Pro Gly Pro Arg Tyr Gln Pro
               305                 310                 315
Phe Arg Leu Thr Pro Tyr Val Thr Lys Ile Arg Val Ser Asp Gly
               320                 325                 330
Ala Pro Ala Gln Pro Cys Cys Leu Leu Ile Ala Glu Arg Ile His
               335                 340                 345
Ser Gly Tyr Glu Ala Pro Arg Ile Pro Pro Asp Lys Arg Ile Phe
               350                 355                 360
Thr Thr Arg His Thr Pro Ser Cys Leu Phe Gln Asp Val Asp Glu
               365                 370                 375
Arg Ala Ala Pro Leu Leu Gly Tyr Leu Pro Gln Asp Leu Leu Gly
               380                 385                 390
Ala Pro Val Leu Leu Phe Leu His Pro Glu Asp Arg Pro Leu Met
               395                 400                 405
Leu Ala Ile His Lys Lys Ile Leu Gln Leu Ala Gly Gln Pro Phe
               410                 415                 420
Asp His Ser Pro Ile Arg Phe Cys Ala Arg Asn Gly Glu Tyr Val
               425                 430                 435
Thr Met Asp Thr Ser Trp Ala Gly Phe Val His Pro Trp Ser Arg
               440                 445                 450
Lys Val Ala Phe Val Leu Gly Arg His Lys Val Arg Thr Ala Pro
               455                 460                 465
Leu Asn Glu Asp Val Phe Thr Pro Pro Ala Pro Ser Pro Ala Pro
               470                 475                 480
```

-continued

```
Ser Leu Asp Thr Asp Ile Gln Glu Leu Ser Glu Gln Ile His Arg
                485                 490                 495

Leu Leu Leu Gln Pro Val His Ser Pro Ser Pro Thr Gly Leu Cys
        500                 505                 510

Gly Val Gly Ala Val Thr Ser Pro Gly Pro Leu His Ser Pro Gly
        515                 520                 525

Ser Ser Ser Asp Ser Asn Gly Gly Asp Ala Glu Gly Pro Gly Pro
        530                 535                 540

Pro Ala Pro Val Thr Phe Gln Gln Ile Cys Lys Asp Val His Leu
        545                 550                 555

Val Lys His Gln Gly Gln Gln Leu Phe Ile Glu Ser Arg Ala Arg
        560                 565                 570

Pro Gln Ser Arg Pro Arg Leu Pro Ala Thr Gly Thr Phe Lys Ala
        575                 580                 585

Lys Ala Leu Pro Cys Gln Ser Pro Asp Pro Glu Leu Glu Ala Gly
        590                 595                 600

Ser Ala Pro Val Gln Ala Pro Leu Ala Leu Val Pro Glu Glu Ala
        605                 610                 615

Glu Arg Lys Glu Ala Ser Ser Cys Ser Tyr Gln Gln Ile Asn Cys
        620                 625                 630

Leu Asp Ser Ile Leu Arg Tyr Leu Glu Ser Cys Asn Leu Pro Ser
        635                 640                 645

Thr Thr Lys Arg Lys Cys Ala Ser Ser Ser Tyr Thr Thr Ser
        650                 655                 660

Ser Ala Ser Asp Asp Asp Arg Gln Arg Thr Gly Pro Val Ser Val
        665                 670                 675

Gly Thr Lys Lys Asp Pro Pro Ser Ala Ala Leu Ser Gly Glu Gly
        680                 685                 690

Ala Thr Pro Arg Lys Glu Pro Val Val Gly Gly Thr Leu Ser Pro
        695                 700                 705

Leu Ala Leu Ala Asn Lys Ala Glu Ser Val Val Ser Val Thr Ser
        710                 715                 720

Gln Cys Ser Phe Ser Ser Thr Ile Val His Val Gly Asp Lys Lys
        725                 730                 735

Pro Pro Glu Ser Asp Ile Ile Met Met Glu Asp Leu Pro Gly Leu
        740                 745                 750

Ala Pro Gly Pro Ala Pro Ser Pro Thr Pro Phe Trp Asp His Leu
        755                 760                 765

Gln Glu Ser Met Arg Gly Phe Leu Leu Leu Cys Pro Asn Ser Gln
        770                 775                 780

Asn Ser Asp Val Ala Arg Pro Thr Ser Gly Lys Leu Pro Gln Leu
        785                 790                 795

Leu Pro Pro
```

<210> SEQ ID NO 9
<211> LENGTH: 4700
<212> TYPE: DNA
<213> ORGANISM: artificial sequence
<220> FEATURE:
<223> OTHER INFORMATION: Nucleotide sequence of m-rigui, a murine brain
      cDNA homologous to a human RIGUI 4.7 cDNA probe

<400> SEQUENCE: 9
cgggtcgacc cacgcgtccg cccacgcgtc cggcggagct tctgggttgc gggccgaaac     60

-continued

| | |
|---|---|
| ggcaagcgga tggagggcgc tcgaacggcc aggtgtcgtg attaaattag tcagccctca | 120 |
| gagacaggcg tcctacctcc tttatccaga cctcaaaagc cccgttgtgc acccgtggtg | 180 |
| gcttcttcac cttccctgtt tcgtcctcca ctgtatggcc cagacatgag tggtcccta | 240 |
| gaagggccg atgggggagg agaccccagg cccggagaac cttttttgtcc tggaggagtc | 300 |
| ccatcccctg ggccccgca gcaccggcct tgtccaggcc ccagcctggc tgatgacact | 360 |
| gatgcaaaca gcaatggctc aagtggcaat gagtccaacg gacccgagtc cagggcgca | 420 |
| tctcagcgga gttctcatag ttcctcttct ggcaatggca aggactcagc tctgctggag | 480 |
| accactgaga gcagcaagag tacaaactca cagagcccat ccccacccag cagctccatt | 540 |
| gcctacagcc tcctgagtgc gagctcagag caggacaacc catctaccag tggctgcagc | 600 |
| agtgaacagt cagctcgagc caggacccag aaagaactca tgactgcact tcgggagctc | 660 |
| aaacttcgac tgccaccaga gcgtcggggc aagggccgct ctgggacctt ggccacactg | 720 |
| cagtacgctc tggcctgtgt caagcaggtt caggctaacc aggaatatta ccagcagtgg | 780 |
| agtctggagg agggtgagcc ttgtgccatg gacatgtcta cttacacccct ggaggaattg | 840 |
| gagcatatca catccgaata cacacttcga aaccaggaca ccttctctgt ggctgtgtcc | 900 |
| ttcctgacag gccggattgt ctatatttcg gagcaggcag gtgtcctgct gcgttgcaaa | 960 |
| cgggatgtgt ttcggggtgc ccgcttctca gagctcctgg ctccccagga tgtgggtgtc | 1020 |
| ttctatggct ctactacacc atctcgactg cccacctggg gcactggcac ctctgcaggt | 1080 |
| tcaggtctca aggacttcac ccaggaaaag tctgtcttct gccgaatcag aggaggtcct | 1140 |
| gaccgggatc cagggcctcg gtaccagcca ttccgcctaa ccccatatgt gaccaagatt | 1200 |
| cgggtctcag atggagcccc tgcacagccg tgctgcctac tcattgccga gcgcatccac | 1260 |
| tctggttatg aagctccccg gatccctcct gacaagagga tcttcaccac ccgacacaca | 1320 |
| ccaagctgcc tcttccagga tgtagatgaa agggctgccc cactgctggg ttaccttccc | 1380 |
| caggatctcc tgggggctcc agtacttctc tttctacatc ctgaggaccg accctcatg | 1440 |
| ctggccattc ataagaagat actgcagctg gcaggccagc cctttgacca ttcccctatt | 1500 |
| cgcttctgtg ctcggaacgg ggaatatgtc accatggaca ccagctgggc cggttttgtg | 1560 |
| caccctggA gccgcaaggt ggctttcgtg ttgggtcgcc ataaagtgcg cacggcaccc | 1620 |
| ctgaatgagg acgtcttcac tccccccagcc cccagcccag ctccgtccct ggactctgat | 1680 |
| atccaggagc tctcagagca gatccatcga ttgctgctgc agcctgtgca cagctccagc | 1740 |
| cccacggggc tctgtggagt tggccctctg atgtcccctg gtcctctaca cagccctggc | 1800 |
| tcctccagtg atagcaatgg gggggacgct gagggcctg ggcctcctgc tccagtgact | 1860 |
| ttccagcaga tctgtaagga tgtgcatctg gtaaagcacc agggacaaca gctcttcatt | 1920 |
| gaatctcggg ccaagccccc accccggccc cgcctccttg ctacaggtac attcaaagcc | 1980 |
| aaagtccttc cctgccagtc cccaaacccc gaactggagg tggcccagt tcctgaccaa | 2040 |
| gcctcgttag ccttggcccc tgaggagcca gagaggaaa aaacctctgg ctgttcctac | 2100 |
| cagcagatca actgcctgga cagcatcctc aggtatttgg agagctgcaa cattcccagt | 2160 |
| acaaccaagc gtaaatgtgc ctcctcctcc tcctacactg cctcttcagc ctctgatgat | 2220 |
| gacaagcaga gggcaggtcc agttcctgtg ggggccaaga agatccgtc gtcagcaatg | 2280 |
| ctgtctgggg agggggcaac tcctcggaag gagccagtgg tgggaggcac cctgagcccg | 2340 |
| ctcgccctgg ccaataaggc agagagcgtg gtgtccgtca ccagtcagtg tagcttcagc | 2400 |
| tccaccatcg tccatgtggg agacaagaag ccccccggagt cggacatcat catgatggaa | 2460 |

```
gacctgcctg gcctggcccc tgcccagcc  cccagtccgg  cccccagccc  cacagtagcc   2520
cctgacccaa cccagatgc  ttatcgccca gtgggtctga  ccaaggccgt  gctgtccctg   2580
cacacacaga aggaagagca agccttcctc aaccgcttca  gagatcttgg  caggcttcgt   2640
ggacttgaca cctcttctgt ggcccctca  gccctggct   gccaccatgg  ccccattccc   2700
cctggtcgcc gacaccactg ccgatctaaa gcaaagcgtt  cccgccacca  ccaccaccag   2760
accccccggc cgaaactcc  ctgctatgtc tcccatcctt  cacctgtgcc  ctcttctgga   2820
ccctggccac ccccaccagc cacgacccc  ttcccagcaa  tggtccagcc  ctacccactc   2880
ccagtattct cccctcgagg aggacccag  ccccttcccc  ctgcccctac  atctgtgtcc   2940
cctgctacct tcccttctcc cttagtgacc ccaatggtgg  ccttggtgct  ccctaactat   3000
ctattcccta ccccacctag ttatccatat ggggtgtccc  aggcccctgt  tgagggccca   3060
cccacgcctg cttcccactc gccctctcca  tccctgcccc  caccacctct  cagcccccc    3120
caccgcccag actccccact gttcaactcg agatgcagct  cccactcca   gctcaatctg   3180
ctgcagcttg aggagtcccc ccgcacggag ggggcgctg   ctgcaggagg  cccaggaagc   3240
agtgctgggc ccctgcctcc cagtgaggag actgctgagc  cagaggccag  attggtggag   3300
gttactgagt cgtccaatca ggatgcactt tcaggtccca  gcgacctgct  ggagctactg   3360
ctccaagaag actctcgctc gggcacaggc tccgcagcct  caggctccct  gggctctggc   3420
ctgggctctg gtctggttc  aggatcccac gaaggggaa   gcacctcagc  cagcatcacc   3480
cgcagcagtc agagcagcca tacaagcaag tactttggca  gcatcgactc  ttccgaggct   3540
gaagctgggc ctgctcgggc caggactgag cctgggacc   aggtcattaa  gtgtgtgctc   3600
caggacccca tctggctgct catggccaat gccgaccagc  gtgtcatgat  gacataccag   3660
gtgccgtcca gggatgcagc ctctgtgctg aagcaagacc  gggagaggct  ccgggccatg   3720
cagaaacagc agccacggtt ctcagaggac cagaggcggg  aactgggtgc  tgtgcactcc   3780
tgggtccgga agggccagct gcctcgggcc cttgatgtga  tggcgtgtgt  ggactgtggc   3840
agcagcgttc aagatcctgg ccactctgat gacccgctct  tctcagaact  ggatggattg   3900
gggctggagc ccatggaaga gggtggaggc gaggtggtg   ggtgtggtgt  tggcggtggt   3960
gggggtgatg gtggtgagga ggcccagacc caaattgggg  ctaagggttc  aagctctcag   4020
gactctgcca tggaggaaga agagcaaggt gggggctcat  ccagcccagc  tttacctgca   4080
gaagaaaaca gcaccagcta gatccatttt ggggccgctt  acagcagtct  aatgagaggc   4140
ttcctttcga ccatgttggg gttcttataa ctcaagatac  agctggacca  accaatagga   4200
aactgcccca gcttctccca acatagggg  ctggaccccc  attaccagcc  caggcacagg   4260
agctgcctct agcttcttag cagagtggaa gttctcagcc  ccatttggag  gattgtccac   4320
gcccgtccca ctgaggagac gggcgggtct tcggttaagg  ttgctgacaa  gctgctgaag   4380
tggtctgtcc aaatcccagc tgagcctgag tcccagtcgc  agggttgggg  ctgcacttat   4440
ttatttggga gagacagctc actctcccac ctcaccccaa  gatgggagga  ggggaacctg   4500
ggatctgtgt aggatccagg tccgtgaacc cctagctgct  ccagggtggg  ggaggttggt   4560
ggaccatgga gtccctggtg ctgcccctca ggtgggaccc  aggtgttctc  agctctaccc   4620
tctaccaatg acatttgtgt ttttgatatt gtgtctgtta  tttttttttt  aatacaaaat   4680
gacaaaatga aaaccaaaa                                                  4700
```

<210> SEQ ID NO 10

-continued

```
<211> LENGTH: 1291
<212> TYPE: PRT
<213> ORGANISM: artificial sequence
<220> FEATURE:
<223> OTHER INFORMATION: Protein sequence encoded by m-rigui homologue

<400> SEQUENCE: 10
```

Met Ser Gly Pro Leu Glu Gly Ala Asp Gly Gly Asp Pro Arg
            5                   10               15

Pro Gly Glu Pro Phe Cys Pro Gly Val Pro Ser Pro Gly Ala
          20                 25             30

Pro Gln His Arg Pro Cys Pro Gly Pro Ser Leu Ala Asp Thr
          35                 40             45

Asp Ala Asn Ser Asn Gly Ser Ser Gly Asn Glu Ser Asn Gly Pro
          50                 55             60

Glu Ser Arg Gly Ala Ser Gln Arg Ser Ser His Ser Ser Ser Ser
          65                 70             75

Gly Asn Gly Lys Asp Ser Ala Leu Leu Glu Thr Thr Glu Ser Ser
          80                 85             90

Lys Ser Thr Asn Ser Gln Ser Pro Ser Pro Ser Ser Ser Ile
          95               100           105

Ala Tyr Ser Leu Leu Ser Ala Ser Ser Glu Gln Asp Asn Pro Ser
         110               115           120

Thr Ser Gly Cys Ser Ser Glu Gln Ser Ala Arg Ala Arg Thr Gln
         125               130           135

Lys Glu Leu Met Thr Ala Leu Arg Glu Leu Lys Leu Arg Leu Pro
         140               145           150

Pro Glu Arg Arg Gly Lys Gly Arg Ser Gly Thr Leu Ala Thr Leu
         155               160           165

Gln Tyr Ala Leu Ala Cys Val Lys Gln Val Gln Ala Asn Gln Glu
         170               175           180

Tyr Tyr Gln Gln Trp Ser Leu Glu Glu Gly Glu Pro Cys Ala Met
         185               190           195

Asp Met Ser Thr Tyr Thr Leu Glu Glu Leu Glu His Ile Thr Ser
         200               205           210

Glu Tyr Thr Leu Arg Asn Gln Asp Thr Phe Ser Val Ala Val Ser
         215               220           225

Phe Leu Thr Gly Arg Ile Val Tyr Ile Ser Glu Gln Ala Gly Val
         230               235           240

Leu Leu Arg Cys Lys Arg Asp Val Phe Arg Gly Ala Arg Phe Ser
         245               250           255

Glu Leu Leu Ala Pro Gln Asp Val Gly Val Phe Tyr Gly Ser Thr
         260               265           270

Thr Pro Ser Arg Leu Pro Thr Trp Gly Thr Gly Thr Ser Ala Gly
         275               280           285

Ser Gly Leu Lys Asp Phe Thr Gln Glu Lys Ser Val Phe Cys Arg
         290               295           300

Ile Arg Gly Gly Pro Asp Arg Asp Pro Gly Pro Arg Tyr Gln Pro
         305               310           315

Phe Arg Leu Thr Pro Tyr Val Thr Lys Ile Arg Val Ser Asp Gly
         320               325           330

Ala Pro Ala Gln Pro Cys Cys Leu Leu Ile Ala Glu Arg Ile His
         335               340           345

Ser Gly Tyr Glu Ala Pro Arg Ile Pro Pro Asp Lys Arg Ile Phe
         350               355           360

-continued

```
Thr Thr Arg His Thr Pro Ser Cys Leu Phe Gln Asp Val Asp Glu
            365                 370                 375
Arg Ala Ala Pro Leu Leu Gly Tyr Leu Pro Gln Asp Leu Leu Gly
            380                 385                 390
Ala Pro Val Leu Leu Phe Leu His Pro Glu Asp Arg Pro Leu Met
            395                 400                 405
Leu Ala Ile His Lys Lys Ile Leu Gln Leu Ala Gly Gln Pro Phe
            410                 415                 420
Asp His Ser Pro Ile Arg Phe Cys Ala Arg Asn Gly Glu Tyr Val
            425                 430                 435
Thr Met Asp Thr Ser Trp Ala Gly Phe Val His Pro Trp Ser Arg
            440                 445                 450
Lys Val Ala Phe Val Leu Gly Arg His Lys Val Arg Thr Ala Pro
            455                 460                 465
Leu Asn Glu Asp Val Phe Thr Pro Pro Ala Pro Ser Pro Ala Pro
            470                 475                 480
Ser Leu Asp Ser Asp Ile Gln Glu Leu Ser Glu Gln Ile His Arg
            485                 490                 495
Leu Leu Leu Gln Pro Val His Ser Ser Pro Thr Gly Leu Cys
            500                 505                 510
Gly Val Gly Pro Leu Met Ser Pro Gly Pro Leu His Ser Pro Gly
            515                 520                 525
Ser Ser Ser Asp Ser Asn Gly Gly Asp Ala Glu Gly Pro Gly Pro
            530                 535                 540
Pro Ala Pro Val Thr Phe Gln Gln Ile Cys Lys Asp Val His Leu
            545                 550                 555
Val Lys His Gln Gly Gln Gln Leu Phe Ile Glu Ser Arg Ala Lys
            560                 565                 570
Pro Pro Pro Arg Pro Arg Leu Leu Ala Thr Gly Thr Phe Lys Ala
            575                 580                 585
Lys Val Leu Pro Cys Gln Ser Pro Asn Pro Glu Leu Glu Val Ala
            590                 595                 600
Pro Val Pro Asp Gln Ala Ser Leu Ala Leu Ala Pro Glu Glu Pro
            605                 610                 615
Glu Arg Lys Glu Thr Ser Gly Cys Ser Tyr Gln Gln Ile Asn Cys
            620                 625                 630
Leu Asp Ser Ile Leu Arg Tyr Leu Glu Ser Cys Asn Ile Pro Ser
            635                 640                 645
Thr Thr Lys Arg Lys Cys Ala Ser Ser Ser Tyr Thr Ala Ser
            650                 655                 660
Ser Ala Ser Asp Asp Asp Lys Gln Arg Ala Gly Pro Val Pro Val
            665                 670                 675
Gly Ala Lys Lys Asp Pro Ser Ser Ala Met Leu Ser Gly Glu Gly
            680                 685                 690
Ala Thr Pro Arg Lys Glu Pro Val Val Gly Gly Thr Leu Ser Pro
            695                 700                 705
Leu Ala Leu Ala Asn Lys Ala Glu Ser Val Val Ser Val Thr Ser
            710                 715                 720
Gln Cys Ser Phe Ser Ser Thr Ile Val His Val Gly Asp Lys Lys
            725                 730                 735
Pro Pro Glu Ser Asp Ile Ile Met Met Glu Asp Leu Pro Gly Leu
            740                 745                 750
```

-continued

```
Ala Pro Gly Pro Ala Pro Ser Pro Ala Pro Ser Pro Thr Val Ala
            755                 760                 765
Pro Asp Pro Thr Pro Asp Ala Tyr Arg Pro Val Gly Leu Thr Lys
            770                 775                 780
Ala Val Leu Ser Leu His Thr Gln Lys Glu Glu Gln Ala Phe Leu
            785                 790                 795
Asn Arg Phe Arg Asp Leu Gly Arg Leu Arg Gly Leu Asp Thr Ser
            800                 805                 810
Ser Val Ala Pro Ser Ala Pro Gly Cys His His Gly Pro Ile Pro
            815                 820                 825
Pro Gly Arg Arg His His Cys Arg Ser Lys Ala Lys Arg Ser Arg
            830                 835                 840
His His His His Gln Thr Pro Arg Pro Glu Thr Pro Cys Tyr Val
            845                 850                 855
Ser His Pro Ser Pro Val Pro Ser Ser Gly Pro Trp Pro Pro Pro
            860                 865                 870
Pro Ala Thr Thr Pro Phe Pro Ala Met Val Gln Pro Tyr Pro Leu
            875                 880                 885
Pro Val Phe Ser Pro Arg Gly Gly Pro Gln Pro Leu Pro Pro Ala
            890                 895                 900
Pro Thr Ser Val Ser Pro Ala Thr Phe Pro Ser Pro Leu Val Thr
            905                 910                 915
Pro Met Val Ala Leu Val Leu Pro Asn Tyr Leu Phe Pro Thr Pro
            920                 925                 930
Pro Ser Tyr Pro Tyr Gly Val Ser Gln Ala Pro Val Glu Gly Pro
            935                 940                 945
Pro Thr Pro Ala Ser His Ser Pro Ser Pro Ser Leu Pro Pro Pro
            950                 955                 960
Pro Leu Ser Pro Pro His Arg Pro Asp Ser Pro Leu Phe Asn Ser
            965                 970                 975
Arg Cys Ser Ser Pro Leu Gln Leu Asn Leu Leu Gln Leu Glu Glu
            980                 985                 990
Ser Pro Arg Thr Glu Gly Gly Ala Ala Gly Gly Pro Gly Ser
            995                1000                1005
Ser Ala Gly Pro Leu Pro Pro Ser Glu Glu Thr Ala Glu Pro Glu
           1010                1015                1020
Ala Arg Leu Val Glu Val Thr Glu Ser Ser Asn Gln Asp Ala Leu
           1025                1030                1035
Ser Gly Ser Ser Asp Leu Leu Glu Leu Leu Gln Glu Asp Ser
           1040                1045                1050
Arg Ser Gly Thr Gly Ser Ala Ala Ser Gly Ser Leu Gly Ser Gly
           1055                1060                1065
Leu Gly Ser Gly Ser Gly Ser Gly Ser His Glu Gly Gly Ser Thr
           1070                1075                1080
Ser Ala Ser Ile Thr Arg Ser Ser Gln Ser Ser His Thr Ser Lys
           1085                1090                1095
Tyr Phe Gly Ser Ile Asp Ser Ser Glu Ala Glu Ala Gly Ala Ala
           1100                1105                1110
Arg Ala Arg Thr Glu Pro Gly Asp Gln Val Ile Lys Cys Val Leu
           1115                1120                1125
Gln Asp Pro Ile Trp Leu Leu Met Ala Asn Ala Asp Gln Arg Val
           1130                1135                1140
Met Met Thr Tyr Gln Val Pro Ser Arg Asp Ala Ala Ser Val Leu
```

-continued

```
                    1145                1150                1155

Lys Gln Asp Arg Glu Arg Leu Arg Ala Met Gln Lys Gln Gln Pro
                    1160                1165                1170

Arg Phe Ser Glu Asp Gln Arg Glu Leu Gly Ala Val His Ser
                    1175                1180                1185

Trp Val Arg Lys Gly Gln Leu Pro Arg Ala Leu Asp Val Met Ala
                    1190                1195                1200

Cys Val Asp Cys Gly Ser Ser Val Gln Asp Pro Gly His Ser Asp
                    1205                1210                1215

Asp Pro Leu Phe Ser Glu Leu Asp Gly Leu Gly Leu Glu Pro Met
                    1220                1225                1230

Glu Glu Gly Gly Gly Glu Gly Gly Gly Cys Gly Val Gly Gly Gly
                    1235                1240                1245

Gly Gly Asp Gly Gly Glu Glu Ala Gln Thr Gln Ile Gly Ala Lys
                    1250                1255                1260

Gly Ser Ser Ser Gln Asp Ser Ala Met Glu Glu Gly Glu Gln Gly
                    1265                1270                1275

Gly Gly Ser Ser Ser Pro Ala Leu Pro Ala Glu Glu Asn Ser Thr
                    1280                1285                1290

Ser

<210> SEQ ID NO 11
<211> LENGTH: 1127
<212> TYPE: PRT
<213> ORGANISM: D. melanogaster Period
<220> FEATURE:
<223> OTHER INFORMATION: Predicted protein sequence compared with RIGUI
      4.7

<400> SEQUENCE: 11

Met Ile Ile Lys Arg Asn Lys Asp Lys Ser Arg Lys Lys Lys
                    5                   10                  15

Asn Lys Gly Ala Gly Gln Gly Ala Gly Gln Ala Gln Thr Leu Ile
                    20                  25                  30

Ser Ala Ser Thr Ser Leu Glu Gly Arg Asp Glu Glu Lys Pro Arg
                    35                  40                  45

Pro Ser Gly Thr Gly Cys Val Glu Gln Gln Ile Cys Arg Glu Leu
                    50                  55                  60

Gln Asp Gln Gln His Gly Glu Asp His Ser Glu Pro Gln Ala Ile
                    65                  70                  75

Glu Gln Leu Gln Gln Glu Glu Glu Asp Gln Ser Gly Ser Glu
                    80                  85                  90

Ser Glu Ala Asp Arg Val Glu Gly Val Ala Lys Ser Glu Ala Ala
                    95                  100                 105

Gln Ser Phe Pro Ile Pro Ser Pro Leu Ser Val Thr Ile Val Pro
                    110                 115                 120

Pro Ser Met Gly Gly Cys Gly Gly Val Gly His Ala Ala Gly Leu
                    125                 130                 135

Asp Ser Gly Leu Ala Lys Phe Asp Lys Thr Trp Glu Ala Gly Pro
                    140                 145                 150

Gly Lys Leu Glu Ser Met Thr Gly Val Gly Ala Ala Ala Ala Gly
                    155                 160                 165

Thr Gly Gln Arg Gly Glu Arg Val Lys Glu Asp Ser Phe Cys Cys
                    170                 175                 180

Val Ile Ser Met His Asp Gly Ile Val Leu Tyr Thr Thr Pro Ser
```

```
                    185                 190                 195
Ile Thr Asp Val Leu Gly Tyr Pro Arg Leu Met Trp Leu Gly Arg
                200                 205                 210
Ser Phe Ile Asp Phe Val His Leu Lys Ser Glu Thr Phe Ala Ser
                215                 220                 225
Gln Ile Thr Thr Gly Ile Pro Ile Ala Glu Ser Arg Gly Ser Val
                230                 235                 240
Pro Lys Asp Ala Lys Ser Thr Phe Cys Val Met Leu Arg Arg Tyr
                245                 250                 255
Arg Gly Leu Lys Ser Gly Gly Phe Gly Val Ile Gly Arg Pro Pro
                260                 265                 270
Val Ser Tyr Glu Pro Phe Arg Leu Gly Leu Thr Phe Arg Glu Ala
                275                 280                 285
Pro Glu Glu Ala Arg Pro Asp Asn Tyr Met Val Ser Asn Gly Thr
                290                 295                 300
Asn Met Leu Leu Val Ile Cys Ala Thr Pro Ile Lys Ser Ser Met
                305                 310                 315
Lys Val Pro Asp Glu Ile Leu Ser Gln Lys Ser Pro Lys Phe Ala
                320                 325                 330
Ile Arg His Thr Ala Thr Gly Ile Ile Ser His Val Asp Ser Ala
                335                 340                 345
Ala Val Ser Ala Leu Gly Tyr Leu Pro Gln Asp Leu Ile Gly Arg
                350                 355                 360
Ser Ile Met Asp Phe Tyr His His Glu Asp Leu Ser Val Met Lys
                365                 370                 375
Glu Thr Tyr Glu Thr Val Met Lys Lys Gly Gln Thr Ala Gly Ala
                380                 385                 390
Ser Glu Cys Ser Lys Pro Tyr Arg Glu Leu Ile Gln Asn Gly Cys
                395                 400                 405
Tyr Val Leu Leu Glu Asp Glu Trp Thr Ser Phe Val Asn Pro Trp
                410                 415                 420
Ser Arg Lys Leu Glu Phe Val Val Gly His His Arg Val Phe Gln
                425                 430                 435
Gly Pro Lys Gln Cys Asn Val Phe Glu Ala Ala Pro Thr Cys Lys
                440                 445                 450
Leu Lys Ile Ser Glu Glu Ala Gln Ser Arg Asn Thr Arg Ile Lys
                455                 460                 465
Glu Asp Ile Val Lys Arg Leu Ala Glu Thr Val Ser Arg Pro Ser
                470                 475                 480
Asp Thr Val Lys Gln Glu Val Ser Arg Arg Cys Gln Ala Leu Ala
                485                 490                 495
Ser Phe Met Glu Thr Leu Met Asp Glu Val Ser Arg Ala Asp Leu
                500                 505                 510
Lys Leu Glu Leu Pro His Glu Asn Glu Leu Thr Val Ser Glu Arg
                515                 520                 525
Asp Ser Val Met Leu Gly Glu Ile Ser Pro His His Asp Tyr Tyr
                530                 535                 540
Asp Ser Lys Ser Ser Thr Glu Thr Pro Pro Ser Tyr Asn Gln Leu
                545                 550                 555
Asn Tyr Asn Glu Asn Leu Leu Arg Phe Phe Asn Lys Ser Pro Val
                560                 565                 570
Thr Ala Pro Ala Glu Leu Asp Pro Pro Lys Thr Glu Pro Pro Glu
                575                 580                 585
```

```
Pro Arg Gly Thr Cys Val Ser Gly Ala Ser Gly Pro Met Ser Pro
            590                 595                 600

Val His Glu Gly Ser Gly Gly Ser Gly Ser Ser Gly Asn Phe Thr
            605                 610                 615

Thr Ala Ser Asn Ile His Met Ser Ser Val Thr Asn Thr Ser Ile
            620                 625                 630

Ala Gly Thr Gly Gly Thr Gly Thr Gly Thr Gly Thr Gly Thr Gly
            635                 640                 645

Thr Gly Thr Gly Thr Gly Thr Gly Thr Gly Thr Gly Thr Gly Thr
            650                 655                 660

Gly Thr Gly Thr Gly Thr Gly Thr Gly Thr Val Thr Leu Thr Glu
            665                 670                 675

Ser Leu Leu Asn Lys His Asn Asp Glu Met Glu Lys Phe Met Leu
            680                 685                 690

Lys Lys His Arg Glu Ser Arg Gly Arg Thr Gly Glu Lys Ser Lys
            695                 700                 705

Lys Ser Ala Asn Asp Thr Leu Lys Met Leu Glu Tyr Ser Gly Pro
            710                 715                 720

Gly His Gly Ile Lys Arg Gly Gly Ser His Ser Trp Glu Gly Glu
            725                 730                 735

Ala Asn Lys Pro Lys Gln Gln Leu Thr Leu Gly Thr Asp Ala Ile
            740                 745                 750

Lys Gly Ala Ala Gly Ser Ala Gly Gly Ala Val Gly Thr Gly Gly
            755                 760                 765

Val Gly Ser Gly Gly Ala Gly Val Ala Gly Gly Gly Ser Gly
            770                 775                 780

Thr Gly Val Ala Gly Thr Pro Glu Gly Arg Ala Thr Thr Thr Ser
            785                 790                 795

Gln Thr Gly Thr Pro Gly Gly Ala Gly Gly Gly Gly Ala Gly
            800                 805                 810

Ala Ala Ala Ala Ala Gly Ala Ser Ser Ser Val Gly Ser Ser Thr
            815                 820                 825

Pro Gly Pro Ser Ser Tyr Pro Thr Cys Thr Gln Asn Ile Asn Leu
            830                 835                 840

Trp Pro Pro Phe Ser Val Gly Ile Thr Pro Pro Val His Ser Thr
            845                 850                 855

His Thr Ala Met Ala Gln Ser Ser Phe Ser Ser Ala Gly Leu Phe
            860                 865                 870

Pro Thr Phe Tyr Tyr Ile Pro Ala Ser Leu Thr Pro Thr Ser Pro
            875                 880                 885

Thr Arg Ser Pro Arg Met His Lys His Pro His Lys Gly Gly Thr
            890                 895                 900

Asp Met Pro Thr Thr Ser Gln Gln Ala Ala Ala Ala Ala Ala Gln
            905                 910                 915

Ala Met Pro Leu Gln Tyr Met Ala Gly Val Met Tyr Pro His Pro
            920                 925                 930

Ser Leu Phe Tyr Thr His Pro Ala Ala Ala Ala Thr Ala Met
            935                 940                 945

Met Tyr Gln Pro Met Pro Phe Pro Gly Met Ala Asn Ala Leu Gln
            950                 955                 960

Ile Pro Glu Arg Pro Leu Gly Ser Gln Ser Ala Tyr Asn Lys Ser
            965                 970                 975
```

-continued

```
Val Tyr Thr Thr Ile Pro Ala Ser Met Thr Lys Lys Val Pro Gly
                980             985                 990

Ala Phe His Ser Val Ile Thr Thr Pro Ala Gln Val Gln Arg Pro
                995             1000                1005

Ser Ser Gln Ser Ala Ser Val Lys Thr Glu Pro Gly Ser Ser Ala
                1010            1015                1020

Ala Val Ser Asp Pro Lys Lys Glu Val Pro Asp Ser Ser Pro Ile
                1025            1030                1035

Pro Ser Val Met Gly Lys Tyr Asn Ser Lys Pro Pro Cys Ser Ser
                1040            1045                1050

Ser Asn Pro Ala Asn Asn Lys Lys Tyr Thr Asp Ser Asn Gly Asn
                1055            1060                1065

Ser Asp Asp Met Asp Gly Ser Ser Phe Ser Ser Phe Tyr Ser Ser
                1070            1075                1080

Phe Ile Lys Thr Thr Asp Gly Ser Glu Ser Pro Pro Asp Thr Glu
                1085            1090                1095

Lys Asp Pro Lys His Arg Lys Leu Lys Ser Met Ser Thr Ser Glu
                1100            1105                1110

Ser Lys Ile Met Glu His Pro Glu Glu Asp Gln Thr Gln His Gly
                1115            1120                1125

Asp Gly

<210> SEQ ID NO 12
<211> LENGTH: 23
<212> TYPE: PRT
<213> ORGANISM: artificial sequence
<220> FEATURE:
<223> OTHER INFORMATION: Consensus sequence indicates identical residues
      observed in the amino acid sequence alignment
      of the basic-helix-loop-helix motif in greater
      than 50% of SEQ ID Nos. 13-21.

<400> SEQUENCE: 12

Lys Glu Ser Arg Ala Arg Arg Lys Asn Glu Leu Ala Leu Pro
                5               10                  15

Pro Asp Lys Leu Arg Leu Ser Leu
                20

<210> SEQ ID NO 13
<211> LENGTH: 48
<212> TYPE: PRT
<213> ORGANISM: Mus musculus
<220> FEATURE:
<223> OTHER INFORMATION: Peptide sequence of bHLH-PAS gene family member
      NPAS2 (Genbank Accession No. U77969).

<400> SEQUENCE: 13

Ala Lys Arg Ala Ser Arg Asn Lys Ser Glu Lys Lys Arg Arg Asp
                5               10                  15

Gln Phe Asn Val Leu Ile Lys Glu Leu Ser Ser Met Leu Pro Gly
                20              25                  30

Asn Thr Arg Lys Met Asp Lys Thr Thr Val Leu Glu Lys Val Ile
                35              40                  45

Gly Phe Leu

<210> SEQ ID NO 14
<211> LENGTH: 48
<212> TYPE: PRT
<213> ORGANISM: Mus musculus
<220> FEATURE:
```

```
<223> OTHER INFORMATION: Peptide sequence of bHLH-PAS gene family member
      Clock (Genbank Accession No. AF000998).

<400> SEQUENCE: 14

Ala Lys Arg Val Ser Arg Asn Lys Ser Glu Lys Lys Arg Arg Asp
                 5                  10                  15

Gln Phe Asn Val Leu Ile Lys Glu Leu Gly Ser Met Leu Pro Gly
                20                  25                  30

Asn Ala Arg Lys Met Asp Lys Ser Thr Val Leu Gln Lys Ser Ile
                35                  40                  45

Asp Phe Leu

<210> SEQ ID NO 15
<211> LENGTH: 51
<212> TYPE: PRT
<213> ORGANISM: Drosophila melanogaster
<220> FEATURE:
<223> OTHER INFORMATION: Peptide sequence of bHLH-PAS gene family member
      DRO.TRH (Genbank Accession No. U42699).

<400> SEQUENCE: 15

Arg Lys Glu Lys Ser Arg Asp Ala Ala Arg Ser Arg Arg Gly Lys
                 5                  10                  15

Glu Asn Phe Glu Phe Tyr Glu Leu Ala Lys Met Leu Pro Leu Pro
                20                  25                  30

Ala Ala Ile Thr Ser Gln Leu Asp Lys Ala Ser Ile Ile Arg Leu
                35                  40                  45

Leu Thr Ile Ser Tyr Leu
                50

<210> SEQ ID NO 16
<211> LENGTH: 51
<212> TYPE: PRT
<213> ORGANISM: Mus musculus
<220> FEATURE:
<223> OTHER INFORMATION: Peptide sequence of bHLH-PAS gene family member
      MOUSE.SIM1 (Genbank Accession No. D79209).

<400> SEQUENCE: 16

Met Lys Glu Lys Ser Lys Asn Ala Ala Arg Thr Arg Arg Glu Lys
                 5                  10                  15

Glu Asn Ser Glu Phe Tyr Glu Leu Ala Lys Leu Leu Pro Leu Pro
                20                  25                  30

Ser Ala Ile Thr Ser Gln Leu Asp Lys Ala Ala Ser Ile Ile Arg
                35                  40                  45

Leu Thr Thr Ser Tyr Leu
                50

<210> SEQ ID NO 17
<211> LENGTH: 50
<212> TYPE: PRT
<213> ORGANISM: Homo sapiens
<220> FEATURE:
<223> OTHER INFORMATION: Peptide sequence of bHLH-PAS gene family member
      HUMAN.HIFa (Genbank Accession No. U22431).

<400> SEQUENCE: 17

Arg Lys Glu Lys Ser Arg Asp Ala Ala Arg Ser Arg Arg Ser Lys
                 5                  10                  15

Glu Ser Glu Val Phe Tyr Glu Leu Ala His Gln Leu Pro Leu Pro
                20                  25                  30
```

```
His Asn Val Ser Ser His Leu Asp Lys Ala Ser Val Met Arg Leu
                35                  40                  45

Thr Ile Ser Tyr Leu
                50

<210> SEQ ID NO 18
<211> LENGTH: 50
<212> TYPE: PRT
<213> ORGANISM: Mus musculus
<220> FEATURE:
<223> OTHER INFORMATION: Peptide sequence of bHLH-PAS gene family member
      MOUSE.EPAS (Genbank Accession No. U81983).

<400> SEQUENCE: 18

Arg Lys Glu Lys Ser Arg Asp Ala Ala Arg Cys Arg Arg Ser Lys
                 5                  10                  15

Glu Thr Glu Val Phe Tyr Glu Leu Ala His Glu Leu Pro Leu Pro
                20                  25                  30

His Ser Val Ser Ser His Leu Asp Lys Ala Ser Ile Met Arg Leu
                35                  40                  45

Ala Ile Ser Phe Leu
                50

<210> SEQ ID NO 19
<211> LENGTH: 50
<212> TYPE: PRT
<213> ORGANISM: Mus musculus
<220> FEATURE:
<223> OTHER INFORMATION: Peptide sequence of bHLH-PAS gene family member
      MOUSE.AHR (Genbank Accession No. M94623).

<400> SEQUENCE: 19

Ala Glu Gly Ile Lys Ser Asn Pro Ser Lys Arg His Arg Asp Arg
                 5                  10                  15

Leu Asn Thr Glu Leu Asp Arg Leu Ala Ser Leu Leu Pro Phe Pro
                20                  25                  30

Gln Asp Val Ile Asn Lys Leu Asp Lys Leu Ser Val Leu Arg Leu
                35                  40                  45

Ser Val Ser Tyr Leu
                50

<210> SEQ ID NO 20
<211> LENGTH: 50
<212> TYPE: PRT
<213> ORGANISM: Homo sapiens
<220> FEATURE:
<223> OTHER INFORMATION: Peptide sequence of bHLH-PAS gene family member
      HUMAN.ARNT (Genbank Accession No. M69238).

<400> SEQUENCE: 20

Ala Arg Glu Asn His Ser Glu Ile Glu Arg Arg Arg Arg Asn Lys
                 5                  10                  15

Met Thr Ala Tyr Ile Thr Glu Leu Ser Asp Met Val Pro Thr Cys
                20                  25                  30

Ser Ala Leu Ala Arg Lys Pro Asp Lys Leu Thr Ile Leu Arg Met
                35                  40                  45

Ala Val Ser His Met
                50

<210> SEQ ID NO 21
<211> LENGTH: 51
<212> TYPE: PRT
```

-continued

```
<213> ORGANISM: Homo sapiens
<220> FEATURE:
<223> OTHER INFORMATION: Peptide sequence of bHLH-PAS gene family member
      RIGUI (Genbank Accession No. AF000998).

<400> SEQUENCE: 21

Ser Gly Cys Ser Ser Glu Gln Ser Ala Arg Ala Arg Thr Gln Lys
                5                  10                  15

Glu Leu Met Thr Ala Leu Arg Glu Leu Lys Leu Arg Leu Pro Pro
               20                  25                  30

Glu Arg Arg Gly Lys Gly Arg Ser Gly Thr Leu Ala Thr Leu Gln
               35                  40                  45

Tyr Ala Leu Ala Cys Val
               50
```

MAMMALIAN CIRCADIAN RHYTHM-LIKE GENE

This Appln claims the benefit for Provisional No. 60/065,957 filed Nov. 4, 1997 and Provisional No. 60/058,256 Sep. 9, 1997.

FEDERAL FUNDING LEGEND

The present invention was created in part using funds from the federal government under Department of Defense grant DAMD 17-94-J-4484. The U.S. government has, therefore, certain rights in this invention.

BACKGROUND OF THE INVENTION

1. Field of the Invention

The present invention relates generally to the fields of molecular genetics and neuroendocrine cellular biology. More specifically, the present invention relates to a mammalian drosophila period-like gene that exhibits properties of a circadian pacemaker.

2. Description of the Related Art

In response to daily environmental cues, the physiology and behavior of all living organisms from bacteria to humans are controlled by circadian rhythms driven by endogenous oscillators (Dunlap, 1993, Takahashi, 1995). Alteration of the circadian rhythm in humans can lead to behavioral changes as typified by jet lag and sleep disorders including those associated with shift work (Arendt and Broadway, 1987, Vignau et al., 1993, Wehr, 1996). In addition, certain pathophysiologies are known to fluctuate according to circadian rhythms such as the increased likelihood of a myocardial infarction occurring in the morning, and winter seasonal affective disorder (Kraft and Martin, 1995, Swaab et al., 1996, Teicher et al., 1997).

Extensive physiological and behavioral studies have determined that the endogenous clock is characterized by a cycle approximately 24 hours in duration. When organisms are placed under invariant environmental conditions, this clock is self-sustaining, similar to a pacemaker. This endogenous clock is further distinguished by its ability to be entrained, i.e., synchronized by environmental cues such as light and temperature cycles (Pittendrigh, 1993, Takahashi, 1995).

Primary culture of suprachiasmatic nucleus (SCN) neurons and suprachiasmatic nucleus ablation and transplantation studies indicate that the circadian clock is cell autonomous, and that in mammals it is located primarily in a part of the hypothalamus known as the suprachiasmatic nucleus, (Ralph et al., 1990, Welsh et al., 1995) and is situated close to the base of the brain. There are independent circadian oscillators located in the retina (Tosini and Menaker, 1996). In constant darkness, the various circadian functions such as maintenance of body temperature, formation of urine, and secretion of cortisol become asynchronous (Aschoff, 1969). This suggests that there may be several independent clocks that each regulate specific circadian rhythms. However, studies of the hamster tau mutant suggest that the molecular components that constitute the various clocks may be related (Tosini and Menaker, 1996).

The molecular mechanisms that constitute these oscillators in mammals are unknown. 2-deoxy [$^{14}$C]-glucose uptake experiments (Schwartz and Gainer, 1977) and studies using protein and RNA synthesis inhibitors suggest that circadian rhythms can be controlled by periodic expression of genes (Takahashi and Turek, 1987, Raju et al., 1991). A mutation in a single gene, clock, alters the phase of the circadian clocks in mice (King et al., 1997). Whether clock is expressed in a periodic pattern is not known.

In Drosophila, two genes period (per) and timeless (tim), are essential components of the circadian clock (Reppert and Sauman, 1995). A heterodimer of Per and Tim proteins is thought to regulate the circadian process by creating a negative feedback loop controlling per and tim expression (Zeng et al., 1996). Two lines of evidence, the oscillatory nature of the per expression, and the phenotype of per mutants, portray the central role of the per gene in the circadian machinery of insects (Konopka and Benzer, 1971, Citri et al., 1987, Hardin et al., 1990, Hall, 1996). Immunohistochemical analysis of rat brain using a Drosophila Per antibody revealed staining in the suprachiasmatic nucleus, suggesting the possibility of a conserved mammalian Per protein (Siwicki et al., 1992). However, in over a decade since per was first isolated from *Drosophila melanogaster* (Bargellow et al., 1984; Citri et al., 1987), no mammalian per homologue has yet been reported.

The prior art is deficient in the lack of a mammalian ortholog to the drosophila period gene that exhibits properties of a circadian pacemaker. The present invention fulfills this longstanding need and desire in the art.

SUMMARY OF THE INVENTION

The molecular components of mammalian circadian clocks were previously unknown. The present invention demonstrates the isolation of a human gene termed RIGUI that encodes a basic-helix-loop-helix motif/PAS protein 44% homologous (identical amino acids, conservative and neutral substitutions) to *Drosophila period*. The highly conserved mouse homolog (m-rigui) is expressed in a circadian pattern in the suprachiasmatic nucleus (SCN), the neuroanotomical site of circadian regulation in mammals. Circadian expression in the suprachiasmatic nucleus continues in constant darkness, and a shift in the light/dark cycle evokes a proportional shift of m-rigui expression in the suprachiasmatic nucleus. m-rigui transcripts also appear in a circadian pattern in Purkinje neurons, pars tuberalis, and retina, but with a timing of oscillation different from that seen in the suprachiasmatic nucleus. Sequence homology and circadian patterns of expression suggest that RIGUI is a mammalian ortholog of the *Drosophila period* gene, raising the possibility that a regulator of circadian clocks is conserved.

In one embodiment of the present invention, there is provided a DNA encoding a RIGUI protein selected from the group consisting of: (a) isolated DNA which encodes a RIGUI protein; (b) isolated DNA which hybridizes to isolated DNA of (a) above and which encodes a RIGUI protein; and (c) isolated DNA differing from the isolated DNAs of (a) and (b) above in codon sequence due to the degeneracy of the genetic code, and which encodes a RIGUI protein.

In another embodiment of the present invention, there is provided a vector capable of expressing the DNA of the present invention adapted for expression in a recombinant cell and regulatory elements necessary for expression of the DNA in the cell.

In yet another embodiment of the present invention, there is provided a host cell transfected with the vector of the present invention, said vector expressing a RIGUI protein.

In still yet another embodiment of the present invention, there is provided a method of detecting expression of the protein of claim 1, comprising the steps of: (a) contacting mRNA obtained from a cell with a labeled hybridization probe; and (b) detecting hybridization of the probe with the mRNA.

Other and further aspects, features, and advantages of the present invention will be apparent from the following description of the presently preferred embodiments of the invention given for the purpose of disclosure.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A shows the fluorescence in situ hybridization (FISH) mapping of a cosmid 39C2 (LA17NC01) containing the RIGUI gene to human metaphase chromosomes. The gene maps is located on the short arm of chromosome 17. FIG. 1B shows the structure of three RIGUI isoforms deduced from extensive screening of a human heart cDNA library. The three isoforms were identical in regions indicated by the same hue/shading. The proteins diverge in their C-terminal portion. The blue box indicates a putative basic-helix-loop-helix motif and the pink box represents the PAS domain with the two characteristic repeats A and B. Thick lines in RIGUI 6.6 3' untranslated regions (UTR) represent sequences not present in the RIGUI 3.0 and RIGUI 4.7 variants. FIG. 1C shows a Northern blot of human heart muscle RNA probed with the RIGUI cDNA. Note the transcripts at 4.7 and 6.6 kb, possibly representing RIGUI 4.7 and RIGUI 6.6 cDNAs shown in FIG. 1B. FIG. 1D shows the Northern analysis of adult of adult mouse tissues. Transcript sizes (arrows) are similar to those seen in humans.

FIG. 3 shows an alignment of the basic-helix-loop-helix (bHLH) motif of RIGUI and other PAS domain genes. The amino acid sequence alignment of the basic-helix-loop-helix motif of RIGUI and 8 other members of the bHLH-PAS gene family was undertaken. The consensus amino (SEQ ID NO: 12) represent identical residues observed in greater than 50% of the proteins listed. Amino acid residue conserved in RIGUI (SEQ ID NO: 21) are colored. The peptide sequences for the various bHLH-PAS were obtained from Genbank. Accession numbers for proteins listed are as follows: NPAS2 (U77969); clock (AF000998) (SEQ ID NO: 14); Drosophila TRH (U42699) (SEQ ID NO: 15); Mouse SIM1 (D79209) (SEQ ID NO: 16); Human HIFa (U22431) (SEQ ID NO: 17); Mouse EPAS1 (U81983) (SEQ ID NO: 18); Mouse AHR (M94623) (SEQ ID NO: 19) and Human ARNT (M69238) (SEQ ID NO: 20).

FIG. 5A shows the high levels of expression of m-rigui in the suprachiasmatic nucleus at circadian time ZT6. FIG. 5B shows that at CT18, expression of m-rigui is no longer detected. FIG. 5C shows the expression of m-rigui in the pars tuberalis is high at ZT24. The pars tuberalis is a sheet of tissue surrounding the median eminence. FIG. 5D shows that by ZT12, expression of m-rigui in the pars tuberalis is greatly reduced. Note weak expression in the lateral infundibular recess. FIGS. 5E and 5F shows that the m-rigui is persistently expressed in the internal granular layer of the cerebellum. In contrast, Purkinje neurons express m-rigui in a circadian pattern with strong expression at ZT12. FIGS. 5G and 5H shows the absence of expression of m-rigui in the pars tuberalis of C57BL/6 mice. FIG. 5I shows the expression of m-rigui in the hippocampus and piriform cortex (FIG. 5J) is constitutive. FIGS. 5K and 5L shows the expression of the mouse clock gene in the suprachiasmatic nucleus is constitutive. FIG. 5M shows the diagram illustrating plane and location of sections displayed in FIG. 5A to FIG. 5L. Abbreviations: CA, cornu ammonis; DG, dendate gyrus, IGL, internal granular layer; LIR, lateral infundibular recess; ME, median eminence, P, Purkinje neurons; PFC, piriform cortex; PT, pars tuberalis; suprachiasmatic nucleus, suprachiasmatic nucleus. Scale bars correspond to 500 μm in all figures except (C, D, G, and H), where the bars are equivalent to 300 μm.

FIGS. 7A–7D shows the suprachiasmatic nucleus of a reference animal kept in the standard 12 hours light/12 hours dark cycle (symbolized by the vertical bar to the left). Note maximal expression at ZT6 (panel D). FIGS. 7E–7H show the animals sacrificed 3 days following the 6 hours shift of the 12 hours light/12 hours dark cycle (symbolized by the vertical bar to the right). High expression is now seen in panels (G) and (H) indicating an initiation of a phase shift in m-rigui expression. FIGS. 7I–7L show the animals sacrificed 8 days following the 6 hours shift of the 12 hours light/12 hours dark cycle. High expression is now seen only in panel (K) indicating a completion of the entrainment of m-rigui expression and acquisition of the new day/night cycle. For abbreviations, see FIGS. 5A–5M. Scale bar corresponds to 500 μm.

DETAILED DESCRIPTION OF THE INVENTION

Figure 1A:
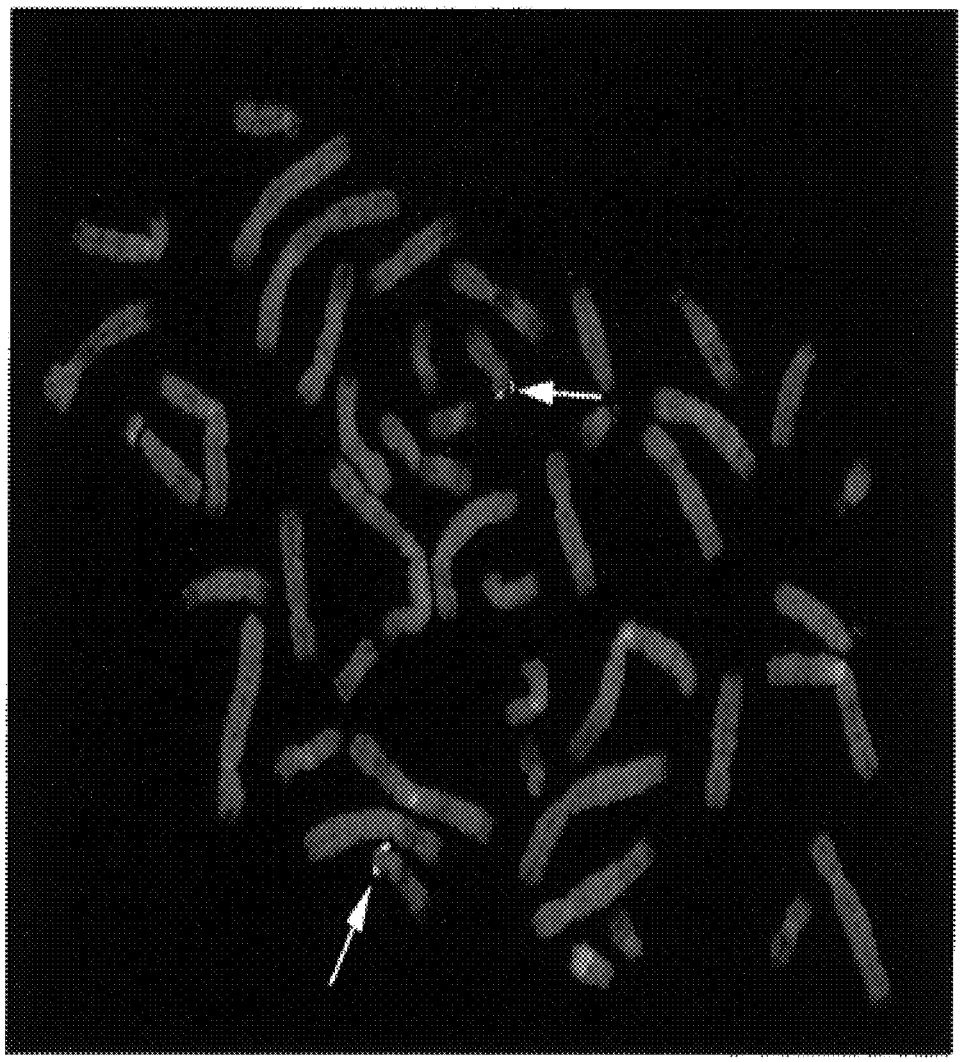
FIGS. 1A–1D show the characterization of the human RIGUI gene.

The present invention describes the identification of a putative mammalian per ortholog designated as RIGUI (named after an ancient Chinese sundial). In the mouse, this gene exhibits striking circadian changes of expression in the retina, the suprachiasmatic nucleus, the pars tuberalis of the median eminence, and in the Purkinje cells of the cerebellum. As expected for a pacemaker gene, RIGUI oscillation is maintained under constant darkness. The cycle of oscillation can be entrained upon shifting the light/dark setting. Remarkably, RIGUI expression in the pars tuberalis, the retina, the Purkinje cells and suprachiasmatic nucleus is not in phase, indicating that expression in these tissues oscillates in a tissue-autonomous fashion. Taken together, the present invention suggest that RIGUI is a mammalian ortholog of the *Drosophila period* gene, and that a key regulator of circadian rhythms is thus conserved during evolution.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomeclature, abbreviations for amino acid residues are shown below:

TABLE OF CORRESPONDENCE

| SYMBOL 1-Letter | 3-Letter | AMINO ACID |
|---|---|---|
| Y | Tyr | tyrosine |
| G | Gly | glycine |
| F | Phe | Phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

A "nucleotide polymorphism" refers to changes in nucleotides(s) that does not affect the encoded amino acids or if it leads to a change in an encoded amino, it has a neutral effects.

An "exon" is an expressed sequence transcribed from the gene locus.

An "intron" is a non-expressed sequence that is from the gene locus.

A "cis-element" is a nucleotide sequence that encompasses the gene locus that interacts with other proteins which can upregulate or downregulate expression of a specific gene locus.

A "gene locus" is a region of the genome that encodes for a specific gene. The term "gene locus" includes the promoter, cis-elements, and exon and intron sequences that embody the messenger RNA.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

A "homodimer" refers to the expressed protein product dimerized to form a functional molecule.

A "heterodimer" refers to an expressed protein that forms a functional molecule with another protein.

A "protein bait" is a bait in a protein sequence that is encoded in part, or in whole by the gene locus which is used in an expression system like the "two-hybrid system" used in vivo to search the "protein-protein" interactions.

The term "induction of gene expression" refers to the induction of the gene by environmental cues, such as light, temperature, social/behavior activities and the use of hormones such as melatonin.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantity of both the label after which binding studies are conducted to determine the extent to which the labeled material binds to the cell receptors. In this way, differences in affinity between materials can be ascertained.

Another assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

As used herein, the term "host" is meant to include not only prokaryotes but also eukaryotes such as yeast, plant and animal cells. A recombinant DNA molecule or gene which encodes a human or mouse RIGUI proteins of the present invention can be used to transform a host using any of the techniques commonly known to those of ordinary skill in the art. Especially preferred is the use of a vector containing coding sequences for the gene which encodes a human or mouse RIGUI protein of the present invention for purposes of prokaryote transformation. Prokaryotic hosts may include *E. Coli, S. tymphimurium, Serratia marcescens* and *Bacillus subtilis*. Eukaryotic hosts include yeasts such as *Pichia pastoris,* mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

The invention includes a substantially pure DNA encoding a human or mouse RIGUI protein, a strand of which DNA will hybridize at high stringency to a probe containing a sequence of at least 15 consecutive nucleotides of SEQ ID Nos: 6, 7, 8 and 10. The protein encoded by the DNA of this invention may share at least 80% sequence identity (preferably 85%, more preferably 90%, and most preferably 95%) with the amino acids listed in SEQ ID Nos: 6, 7, 8 and 10).

The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in SEQ ID Nos: 3, 4, 5 and 9) or the complement thereof. Such a probe is useful for detecting expression of RIGUI in a human cell by a method including the steps of (a) contacting mRNA obtained from the cell with the labeled hybridization probe; and (b) detecting hybridization of the probe with the mRNA.

This invention also includes a substantially pure DNA containing a sequence of at least 15 consecutive nucleotides (preferably 20, more preferably 30, even more preferably 50, and most preferably all) of the region from the nucleotides listed in SEQ ID NO: 3, 4, 5 and 9.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in SEQ ID Nos: 3, 4, 5 and 9) which encodes an alternative splice variant of RIGUI.

The DNA may have at least about 70% sequence identity to the coding sequence of the nucleotides listed in SEQ ID Nos: 3, 4, 5 and 9, preferably at least 75% (e.g. at least 80%); and most preferably at least 90%. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The present invention comprises a vector comprising a DNA sequence which encodes a RIGUI protein and said vector is capable of replication in a host which comprises, in operable linkage: a) an origin of replication; b) a promoter; and c) a DNA sequence coding for said protein. Preferably, the vector of the present invention contains a portion of the DNA sequence shown in SEQ ID Nos: 3, 4, 5 and 9. A "vector" may be defined as a replicable nucleic acid construct, e.g., a plasmid or viral nucleic acid. Vectors may be used to amplify and/or express nucleic acid encoding a RIGUI protein. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

By a "substantially pure protein" is meant a protein which has been separated from at least some of those components which naturally accompany it. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure RIGUI protein may be obtained, for example, by extraction from a natural source; by expression of a recombinant nucleic acid encoding an RIGUI polypeptide; or by chemically synthesizing the protein.

Purity can be measured by any appropriate method, e.g., column chromatography such as immunoaffinity chromatography using an antibody specific for RIGUI, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments (e.g., antigenic fragments) of the RIGUI protein. As used herein, "fragment," as applied to a polypeptide, will ordinarily be at least 10 residues, more typically at least 20 residues, and preferably at least 30 (e.g., 50) residues in length, but less than the entire, intact sequence. Fragments of the RIGUI protein can be generated by methods known to those skilled in the art, e.g., by enzymatic digestion of naturally occurring or recombinant RIGUI protein, by recombinant DNA techniques using an expression vector that encodes a defined fragment of RIGUI, or by chemical synthesis. The ability of a candidate fragment to exhibit a characteristic of RIGUI (e.g., binding to an antibody specific for RIGUI) can be assessed by methods described herein. Purified RIGUI or antigenic fragments of RIGUI can be used to generate new antibodies or to test existing antibodies (e.g., as positive controls in a diagnostic assay) by employing standard protocols known to those skilled in the art. Included in this invention are polyclonal antisera generated by using RIGUI or a fragment of RIGUI as the immunogen in, e.g., rabbits. Standard protocols for monoclonal and polyclonal antibody production known to those skilled in this art are employed. The monoclonal antibodies generated by this procedure can be screened for the ability to identify recombinant RIGUI cDNA clones, and to distinguish them from known cDNA clones.

Further included in this invention are RIGUI proteins which are encoded at least in part by portions of SEQ ID NO: SEQ ID Nos: 3, 4, 5 and 9, e.g., products of alternative mRNA splicing or alternative protein processing events, or in which a section of RIGUI sequence has been deleted. The fragment, or the intact RIGUI polypeptide, may be covalently linked to another polypeptide, e.g. which acts as a label, a ligand or a means to increase antigenicity.

The invention also includes a polyclonal or monoclonal antibody which specifically binds to RIGUI. The invention encompasses not only an intact monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin.

In one embodiment, the antibody, or a fragment thereof, may be linked to a toxin or to a detectable label, e.g. a radioactive label, non-radioactive isotopic label, fluorescent label, chemiluminescent label, paramagnetic label, enzyme label, or calorimetric label. Examples of suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^3H$, $^{125}I$, $^{131}I$, $^{32}P$, $^{35}S$, $^{14}C$, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) *JACC* 14, 472–480; Shreve et al., (1986) *Magn. Reson. Med.* 3, 336–340; Wolf, G. L., (1984) *Physiol. Chem. Phys. Med. NMR* 16, 93–95; Wesbey et al., (1984) *Physiol. Chem. Phys. Med. NMR* 16, 145–155; Runge et al., (1984) *Invest. Radiol.* 19, 408–415. Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al., (1976) *Clin. Chim. Acta* 70, 1–31; and Schurs et al., (1977) *Clin. Chim. Acta* 81, 1–40. Coupling techniques mentioned in the latter are the glutaraldehyde method, the periodate method, the dimaleimide method, the m-maleimidobenzyl-N-hydroxy-succinimide ester method. All of these methods are incorporated by reference herein.

Also within the invention is a method of detecting RIGUI protein in a biological sample, which includes the steps of contacting the sample with the labelled antibody, e.g., radioactively tagged antibody specific for RIGUI, and determining whether the antibody binds to a component of the sample.

A standard Northern blot assay can be used to ascertain the relative amounts of RIGUI mRNA in a cell or tissue obtained from a patient suspected of having cancer, in accordance with conventional Northern hybridization techniques known to those persons of ordinary skill in the art. This Northern assay uses a hybridization probe, e.g. radiolabelled RIGUI cDNA, either containing the full-length, single stranded DNA having a sequence complementary to SEQ ID Nos. 3, 4, 5 or 9, or a fragment of that DNA sequence at least 20 (preferably at least 30, more preferably at least 50, and most preferably at least 100 consecutive nucleotides in length). The DNA hybridization probe can be labelled by any of the many different methods known to those skilled in this art.

The present invention is directed to DNA encoding a RIGUI protein selected from the group consisting of: (a) isolated DNA which encodes a RIGUI protein; (b) isolated DNA which hybridizes to isolated DNA of (a) above and which encodes a RIGUI protein; and (c) isolated DNA differing from the isolated DNAs of (a) and (b) above in codon sequence due to the degeneracy of the genetic code, and which encodes a RIGUI protein. Preferably, the DNA has the sequence shown in SEQ ID Nos. 3, 4, 5 or 9. More preferably, the DNA encodes a RIGUI protein having the amino acid sequence shown in SEQ ID Nos. 6, 7, 8 and 10.

The present invention is also directed to a vector capable of expressing the DNA of the present invention adapted for expression in a recombinant cell and regulatory elements necessary for expression of the DNA in the cell. Preferably, the vector contains DNA encoding a RIGUI protein having the amino acid sequence shown in SEQ ID Nos. 6, 7, 8 and 10.

The present invention is also directed to a host cell transfected with the vector described herein, said vector expressing a RIGUI protein. Representative host cells include consisting of bacterial cells, mammalian cells and insect cells.

The present invention is also directed to a isolated and purified RIGUI protein coded for by DNA selected from the group consisting of: (a) isolated DNA which encodes a RIGUI protein; (b) isolated DNA which hybridizes to isolated DNA of (a) above and which encodes a RIGUI protein; and (c) isolated DNA differing from the isolated DNAs of (a) and (b) above in codon sequence due to the degeneracy of the genetic code, and which encodes a RIGUI protein. Preferably, the isolated and purified RIGUI protein has the amino acid sequence shown in SEQ ID Nos. 6, 7, 8 and 10.

The present invention is also directed to a method of detecting expression of the RIGUI protein, comprising the steps of: (a) contacting mRNA obtained from the cell with the labeled hybridization probe; and (b) detecting hybridization of the probe with the mRNA. Preferably, the probe consists of a portion of the DNA of SEQ ID Nos. 3, 4, 5 and 9.

The following examples are given for the purpose of illustrating various embodiments of the invention and are not meant to limit the present invention in any fashion.

EXAMPLE 1

Mapping studies by FISH and STS-PCR

Fluorescence in situ hybridization (FISH) mapping of a 39C2 cosmid on metaphase chromosomes was conducted essentially as described (Ijdo et al., 1992). STS-PCR mapping of RIGUI was carried out the Corriel mapping panel #2 using the following primers 5'-CTCCCATCTGGGGAGGAGGT-3' (SEQ ID No: 1) and 5'-GGACCATCTCCAGGAGTCCA-3' (SEQ ID No: 2) with methods as previously described (Lee et al., 1995).

EXAMPLE 2

Screening of cDNA library

The cDNA for RIGUI was isolated by reciprocal probing (Lee et al., 1995) of an arrayed human heart cDNA library with the LA17NC01 chromosome 17 cosmid library (Kallioniemi et al., 1994). This approach results in the simultaneous identification of genomic cosmid clones associated with a particular cDNA. The full-length cDNA for RIGUI and m-rigui was identified from a human heart and a mouse brain cDNA library (BRL-GIBCO), respectively. Radiolabeled probes generated from RIGUI cDNA fragments were used to screen the appropriate cDNA library using standard laboratory protocols (Sambrook et al., 1989). Both strands of the nucleotide sequence of the RIGUI and m-rigui cDNA were determined using a DNA sequencing reaction kit and an ABI 373A instrument.

EXAMPLE 3

RNase Protection Assay

Six adult mice were sacrificed at four hour intervals. The eyes and brains were dissected and immediately homogenized in 4M guanidinium isothiocyanate solution. Total RNA were isolated by CsCl ultracentrifugation as described (Chirgwin et al., 1979).

The m-rigui probe, a 280 base pair fragment between the restriction enzyme PstI site at nucleotide position 722 and the SacI site at position 995, was subcloned into pBluescript II vector. This plasmid was linearized with EcoRI and a radiolabeled antisense probe was generated by T3 RNA polymerase with [$^{32}$P]CTP using a kit purchased from Promega. The 316 base pair internal control GAPDH probe (Ambion) was generated using the same procedure except that the ratio of the cold to hot CTP was increased by 50 fold compared to the m-rigui probe. All the riboprobes were purified by gel electrophoresis and eluted in RNase free elution buffer (Ambion). For each time point, 20 mg of RNA was hybridized to 5×10$^4$ cpm of each riboprobes under the following conditions; 0.75 M NaCl, 0.075 M sodium citrate, and 0.05 tris(HCl) pH 7.0 at 65° C. for 16 hours. On completion of hybridization, the reaction mixtures were treated according the procedure of the RNAse protection kit purchased from Boehringer-Mannheim.

EXAMPLE 4
Specimen preparation and histology

The 129SvEvBra and C57BL/6J mouse strains were provided by Dr. Allan Bradley of Baylor College of Medicine. All animals were kept in separate cages under the condition of 12 hours light and 12 hours dark cycles for at least two weeks prior to their use in the respective experiments. For free-running condition, the mice were maintained in a room with lights completely turned off. Both the 12 hour light/12 dark cycle and entrainment experiments were carried out as stated above. Mice were sacrificed by cervical dislocation and the brain was removed, fixed in ice-cold 4% paraformaldehyde for 16 to 20 hours. Tissue was dehydrated and embedded in paraffin and sectioned at a thickness of 7 μm. Animals collected under dark conditions were dissected under a 15 W safety red light.

EXAMPLE 5
RNA in situ hybridization

In situ hybridization was carried out as described (Albrecht et al., 1997). Antisense and sense riboprobes were synthesized with T3 or T7 RNA polymerase in the presence of a $^{35}$S-UTP (1,250 Ci/mmol, Du Pont NEN, Charlotte, N.C.). The m-rigui probe was made from a cDNA corresponding to nucleotides 620 to 1164. Two different clock probes were obtained from clones generated by PCR amplification of oligo-dT primed mouse brain cDNA. Probe 1 encompassed nucleotide 1352 to 2080 of the coding region, and probe 2 encompassed nucleotide 6331 to 7122 in the 3' UTR (Genbank accession Number AF000998). Radiolabeled antisense and sense RNA probes were generated with T3 or T7 RNA polymerases. Hybridization was done overnight at 55° C. (m-rigui and both clock. Stringency washes were performed at 64° C. (m-rigui), 65° C. (coding region probe for clock), and 63.5 (3' UTR region probe for clock). Slides were dipped in NTB-2 emulsion and exposed for 6 to 10 days. Tissue was visualized by fluorescence of Hoechst dye-stained nuclei (blue color in figures). Silver grains (appear red in figures) were visualized by dark-field illumination. Images are videographs captured with Adobe Photoshop.

EXAMPLE 6
Isolation and characterization of RIGUI transcripts

A partial cDNA for human RIGUI was obtained to identify human chromosome 17 specific transcripts (Lee et al., 1995). Out of 104 cDNAs identified this way, five were selected for further study. The deduced amino acid sequences of these five partial cDNAs indicated some degree of sequence homology to regulatory proteins (Sun et al., 1996). The sequence of one of the five cDNAs later revealed the presence of a basic helix-loop-helix motif and a Per-ARNT-Sim (PAS) domain (see below). This clone was referred to as RIGUI and maps to human chromosome 17p12 (FIG. 1A).

Figure 1B:
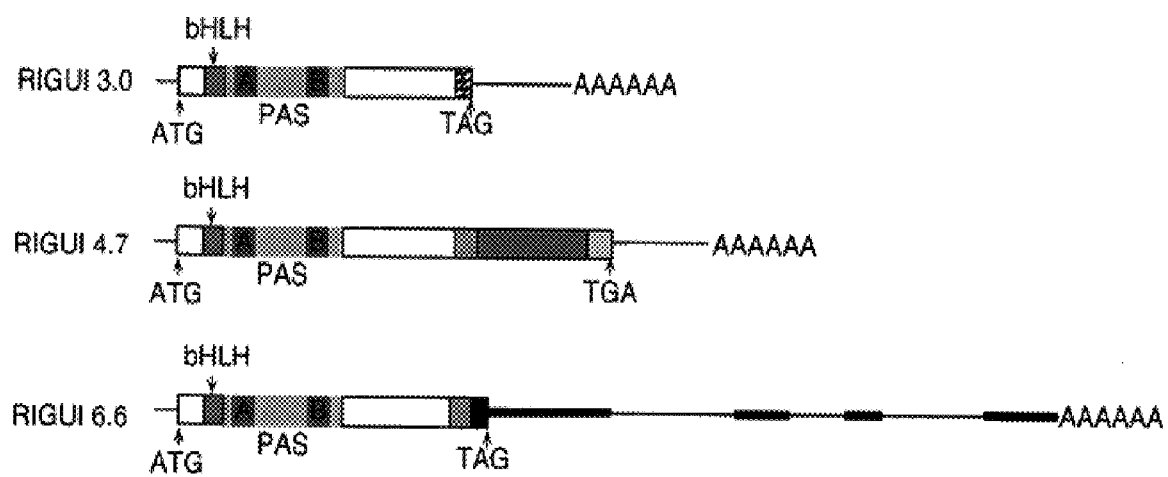
Figure 1C:
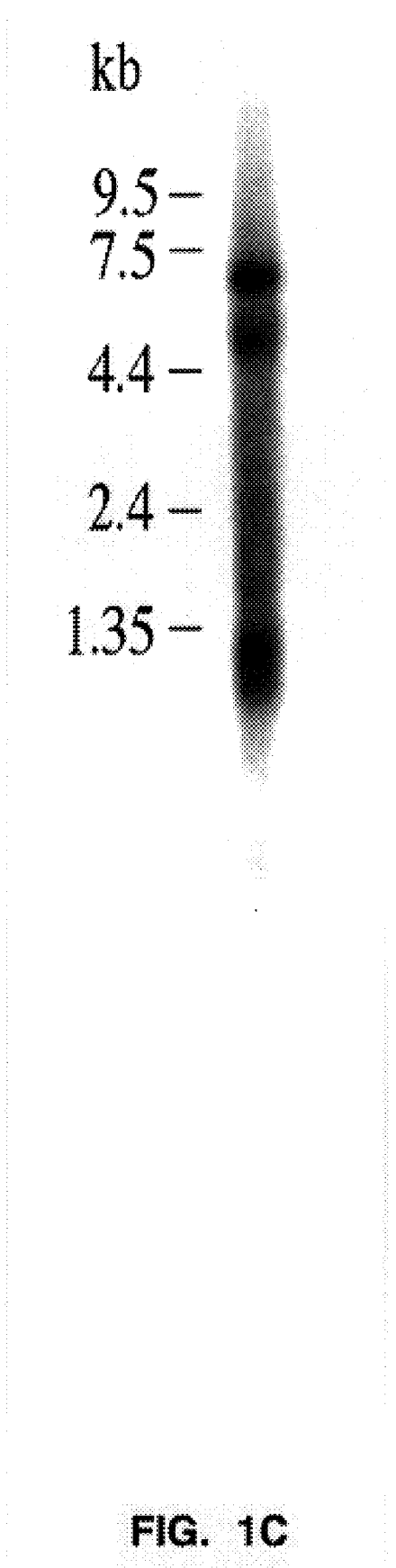
Figure 1D:
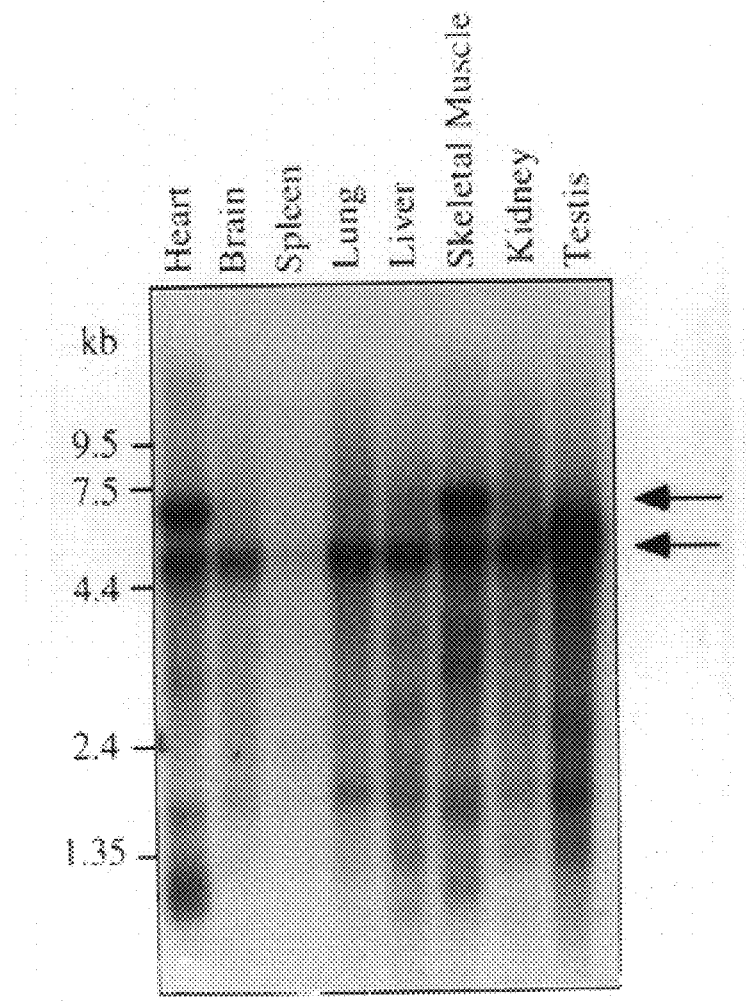

Using a 0.9 kb probe, derived from the partial cDNA isolated initially, fifteen cDNA clones were isolated from a human heart muscle cDNA library. Ten clones ranged in length between 3 and 4.7 kb and based on their DNA sequences, represent the RIGUI 4.7 transcript (FIG. 1B). Northern blots display a band at 4.7 kb possibly representing the 4.7 kb cDNA (FIG. 1C) although a prominent larger species was also observed (see below). Three of fifteen clones had high sequence homology to the 3' region of RIGUI 4.7, but contained three segments inserted between the regions of homology (FIG. 1B, RIGUI 6.6). Combining these partial cDNAs with the RIGUI 4.7 sequence can account for the 6.6 kb band detected in the Northern blot (FIG. 1C). The two remaining clones were 3.0 kb in length and sequences from their 5' and 3' regions were identical to the corresponding 3' and 5' region of the RIGUI 4.7 transcript, but the clones were shorter due to an alternate splicing event. Although several RIGUI transcripts were isolated, the fluorescence in situ hybridization studies (FIG. 1A) and genomic-PCR experiments (data not shown) identify RIGUI as a single locus gene. The three transcripts shown in FIG. 1B result from differential splicing.

TABLE I shows the 6614 nucleotide sequence of the 6.6 kb cDNA of human RIGUI (SEQ ID No:3). TABLE II shows the nucleotide sequence of the 4.7 kb cDNA of human RIGUI (SEQ ID No: b4). TABLE III shows the nucleotide sequence of the 3.0 kb cDNA of human RIGUI (SEQ ID No: 5).

TABLE I

Nucleotide sequence of the 6.6 kb RIGUI cDNA

| | | | | | |
|---|---|---|---|---|---|
| 1 | GGCTGGAGCG | GCGGCGGGCA | GGCGTGCGGA | GGACACTCCT | GCGACCAGGT |
| 51 | ACTGGCTGTG | ATCGAACTTC | TCAACCCTCA | GAGACTTAGA | TCTTCCACCT |
| 101 | CACTCCCTCA | GCCAAGCCTC | CAGGCCCCCT | CGTGCATCCG | TGGTGGCCTC |
| 151 | TCTGCCTTCT | CTGTTCTGTT | CTCCCCATGG | CCCAGACATG | AGTGGCCCCC |
| 201 | TAGAAGGGGC | TGATGGGGGA | GGGGACCCCA | GGCCTGGGGA | ATCATTTTGT |
| 251 | CCTGGGGGCG | TCCCATCCCC | TGGGCCCCCA | CAGCACCGGC | CTTGCCCAGG |
| 301 | CCCCAGCCTG | GCCGATGACA | CCGATGCCAA | CAGCAATGGT | TCAAGTGGCA |

TABLE I-continued

Nucleotide sequence of the 6.6 kb RIGUI cDNA

```
 351 ATGAGTCCAA CGGGCATGAG TCTAGAGGCG CATCTCAGCG GAGCTCACAC
 401 AGCTCCTCCT CAGGCAACGG CAAGGACTCA GCCCTGCTGG AGACCACTGA
 451 GAGCAGCAAG AGCACAAACT CTCAGAGCCC ATCCCCACCC AGCAGTTCCA
 501 TTGCCTACAG CCTCCTGAGT GCCAGCTCAG AGCAGGACAA CCCGTCCACC
 551 AGTGGCTGCA GCAGTGAACA GTCAGCCCGG GCAAGGACTC AGAAGGAACT
 601 CATGACAGCA CTTCGAGAGC TCAAGCTTCG ACTGCCGCCA GAGCGCCGGG
 651 GCAAGGGCCG CTCTGGGACC CTGGCCACGC TGCAGTACGC ACTGGCCTGT
 701 GTCAAGCAGG TGCAGGCCAA CCAGGAATAC TACCAGCAGT GGAGCCTGGA
 751 GGAGGGCGAG CCTTGCTCCA TGGACATGTC CACCTATACC CTGGAGGAGC
 801 TGGAGCACAT CACGTCTGAG TACACACTTC AGAACCAGGA TACCTTCTCA
 851 GTGGCTGTCT CCTTCCTGAC GGGCCGAATC GTCTACATTT CGGAGCAGGC
 901 AGCCGTCCTG CTGCGTTGCA AGCGGGACGT GTTCCGGGGT ACCCGCTTCT
 951 CTGAGCTCCT GGCTCCCCAG GATGTGGGAG TCTTCTATGG TTCCACTGCT
1001 CCATCTCGCC TGCCCACCTG GGGCACAGGG GCCTCAGCAG GTTCAGGCCT
1051 CAGGGACTTT ACCCAGGAGA AGTCCGTCTT CTGCCGTATC AGAGGAGGTC
1101 CTGACCGGGA TCCAGGGCCT CGGTACCAGC CATTCCGCCT AACCCCGTAT
1151 GTGACCAAGA TCCGGGTCTC AGATGGGGCC CCTGCACAGC CGTGCTGCCT
1201 GCTGATTGCA GAGCGCATCC ATTCGGGTTA CGAAGCTCCC CGGATACCCC
1251 CTGACAAGAG GATTTTCACT ACGCGGCACA CACCCAGCTG CCTCTTCCAG
1301 GATGTGGATG AAAGGGCTGC CCCCCTGCTG GGCTACCTGC CCAGGACCT
1351 CCTGGGGGCC CCAGTGCTCC TGTTCCTGCA TCCTGAGGAC CGACCCCTCA
1401 TGCTGGCTAT CCACAAGAAG ATTCTGCAGT TGGCGGGCCA GCCCTTTGAC
1451 CACTCCCCTA TCCGCTTCTG TGCCCGCAAC GGGGAGTATG TCACCATGGA
1501 CACCAGCTGG GCTGGCTTTG TGCACCCCTG GAGCCGCAAG GTAGCCTTCG
1551 TGTTGGGCCG CCACAAAGTA CGCACGGCCC CCTGAATGA GGACGTGTTC
1601 ACTCCCCCGG CCCCCAGCCC AGCTCCCTCC CTGGACACTG ATATCCAGGA
1651 GCTGTCAGAG CAGATCCACC GGCTGCTGCT GCAGCCCGTC ACAGCCCCA
1701 GCCCCACGGG ACTCTGTGGA GTCGGCGCCG TGACATCCCC AGGCCCTCTC
1751 CACAGCCCTG GGTCCTCCAG TGATAGCAAC GGGGGTGATG CAGAGGGGCC
1801 TGGGCCTCCT GCGCCAGTGA CTTTCCAACA GATCTGTAAG GATGTGCATC
1851 TGGTGAAGCA CCAGGGCCAG CAGCTTTTTA TTGAGTCTCG GCCCGGCCT
1901 CAGTCCCGGC CCCGCCTCCC TGCTACAGGC ACGTTCAAGG CCAAGGCCCT
1951 TCCCTGCCAA TCCCCAGACC CAGAGCTGGA GGCGGGTTCT GCTCCCGTCC
2001 AGGCCCCACT AGCCTTGGTC CCTGAGGAGG CCGAGAGGAA AGAAGCCTCC
2051 AGCTGCTCCT ACCAGCAGAT CAACTGCCTG ACAGCATCC TCAGGTACCT
2101 GGAGAGCTGC AACCTCCCCA GCACCACTAA GCGTAAATGT GCCTCCTCCT
2151 CCTCCTATAC CACCTCCTCA GCCTCTGACG ACGACAGGCA GAGGACAGGT
2201 CCAGTCTCTG TGGGGACCAA GAAAGATCCG CCGTCAGCAG CGCTGTCTGG
2251 GGAGGGGGCC ACCCCACGGA AGGAGCCAGT GGTGGGAGGC ACCCTGAGCC
```

TABLE I-continued

Nucleotide sequence of the 6.6 kb RIGUI cDNA

```
2301 CGCTCGCCCT GGCCAATAAG GCGGAGAGTG TGGTGTCCGT CACCAGTCAG
2351 TGTAGCTTCA GCTCCACCAT GCTCCATGTG GGAGACAAGA AGCCCCCGGA
2401 GTCAGACATC ATCATGATGG AGGACCTGCC TGGCCTAGCC CCAGGCCCAG
2451 CCCCCAGCCC AGCCCCCAGC CCCACAGTAG CCCCTGACCC AGCCCCAGAC
2501 GCCTACCGTC CAGTGGGGCT GACCAAGGCC GTGCTGTCCC TGCACACACA
2551 GTGGACTCGA CAGCTCTTCC ACAGCTCCCT CAGCCCTTGG CGAGCGAGGT
2651 AGCCACCTGG GGCCTCCTGG AGCCTGCCCT CTGCCCAGTC TAGGACTGGA
2701 TTGTTGGGGG GTGGGTCTTA AGGGAGGTGT TTCTGCTCCA GGGACCCAGG
2751 CTGGTGTTGC TTCCACCACT AGGCCCTGCC TAGGGACAGG CCCCTCGCTA
2801 GCTTCTCCCC ACTAGGATGG GGTTCCGGGC TGCAGCCAGA GGAGGGCAGC
2851 CTGGGGGGAT GGCACTGGGA TGGGCAGGCA GAGGTGCTGT CTCCAGGTAA
2901 GCGACTTCAG GCCTAGCCTG GGGGCAGGGG CAGGAAGTAT GCCCACTTAG
2951 GAGTCAGTTG TCACTGATGA AGAGACATGC ATAGATTCTG GCCAACTCT
3001 GGGTGGGGTC TGGGCTTCAA GGGCAGGTGG AAGGCAGCCC CTCCAGGTGC
3051 CTGAGGGAGA TCCCCTGCAG GCAGACGCAG GACTCAGGAC TGGGCTTTCC
3101 AGCCCCACTC TTTACTCCAT TGCAAGCTAG GCAGAATACG GCCTCGATGG
3151 GCAGGAGGAA TGCCTAGGCT GGCAGTGCCC ACAGGAGTTT GGCGGACCAG
3201 AGCCATCTGT CCATGTGTCC ATGGACTCAC CCTGCTTCCT CCATCTGCCA
3251 GCATGCCTCC ATCTTCCGCA CACCCCCAGC TCGACCCCTC GTGTAACCTC
3301 TCCCTGGCCT TGTTCCTTTC TCAATAAATC CCCTTGTCCC TGGCTCCTGT
3351 GATTCTTCCC TGAAGGTGCC CCACCTCCTG AGTCCCCCGT TCTGTGTGGG
3401 TTGAGAAGCT CTCTCTGGGA CCTTGGCCTG TCCTCTCCCT GGTCAGCGTG
3451 TCAGGGCAGT GTGGGTAGCA GGGGTACTAA CCCCAGGTTG AGGTCCTTGC
3501 TAACCCTAGT CTCTCCCCAC AGGCTGCCAC CACGGCCCCG CACCCCCAAG
3551 CCGCCGACAC CACTGCCGAT CCAAAGCCAA GCGCTCACGC CACCACCAGA
3601 ACCCTCGGGC TGAAGCGCCC TGCTATGTCT CACACCCCTC ACCCGTGCCA
3651 CCCTCCACCC CCTGGCCCAC CCCACCAGCC ACTACCCCCT TCCCAGCGGT
3701 TGTCCAGCCC TACCCTCTCC CAGTGTTCTC TCCTCGAGGA GGCCCCCAGC
3751 CTCTTCCCCC TGCTCCCACA TCTGTGCCCC CAGCTGCTTT CCCCGCCCCT
3801 TTGGTGACCC CAATGGTGGC CTTGGTGCTC CCTAACTATC TGTTCCCAAC
3851 CCCATCCAGC TATCCTTATG GGGCACTCCA GACCCCTGCT GAAGGGCCTC
3901 CCACTCCTGC CTCGCACTCC CCTTCTCCAT CCTTGCCCGC CCTCCCCCCG
3951 AGTCCTCCTC ACCGCCCGGA CTCTCCACTG TTCAACTCGA GATGCAGCTC
4001 TCCACTCCAG CTCAATCTGC TGCAGCTGGA GGAGCTCCCC CGTGCTGAGG
4051 GGGCTGCTGT TGCAGGAGGC CCTGGGAGCA GTGCCGGGCC CCCACCTCCC
4101 AGTGCGGAGG CTGCTGAGCC AGAGGCCAGA CTGTGAGCAC TGACCCCTGC
4151 GTCTGCCTGC CAGCCCCCAC CCCAGCCCCG CCCCTCTGCC ACCCTGTGCT
4201 GCCTGCTGTC TCTGCCAGGC TGGCGTCTCA GCCTCCAGGA GGTGGAGGGA
```

TABLE I-continued

Nucleotide sequence of the 6.6 kb RIGUI cDNA

```
4251 GTCCCCAGCT GAATTTCTGA ATGAGGCAGA AATTGGCTAC CTCCTCTTTG
4301 AAGGGACAGT CCTGTCTGTC TGACAGGTGG TGAGGACATC TCAATAACTT
4351 CTGAGAGAGC ATCTGTCACT TGGAAAGGGT CTGGCCTCAC ATCCCCACTC
4401 TTCGCCAGCT TTCTTCTCTC TCAGCCTGGC CCTACTGTCA CGAAGTGGGG
4451 AGCAGAGACC ACTGGGGTTG GATGTGCCTC TCCCCACAAC CAGTAAGAGC
4501 AGTTGAAGGG AGGCCTAGGT GCTGACCCCT CCATCCCTCC TTGCCCCCCT
4551 CCCCTCCTCC AGGCGGAGGT CACTGAGTCC TCCAATCAGG ACGCACTTTC
4601 CGGCTCCAGT GACCTGCTCG AACTTCTGCT GCAAGAGGAC TCGCGCTCCG
4651 GCACAGGCTC CGCAGCCTCG GGCTCCTTGG GCTCTGGCTT GGGCTCTGGG
4701 TCTGGTTCAG GCTCCCATGA AGGGGGCAGC ACCTCAGCCA GCATCACTCG
4751 TGAGTACCCC GCCTCCAGCA TCTCCCAGGG TAGGGCAGTG ATTGGGGAGC
4801 CGGGAGCCCA GGCCCCGTCT TGGCGGAGCT TCCTAAGGCC ACTGGGATGG
4851 ACATGTGGCC TTTGAGGGAG GCCTTGTGAG GTCCCAGGAG TGGGCATGCA
4901 GCCGGCCTGA CTCCCATTGG TCTGCCCCCC ACTTCACAGG CAGCAGCCAG
4951 AGCAGCCACA CAAGCAAATA CTTTGGCAGC ATCGACTCTT CCGAGGCTGA
5001 GGCTGGGGCT GCTCGGGGCG GGGCTGAGCC TGGGGACCAG GTGATTAAGT
5051 ACGTGCTCCA GGATCCCATT TGGCTGCTCA TGGCCAATGC TGACCAGCGC
5101 GTCATGATGA CCTACCAGGT GCCCTCCAGG GACATGACCT CTGTGCTGAA
5151 GCAGGATCGG GAGCGGCTCC GAGCCATGCA GAAGCAGCAG CCTCGGTTTT
5201 CTGAGGACCA GCGGCGGGAA CTGGGTGCTG TGCACTCCTG GGTCCGGAAG
5251 GGCCAACTGC CTCGGGCTCT TGATGTGATG GTGAGAGAAG CCTGGGACGG
5301 GGAGAAAAAA GAATTGAGCT CAAGTTCAAG GGGGAGAAAA AAGAATTGAG
5351 CTCAAGTTCA AGGGGGAGAA AAAAGAATTG AGCTCAAGTT CAAGGGATCG
5401 AGGCCAAGAG CTGATCTCCT TGATGTCCTT GGATCATTAA TTCTGAAGAA
5451 TGTTGATTCC ACTAAATTTG CTGTGGATTA TAGAATATTA AGCCGCGTGA
5501 GTCTTTGCAG AACTTTTCAC AGCCTATCCT ATGCTAATAT GCATTGTGAC
5551 TGTCCTGTAA CGGCATCTGG GTAGAGGGCA CAAGGCACTG TCCAACCTTG
5601 TTGGACCGCA GGTGCATCTG TGTGGACTGG TGCTTCTTGG GAGTACATTT
5651 CGGGAAGCAC AGTGGGCTGG GGTGGGAAG CTGCGCTGGC AGGTTAGCAG
5701 TGAGAACCCT GTCTGACTCT CTCATGTCCA TTTCTCTCAC CAAGGCCTGT
5751 GTGGACTGTG GGAGCAGCAC CCAAGATCCT GGTCACCCTG ATGACCCACT
5801 CTTCTCAGAG CTGGATGGAC TGGGGCTGGA GCCCATGGAA GAGGGTGGAG
5851 GCGAGCAGGG CAGCAGCGGT GGCGGCAGTG GTGAGGGAGA GGGCTGCGAG
5901 GAGGCCCAAG GCGGGGCCAA GGCTTCAAGC TCTCAGGACT TGGCTATGGA
5951 GGAGGAGGAA GAAGCAGGAG CTCATCCAGT CCAGCCTTAC CTACAGCAGG
6001 AAACTGCACC AGCTAGACTC CATTCTGGGA CCATCTCCAG GAGTCCATGA
6051 GAGGCTTTCT TCTCCTATGT CCCAATTCTC AGAACTCAGA TGTGGCTAGA
6101 CCAACCAGTG GGAAACTGCC CCAGCTTCTC CCACCATAGG GGGCCGGACC
6151 CCCATCACCA GCCTAGGATC CAGGGGCTGC CTCTGGCCTC TTAGGGAGCA
```

TABLE I-continued

Nucleotide sequence of the 6.6 kb RIGUI cDNA

```
6201 GAGAGCAGAA CTCCGCAGCC CAGCCCAGAG GAGTGTCACC TCCCACCTTT
6251 GGAGAGGAAT CCTTCCCTCC CCTGGACAAA GTTGCTGACA AGCTGCTGAA
6301 GTGGCCTCTC CATATTCCAG CTGAGCCTGA ATCTGACTCT TGAGGGTTGG
6351 GGCTGCACTT ATTTATTGCG GGGAGACAGC TCTCTCTCCC ACCTCCTCCC
6401 CAGATGGGAG GAGAGCCTGA GGCCCAAGCA GGACCCGGGG GTTCCAGCCC
6451 CTAGCTGCTC TGGAGTGGGG GAGGTTGGTG GACCATGGAG TCCCTGGTGC
6501 TGCCCCTCAG GTGGGACCCA GGGGTTCTCA GCTGTACCCT CTGCCGATGG
6551 CATTTGTGTT TTTGATATTT GTGTCTGTTA CTACTTTTTT AATACAAAAA
6601 GATAAAAACG CCAA
```

TABLE II

Nucleotide sequence of the 4.7 kb RIGUI cDNA

```
   1 GGCTGGAGCG GCGGCGGGCA GGCGTGCGGA GGACACTCCT GCGACCAGGT
  51 ACTGGCTGTG ATCGAACTTC TCAACCCTCA GAGACTTAGA TCTTCCACCT
 101 CACTCCCTCA GCCAAGCCTC CAGGCCCCCT CGTGCATCCG TGGTGGCCTC
 151 TCTGCCTTCT CTGTTCTGTT CTCCCCATGG CCCAGACATG AGTGGCCCCC
 201 TAGAAGGGGC TGATGGGGGA GGGGACCCCA GGCCTGGGGA ATCATTTTGT
 251 CCTGGGGGCG TCCCATCCCC TGGGCCCCCA CAGCACCGGC CTTGCCCAGG
 301 CCCCAGCCTG GCCGATGACA CCGATGCCAA CAGCAATGGT TCAAGTGGCA
 351 ATGAGTCCAA CGGGCATGAG TCTAGAGGCG CATCTCAGCG GAGCTCACAC
 401 AGCTCCTCCT CAGGCAACGG CAAGGACTCA GCCCTGCTGG AGACCACTGA
 451 GAGCAGCAAG AGCACAAACT CTCAGAGCCC ATCCCCACCC AGCAGTTCCA
 501 TTGCCTACAG CCTCCTGAGT GCCAGCTCAG AGCAGGACAA CCCGTCCACC
 551 AGTGGCTGCA GCAGTGAACA GTCAGCCCGG GCAAGGACTC AGAAGGAACT
 601 CATGACAGCA CTTCGAGAGC TCAAGCTTCG ACTGCCGCCA GAGCGCCGGG
 651 GCAAGGGCCG CTCTGGGACC CTGGCCACGC TGCAGTACGC ACTGGCCTGT
 701 GTCAAGCAGG TGCAGGCCAA CCAGGAATAC TACCAGCAGT GGAGCCTGGA
 751 GGAGGGCGAG CCTTGCTCCA TGGACATGTC CACCTATACC CTGGAGGAGC
 801 TGGAGCACAT CACGTCTGAG TACACACTTC AGAACCAGGA TACCTTCTCA
 851 GTGGCTGTCT CCTTCCTGAC GGGCCGAATC GTCTACATTT CGGAGCAGGC
 901 AGCCGTCCTG CTGCGTTGCA AGCGGGACGT GTTCCGGGGT ACCCGCTTCT
 951 CTGAGCTCCT GGCTCCCCAG GATGTGGGAG TCTTCTATGG TTCCACTGCT
1001 CCATCTCGCC TGCCCACCTG GGGCACAGGG GCCTCAGCAG GTTCAGGCCT
1051 CAGGGACTTT ACCCAGGAGA AGTCCGTCTT CTGCCGTATC AGAGGAGGTC
1101 CTGACCGGGA TCCAGGGCCT CGGTACCAGC CATTCCGCCT AACCCCGTAT
1151 GTGACCAAGA TCCGGGTCTC AGATGGGGCC CCTGCACAGC CGTGCTGCCT
1201 GCTGATTGCA GAGCGCATCC ATTCGGGTTA CGAAGCTCCC CGGATACCCC
1251 CTGACAAGAG GATTTTCACT ACGCGGCACA CACCCAGCTG CCTCTTCCAG
```

TABLE II-continued

Nucleotide sequence of the 4.7 kb RIGUI cDNA

```
1301 GATGTGGATG AAAGGGCTGC CCCCCTGCTG GGCTACCTGC CCCAGGACCT
1351 CCTGGGGGCC CCAGTGCTCC TGTTCCTGCA TCCTGAGGAC CGACCCCTCA
1401 TGCTGGCTAT CCACAAGAAG ATTCTGCAGT TGGCGGGCCA GCCCTTTGAC
1451 CACTCCCCTA TCCGCTTCTG TGCCCGCAAC GGGGAGTATG TCACCATGGA
1501 CACCAGCTGG GCTGGCTTTG TGCACCCCTG GAGCCGCAAG GTAGCCTTCG
1551 TGTTGGGCCG CCACAAAGTA CGCACGGCCC CCCTGAATGA GGACGTGTTC
1601 ACTCCCCCGG CCCCCAGCCC AGCTCCCTCC CTGGACACTG ATATCCAGGA
1651 GCTGTCAGAG CAGATCCACC GGCTGCTGCT GCAGCCCGTC ACAGCCCCA
1701 GCCCCACGGG ACTCTGTGGA GTCGGCGCCG TGACATCCCC AGGCCCTCTC
1751 CACAGCCCTG GGTCCTCCAG TGATAGCAAC GGGGGTGATG CAGAGGGGCC
1801 TGGGCCTCCT GCGCCAGTGA CTTTCCAACA GATCTGTAAG GATGTGCATC
1851 TGGTGAAGCA CCAGGGCCAG CAGCTTTTTA TTGAGTCTCG GGCCCGGCCT
1901 CAGTCCCGGC CCCGCCTCCC TGCTACAGGC ACGTTCAAGG CCAAGGCCCT
1951 TCCCTGCCAA TCCCCAGACC CAGAGCTGGA GGCGGGTYCT GCTCCCGTCC
2001 AGGCCCCACT AGCCTTGGTC CCTGAGGAGG CCGAGAGGAA AGAAGCCTCC
2051 AGCTGCTCCT ACCAGCAGAT CAACTGCCTG ACAGCATCC TCAGGTACCT
2101 GGAGAGCTGC AACCTCCCCA GCACCACTAA GCGTAAATGT GCCTCCTCCT
2151 CCTCCTATAC CACCTCCTCA GCCTCTGACG ACGACAGGCA GAGGACAGGT
2201 CCAGTCTCTG TGGGACCAA GAAAGATCCG CCGTCAGCAG CGCTGTCTGG
2251 GGAGGGGCC ACCCCACGGA AGGAGCCAGT GGTGGGAGGC ACCCTGAGCC
2301 CGCTCGCCCT GGCCAATAAG GCGGAGAGTG TGGTGTCCGT CACCAGTCAG
2351 TGTAGCTTCA GCTCCACCAT CGTCCATGTG GGAGACAAGA AGCCCCCGGA
2401 GTCGGACATC ATCATGATGG AGGACCTGCC TGGTCTAGCC CCAGGCCCAG
2451 CCCCCAGCCC AGCCCCCAGC CCACAGTAG CCCCTGACCC AGCCCCAGAC
2501 GCCTACCGTC CAGTGGGGCT GACCAAGGCC GTGCTGTCCC TGCACACGCA
2551 GAAGGAAGAG CAAGCCTTCC TCAGCCGCTT CCGAGACCTG GGCAGGCTGC
2601 GTGGACTCGA CAGCTCTTCC ACAGCTCCCT CAGCCCTTGG CGAGCGAGGC
2651 TGCCACCACG GCCCCGCACC CCCAAGCCGC CGACACCACT GCCGATCCAA
2701 AGCCAAGCGC TCACGCCACC ACCAGAACCC TCGGGCTGAA GCGCCCTGCT
2751 ATGTCTCACA CCCCTCACCC GTGCCACCCT CCACCCCCTG CCCACCCCA
2801 CCAGCCACTA CCCCCTTCCC AGCGGTTGTC CAGCCCTACC CTCTCCCAGT
2851 GTTCTCTCCT CGAGGAGGCC CCCAGCCTCT TCCCCCTGCT CCCACATCTG
2901 TGCCCCCAGC TGCTTTCCCC GCCCCTTTGG TGACCCCAAT GGTGGCCTTG
2951 GTGCTCCCTA ACTATCTGTT CCCAACCCCA TCCAGCTATC CTTATGGGGC
3001 ACTCCAGACC CCTGCTGAAG GGCCTCCCAC TCCTGCCTCG CACTCCCCTT
3051 CTCCATCCTT GCCCGCCCTC CCCCCGAGTC CTCCTCACCG CCCGGACTCT
3101 CCACTGTTCA ACTCGAGATG CAGCTCTCCA CTCCAGCTCA ATCTGCTGCA
3151 GCTGGAGGAG CTCCCCCGTG CTGAGGGGGC TGCTGTTGCA GGAGGCCCTG
```

TABLE II-continued

Nucleotide sequence of the 4.7 kb RIGUI cDNA

```
3201 GGAGCAGTGC CGGGCCCCCA CCTCCCAGTG CGGAGGCTGC TGAGCCAGAG
3251 GCCAGACTGG CGGAGGTCAC TGAGTCCTCC AATCAGGACG CACTTTCCGG
3301 CTCCAGTGAC CTGCTCGAAC TTCTGCTGCA AGAGGACTCG CGCTCCGGCA
3351 CAGGCTCCGC AGCCTCGGGC TCCTTGGGCT CTGGCTTGGG CTCTGGGTCT
3401 GGTTCAGGCT CCCATGAAGG GGGCAGCACC TCAGCCAGCA TCACTCGCAG
3451 CAGCCAGAGC AGCCACACAA GCAAATACTT TGGCAGCATC GACTCTTCCG
3501 AGGCTGAGGC TGGGGCTGCT CGGGGCGGGG CTGAGCCTGG GGACCAGGTG
3551 ATTAAGTACG TGCTCCAGGA TCCCATTTGG CTGCTCATGG CCAATGCTGA
3601 CCAGCGCGTC ATGATGACCT ACCAGGTGCC CTCCAGGGAC ATGACCTCTG
3651 TGCTGAAGCA GGATCGGGAG CGGCTCCGAG CCATGCAGAA GCAGCAGCCT
3701 CGGTTTTCTG AGGACCAGCG GCGGGAACTG GGTGCTGTGC ACTCCTGGGT
3751 CCGGAAGGGC CAACTGCCTC GGGCTCTTGA TGTGATGGCC TGTGTGGACT
3801 GTGGGAGCAG CACCCAAGAT CCTGGTCACC CTGATGACCC ACTCTTCTCA
3851 GAGCTGGATG GACTGGGGCT GGAGCCCATG GAAGAGGGTG GAGGCGAGCA
3901 GGGCAGCAGC GGTGGCGGCA GTGGTGAGGG AGAGGGCTGC GAGGAGGCCC
3951 AAGGCGGGGC CAAGGCTTCA AGCTCTCAGG ACTTGGCTAT GGAGGAGGAG
4001 GAAGAAGCAG GAGCTCATCC AGTCCAGCCT TACCTACAGC AGGAAACTGC
4051 ACCAGCTAGA CTCCATTCTG GGACCATCTC CAGGAGTCCA TGAGAGGCTT
4101 TCTTCTCCTA TGTCCCAATT CTCAGAACTC AGATGTGGCT AGACCAACCA
4151 GTGGGAAACT GCCCCAGCTT CTCCCACCAT AGGGGGCCGG ACCCCCATCA
4201 CCAGCCTAGG ATCCAGGGGC TGCCTCTGGC CTCTTAGGGA GCAGAGAGCA
4251 GAACTCCGCA GCCCAGCCCA GAGGAGTGTC ACCTCCCACC TTTGGAGAGG
4301 AATCCTTCCC TCCCCTGGAC AAAGTTGCTG ACAAGCTGCT GAAGTGGCCT
4351 CTCCATATTC CAGCTGAGCC TGAATCTGAC TCTTGAGGGT TGGGGCTGCA
4401 CTTATTTATT GCGGGGAGAC AGCTCTCTCT CCCACCTCCT CCCCAGATGG
4451 GAGGAGAGCC TGAGGCCCAA GCAGGACCCG GGGGTTCCAG CCCCTAGCTG
4501 CTCTGGAGTG GGGGAGGTTG GTGGACCATG GAGTCCCTGG TGCTGCCCCT
4551 CAGGTGGGAC CCAGGGGTTC TCAGCTGTAC CCTCTGCCGA TGGCATTTGT
4601 GTTTTTGATA TTTGTGTCTG TTACTACTTT TTTAATACAA AAAGATAAAA
4651 ACGCC
```

TABLE III

Nucleotide sequence of the 3.0 kb RIGUI cDNA

```
  1 GGCTGGAGCG GCGGCGGGCA GGCGTGCGGA GGACACTCCT GCGACCAGGT
 51 ACTGGCTGTG ATCGAACTTC TCAACCCTCA GAGACTTAGA TCTTCCACCT
101 CACTCCCTCA GCCAAGCCTC CAGGCCCCCT CGTGCATCCG TGGTGGCCTC
151 TCTGCCTTCT CTGTTCTGTT CTCCCCATGG CCCAGACATG AGTGGCCCCC
201 TAGAAGGGGC TGATGGGGGA GGGGACCCCA GGCCTGGGGA ATCATTTTGT
```

TABLE III-continued

Nucleotide sequence of the 3.0 kb RIGUI cDNA

```
 251 CCTGGGGGCG TCCCATCCCC TGGGCCCCCA CAGCACCGGC CTTGCCCAGG
 301 CCCCAGCCTG GCCGATGACA CCGATGCCAA CAGCAATGGT TCAAGTGGCA
 351 ATGAGTCCAA CGGGCATGAG TCTAGAGGCG CATCTCAGCG GAGCTCACAC
 401 AGCTCCTCCT CAGGCAACGG CAAGGACTCA GCCCTGCTGG AGACCACTGA
 451 GAGCAGCAAG AGCACAAACT CTCAGAGCCC ATCCCCACCC AGCAGTTCCA
 501 TTGCCTACAG CCTCCTGAGT GCCAGCTCAG AGCAGGACAA CCCGTCCACC
 551 AGTGGCTGCA GCAGTGAACA GTCAGCCCGG GCAAGGACTC AGAAGGAACT
 601 CATGACAGCA CTTCGAGAGC TCAAGCTTCG ACTGCCGCCA GAGCGCCGGG
 651 GCAAGGGCCG CTCTGGGACC CTGGCCACGC TGCAGTACGC ACTGGCCTGT
 701 GTCAAGCAGG TGCAGGCCAA CCAGGAATAC TACCAGCAGT GGAGCCTGGA
 751 GGAGGGCGAG CCTTGCTCCA TGGACATGTC CACCTATACC CTGGAGGAGC
 801 TGGAGCACAT CACGTCTGAG TACACACTTC AGAACCAGGA TACCTTCTCA
 851 GTGGCTGTCT CCTTCCTGAC GGGCCGAATC GTCTACATTT CGGAGCAGGC
 901 AGCCGTCCTG CTGCGTTGCA AGCGGGACGT GTTCCGGGGT ACCCGCTTCT
 951 CTGAGCTCCT GGCTCCCCAG GATGTGGGAG TCTTCTATGG TTCCACTGCT
1001 CCATCTCGCC TGCCCACCTG GGGCACAGGG GCCTCAGCAG GTTCAGGCCT
1051 CAGGGACTTT ACCCAGGAGA AGTCCGTCTT CTGCCGTATC AGAGGAGGTC
1101 CTGACCGGGA TCCAGGGCCT CGGTACCAGC CATTCCGCCT AACCCCGTAT
1151 GTGACCAAGA TCCGGGTCTC AGATGGGGCC CCTGCACAGC CGTGCTGCCT
1201 GCTGATTGCA GAGCGCATCC ATTCGGGTTA CGAAGCTCCC CGGATACCCC
1251 CTGACAAGAG GATTTTCACT ACGCGGCACA CACCCAGCTG CCTCTTCCAG
1301 GATGTGGATG AAAGGGCTGC CCCCCTGCTG GGCTACCTGC CCAGGACCT
1351 CCTGGGGGCC CCAGTGCTCC TGTTCCTGCA TCCTGAGGAC CGACCCCTCA
1401 TGCTGGCTAT CCACAAGAAG ATTCTGCAGT TGGCGGGCCA GCCCTTTGAC
1451 CACTCCCCTA TCCGCTTCTG TGCCCGCAAC GGGGAGTATG TCACCATGGA
1501 CACCAGCTGG GCTGGCTTTG TGCACCCCTG GAGCCGCAAG GTAGCCTTCG
1551 TGTTGGGCCG CCACAAAGTA CGCACGGCCC CCTGAATGA GGACGTGTTC
1601 ACTCCCCCGG CCCCCAGCCC AGCTCCCTCC CTGGACACTG ATATCCAGGA
1651 GCTGTCAGAG CAGATCCACC GGCTGCTGCT GCAGCCCGTC ACAGCCCCA
1701 GCCCCACGGG ACTCTGTGGA GTCGGCGCCG TGACATCCCC AGGCCCTCTC
1751 CACAGCCCTG GTCCTCCAG TGATAGCAAC GGGGGTGATG CAGAGGGGCC
1801 TGGGCCTCCT GCGCCAGTGA CTTTCCAACA GATCTGTAAG GATGTGCATC
1851 TGGTGAAGCA CCAGGGCCAG CAGCTTTTA TTGAGTCTCG GGCCCGGCCT
1901 CAGTCCCGGC CCCGCCTCCC TGCTACAGGC ACGTTCAAGG CCAAGGCCCT
1951 TCCCTGCCAA TCCCCAGACC CAGAGCTGGA GGCGGGTTCT GCTCCCGTCC
2001 AGGCCCCACT AGCCTTGGTC CCTGAGGAGG CCGAGAGGAA AGAAGCCTCC
2051 AGCTGCTCCT ACCAGCAGAT CAACTGCCTG ACAGCATCC TCAGGTACCT
2151 CCTCCTATAC CACCTCCTCA GCCTCTGACG ACGACAGGCA GAGGACAGGT
2201 CCAGTCTCTG TGGGGACCAA GAAAGATCCG CCGTCAGCAG CGCTGTCTGG
```

TABLE III-continued

Nucleotide sequence of the 3.0 kb RIGUI cDNA

```
2251 GGAGGGGGCC ACCCCACGGA AGGAGCCAGT GGTGGGAGGC ACCCTGAGCC
2301 CGCTCGCCCT GGCCAATAAG GCGGAGAGTG TGGTGTCCGT CACCAGTCAG
2351 TGTAGCTTCA GCTCCACCAT GCTCCATGTG GGAGACAAGA AGCCCCCGGA
2401 GTCGGACATC ATCATGATGG AGGACCTGCC TGGTCTAGCC CCAGGCCCAG
2451 CCCCCAGCCC GACTCCATTC TGGGACCATC TCCAGGAGTC CATGAGAGGC
2501 TTTCTTCTCC TATGTCCCAA TTCTCAGAAC TCAGATGTGG CTAGACCAAC
2551 CAGTGGGAAA CTGCCCCAGC TTCTCCCACC ATAGGGGCC GGACCCCCAT
2601 CACCAGCCTA GGATCCAGGG GCTGCCTCTG GCCTCTTAGG GAGCAGAGAG
2651 CAGAACTCCG CAGCCCAGCC CAGAGGAGTG TCACCTCCCA CCTTTGGAGA
2701 GGAATCCTTC CCTCCCCTGG ACAAAGTTGC TGACAAGCTG CTGAAGTGGC
2751 CTCTCCATAT TCCAGCTGAG CCTGAATCTG ACTCTTGAGG GTTGGGGCTG
2801 CACTTATTTA TTGCGGGGAG ACAGCTCTCT CTCCCACCTC CTCCCCAGAG
2851 GGGAGGAGAG CCTGAGGCCC AAGCAGGACC CGGGGGTTCC AGCCCCTAGC
2901 TGCTCTGGAG TGGGGGAGGT TGGTGGACCA TGGAGTCCCT GGTGCTGCCC
2951 CTCAGGTGGG ACCCAGGGGT TCTCAGCTGT ACCCTCTGCC GATGGCATTT
3001 GTGTTTTTGA TATTTGTGTC TGTTACTACT TTTTTAATAC AAAAAGATAA
3051 AAACGCC
```

Figures 1, 2:
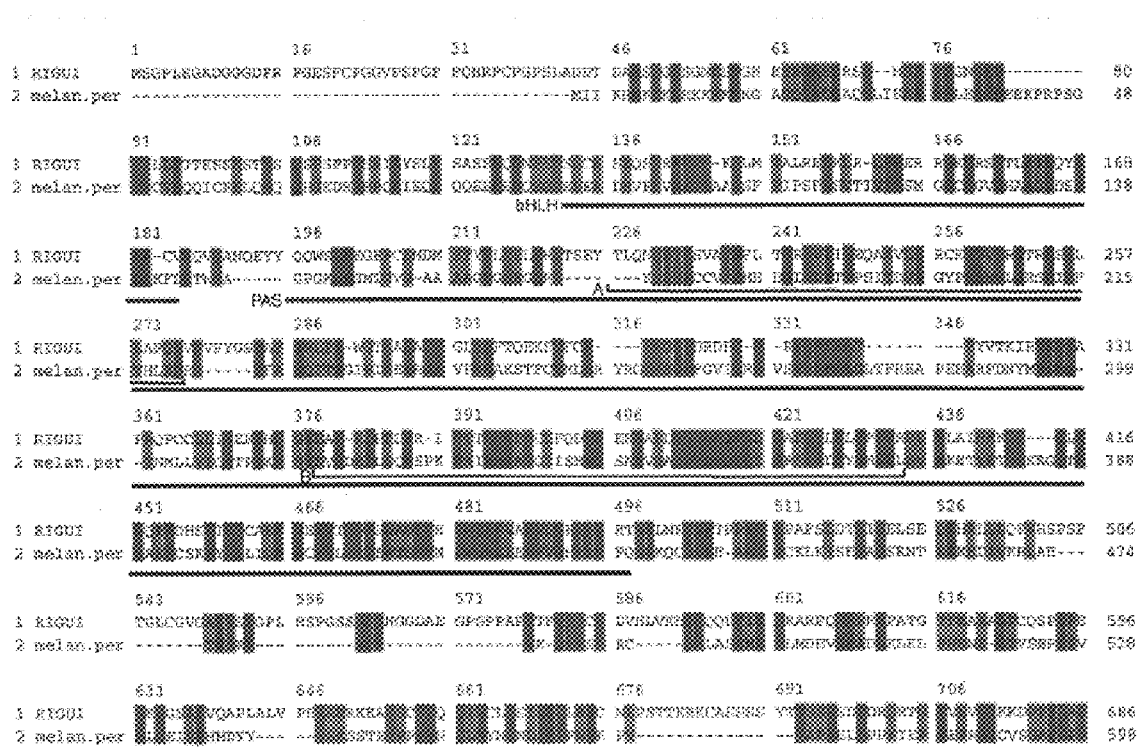
FIG. 2 shows a comparison of the predicted protein sequences of RIGUI and *D. melanogaster* Period. Alignment of the two protein sequences was carried out by the pattern-induced multi-sequence alignment program (PIMA) and the alignment revealed a marked sequence identity between them (Smith and Smith, 1992). The amino acids shaded in red are identical, those shaded in blue are conserved substitutions and those shaded in green are neutral substitutions. The basic-helix-loop-helix motif and the PAS domain are indicated by horizontal lines, and brackets A and B indicate the PAS A and B repeats.

RIGUI 4.7 can be translated into a protein sequence of 1301 amino acids (SEQ ID No: 6) (FIG. 1B, FIG. 2, Gene Bank Accession Number: AF022991). The largest deduced open reading frame from RIGUI 6.6 gave a peptide of 875 amino acids (TABLE IV) (SEQ ID No: 7).

TABLE IV

Amino Acid sequence of RIGUI 6.6

```
  1 MSGPLEGADG GGDPRPGESF CPGGVPSPGP PQHRPCPGPS LADDTDANSN
 51 GSSGNESNGH ESRGASQRSS HSSSSGNGKD SALLETTESS DSTNSQSPSP
101 PSSSIAYSLL SASSEQDNPS TSGCSSEQSA RARTQKELMT ALRELKLRLP
151 PERRGKGRSG TLATLQYALA CVKQVQANQE YYQQWSLEEG EPCSMDMSTY
201 TLEELEHITS EYTLQNQDTF SVAVSFLTGR IVYISEQAAV LLRCKRDVFR
251 GTRFSELLAP QDVGVFYGST APSRLPTWGT GASAGSGLRD FTQEKSVFCR
301 IRGGPDRDPG PRYQPFRLTP YVTKIRVSDG APAQPCCLLI AERIHSGYEA
351 PRIPPDKRIF TTRHTPSCLF QDVDERAAPL LGYLPQDLLG APVLLFLHPE
401 DRPLMLAIHK KILQLAGQPF DHSPIRFCAR NGEYVTMDTS WAGFVHPWSR
451 KVAFVLGRHK VRTAPLNEDV FTPPAPSPAP SLDTDIQELS EQIHRLLLQP
501 VHSPSPTGLC GVGAVTSPGP LHSPGSSSDS NGGDAEGPGP PAPVTFQQIC
551 KDVHLVKHQG QQLFIESRAR PQSRPRLPAT GTFKAKALPC QSPDPELEAG
601 SAPVQAPLAL VPEEAERKEA SSCSYQQINC LDSILRYLES CNLPSTTKRK
651 CASSSSYTTS SASDDDRQRT GPVSVGTKKD PPSAALSGEG ATPRKEPVVG
701 GTLSPLALAN KAESVVSVTS QCSFSSTIVH VGDKKPPESD IIMMEDLPGL
```

TABLE IV-continued

Amino Acid sequence of RIGUI 6.6

```
751 APGPAPSPAP SPTVAPDPAP DAYRPVGLTK AVLSLHTQKE EQAFLSRFRD

801 LGRLRGLDSS STAPSALGER GSHLGPPGAC PLPSLGLDCW GVGLKGGVSA

851 PGTQAGVAST TRPCLGTGPS LASPH
```

The initial 821 amino acids were identical to those of RIGUI 4.7, but more C-terminal residues diverged. The largest deduced reading frame of the RIGUI 3.0 was 798 amino acids long (TABLE V) (SEQ ID No:8). RIGUI 4.7 and RIGUI 3.0 diverge at amino acid 758. Taken together, the RIGUI gene gives rise to at least three proteins that differ in their C-terminal regions.

TABLE V

Amino Acid sequence of RIGUI 3.0

```
  1 MSGPLEGADG GGDPRPGESF CPGGVPSPGP PQHRPCPGPS LADDTDANSN

51 GSSGNESNGH ESRGASQRSS HSSSSGNGKD SALLETTESS KSTNSQSPSP

101 PSSSIAYSLL SASSEQDNPS TSGCSSEQSA RARTQKELMT ALRELKLRLP

151 PERRGKGRSG TLATLQYALA CVKQVQANQE YYQQWSLEEG EPCSMDMSTY

201 TLEELEHITS EYTLQNQDTF SVAVSFLTGR IVYISEQAAV LLRCKRDVFR

251 GTRFSELLAP QDVGVFYGST APSRLPTWGT GASAGSGLRD FTQEKSVFCR

301 IRGGPDRDPG PRYQPFRLTP YVTKIRVSDG APAQPCCLLI AERIHSGYEA

351 PRIPPDKRIF TTRHTPSCLF QDVDERAAPL LGYLPQDLLG APVLLFLHPE

401 DRPLMLAIHK KILQLAGQPF DHSPIRFCAR NGEYVTMDTS WAGFVHPWSR

451 KVAFVLGRHK VRTAPLNEDV FTPPAPSPAP SLDTDIQELS EQIHRLLLQP

501 VHSPSPTGLC GVGAVTSPGP LHSPGSSSDS NGGDAEGPGP PAPVTFQQIC

551 KDVHLVKHQG QQLFIESRAR PQSRPRLPAT GTFKAKALPC QSPDPELEAG

601 SAPVQAPLAL VPEEAERKEA SSCSYQQINC LDSILRYLES CNLPSTTKRK

651 CASSSSYTTS SASDDDRQRT GPVSVGTKKD PPSAALSGEG ATPRKEPVVG

701 APGPAPSPTP FWDHLQESMR GFLLLCPNSQ NSDVARPTSG KLPQLLPP
```

BLAST and FASTA searches against peptide sequences revealed significant protein sequence similarity of RIGUI 4.7 open reading frame to *Drosophila melanogaster* Period (Per) protein (FIG. 2). A BLAST search yielded the following probability scores P(N) of homology: Period (various Drosophila species) between $5.1 \times 10^{-26}$ to $5.2 \times 10^{-20}$, the next highest score was with the mammalian aryl hydrocarbon receptor nuclear translocater which gave a P(N) of $5.9 \times 10^{-14}$, and the P(N) with mouse single minded protein (SIM1) was 0.52. The overall homology, i.e., identical amino acids conservative and neutral substitutions) between RIGUI and Period of *Drosophila melanogaster* is about 44% and a slightly higher homology of about 48% is found in the initial 500 amino acids which include a PAS domain.

The PAS domain was initially observed in "*Drosophila melanogaster* period" (Per), in "human aryl hydrocarbon receptor nuclear translocater protein" (ARNT) and the "Drosophila single minded" protein (SIM). The PAS domain is approximately 260 amino acids in length and contains two direct repeats of 51 amino acids each (A and B, see FIGS. 1B and FIG. 2). Sequence homology in the Per A and B repeats is 39 and 61%, respectively. Importantly, many of the amino acids conserved between *Drosophila melanogaster* per and RIGUI reside outside of the PAS domain, emphasizing the similarity between the two proteins (FIG. 2). In contrast, very little protein sequence identity was observed outside of the PAS domain of RIGUI or Per when compared to other PAS domain proteins including ARNT, SIM, AHR, NPAS1, NPAS2 and CLOCK.

Using the PHDsec program (EMBL) for secondary structure analysis, the N-terminal region of RIGUI was determined to contain a putative basic helix loop helix (bHLH) motif. Alignment of the bHLH region of RIGUI with that of other bHLH-PAS proteins revealed that several of the bHLH consensus amino acids are conserved (FIG. 3). Analysis of the *D. melanogaster* period protein with the same protein did not reveal a bHLH motif. Taken together, RIGUI contains a bHLH-motif and a PAS domain thus emerging as a member of a family of putative transcription factors which include the recently identified gene products of NPAS1, NPAS2 and CLOCK (Zhou et al., 1997, King et al., 1997). From the sequence analysis, it was proposed that RIGUI is a human ortholog of Drosophila Per.

EXAMPLE 7
Oscillation of RIGUI mRNA Expression in the Retina

As demonstrated for per and tim in Drosophila (Hardin et al., 1990, Sehgal et al., 1994) and the frequency gene in Neurospora (Dunlap, 1993), circadian oscillator genes are expressed in a periodic manner reflecting the 24 hour day/night cycle. To examine whether expression of RIGUI behaves in a similar way, its expression in the mouse was examined. A murine brain cDNA library was screened with the human RIGUI 4.7 cDNA as probe, and a mouse homolog termed m-rigui was identified (TABLE VI) (SEQ ID No: 9), encoding a protein of 1291 amino acids (TABLE VII) (SEQ ID No: 10) which has 92% amino acid identity with human RIGUI. The PAS- and bHLH domains of the two proteins are 98% identical and (Gene Bank Accession Number: AF022992).

TABLE VI

Mouse RIGUI 4.7 kb cDNA

```
   1 CGGGTCGACC CACGCGTCCG CCCACGCGTC CGGCGGAGCT TCTGGGTTGC
  51 GGGCCGAAAC GGCAAGCGGA TGGAGGGCGC TCGAACGGCC AGGTGTCGTG
 101 ATTAAATTAG TCAGCCCTCA GAGACAGGCG TCCTACCTCC TTTATCCAGA
 151 CCTCAAAAGC CCCGTTGTGC ACCCGTGGTG GCTTCTTCAC CTTCCCTGTT
 201 TCGTCCTCCA CTGTATGGCC CAGAGATGAG TGGTCCCCTA GAAGGGGCCG
 251 ATGGGGGAGG AGACCCCAGG CCCGGAGAAC CTTTTTGTCC TGGAGGAGTC
 301 CCATCCCCTG GGGCCCCGCA GCACCGGCCT TGTCCAGGCC CCAGCCTGGC
 351 TGATGACACT GATGCAAACA GCAATGGCTC AAGTGGCAAT GAGTCCAACG
 401 GACCCGAGTC CAGGGGCGCA TCTCAGCGGA GTTCTCATAG TTCCTCTTCT
 451 GGCAATGGCA AGGACTCAGC TCTGCTGGAG ACCACTGAGA GCAGCAAGAG
 501 TACAAACTCA CAGAGCCCAT CCCCACCCAG CAGCTCCATT GCCTACAGCC
 551 TCCTGAGTGC GAGCTCAGAG CAGGACAACC CATCTACCAG TGGCTGCAGC
 601 AGTGAACAGT CAGCTCGAGC CAGGACCCAG AAAGAACTCA TGACTGCACT
 651 TCGGGAGCTC AAACTTCGAC TGCCACCAGA GCGTCGGGGC AAGGGCCGCT
 701 CTGGGACCTT GGCCACACTG CAGTACGCTC TGGCCTGTGT CAAGCAGGTT
 751 CAGGCTAACC AGGAATATTA CCAGCAGTGG AGTCTGGAGG AGGGTGAGCC
 801 TTGTGCCATG GACATGTCTA CTTACACCCT GGAGGAATTG GAGCATATCA
 851 CATCCGAATA CACACTTCGA AACCAGGACA CCTTCTCTGT GGCTGTGTCC
 901 TTCCTGACAG GCCGGATTGT CTATATTTCG GAGCAGGCAG GTGTCCTGCT
 951 GCGTTGCAAA CGGGATGTGT TTCGGGGTGC CCGCTTCTCA GAGCTCCTGG
1001 CTCCCCAGGA TGTGGGTGTC TTCTATGGCT CTACTACACC ATCTCGACTG
1051 CCCACCTGGG GCACTGGCAC CTCTGCAGGT TCAGGTCTCA AGGACTTCAC
1101 CCAGGAAAAG TCTGTCTTCT GCCGAATCAG AGGAGGTCCT GACCGGGATC
1151 CAGGGCCTCG GTACCAGCCA TTCCGCCTAA CCCCATATGT GACCAAGATT
1201 CGGGTCTCAG ATGGAGCCCC TGCACAGCCG TGCTGCCTAC TCATTGCCGA
1251 GCGCATCCAC TCTGGTTATG AAGCTCCCCG GATCCCTCCT GACAAGAGGA
1301 TCTTCACCAC CCGACACACA CCAAGCTGCC TCTTCCAGGA TGTAGATGAA
1351 AGGGCTGCCC CACTGCTGGG TTACCTTCCC CAGGATCTCC TGGGGGCTCC
1401 AGTACTTCTC TTTCTACATC CTGAGGACCG ACCCCTCATG CTGGCCATTC
1451 ATAAGAAGAT ACTGCAGCTG GCAGGCCAGC CCTTTGACCA TTCCCCTATT
1501 CGCTTCTGTG CTCGGAACGG GGAATATGTC ACCATGGACA CCAGCTGGGC
1551 CGGTTTTGTG CACCCCTGGA GCCGCAAGGT GGCTTTCGTG TTGGGTCGCC
1601 ATAAAGTGCG CACGGCACCC CTGAATGAGG ACGTCTTCAC TCCCCCAGCC
```

TABLE VI-continued

Mouse RIGUI 4.7 kb cDNA

```
1651 CCCAGCCCAG CTCCGTCCCT GGACTCTGAT ATCCAGGAGC TCTCAGAGCA
1701 GATCCATCGA TTGCTGCTGC AGCCTGTGCA CAGCTCCAGC CCACGGGGC
1751 TCTGTGGAGT TGGCCCTCTG ATGTCCCCTG GTCCTCTACA CAGCCCTGGC
1801 TCCTCCAGTG ATAGCAATGG GGGGACGCT GAGGGCCTG GGCCTCCTGC
1851 TCCAGTGACT TTCCAGCAGA TCTGTAAGGA TGTGCATCTG GTAAAGCACC
1901 AGGGACAACA GCTCTTCATT GAATCTCGGG CCAAGCCCCC ACCCCGGCCC
1951 CGCCTCCTTG CTACAGGTAC ATTCAAAGCC AAAGTCCTTC CCTGCCAGTC
2001 CCCAAACCCC GAACTGGAGG TGGCCCCAGT TCCTGACCAA GCCTCGTTAG
2051 CCTTGGCCCC TGAGGAGCCA GAGAGGAAAG AAACCTCTGG CTGTTCCTAC
2101 CAGCAGATCA ACTGCCTGGA CAGCATCCTC AGGTATTTGG AGAGCTGCAA
2151 CATTCCCAGT ACAACCAAGC GTAAATGTGC CTCCTCCTCC TCCTACACTG
2201 CCTCTTCAGC CTCTGATGAT GACAAGCAGA GGGCAGGTCC AGTTCCTGTG
2251 GGGGCCAAGA AGATCCGTC GTCAGCAATG CTGTCTGGGG AGGGGGCAAC
2301 TCCTCGGAAG GAGCCAGTGG TGGGAGGCAC CCTGAGCCCG CTCGCCCTGG
2351 CCAATAAGGC AGAGAGCGTG GTGTCCGTCA CCAGTCAGTG TAGCTTCAGC
2401 TCCACCATCG TCCATGTGGG AGACAAGAAG CCCCCGGAGT CGGACATCAT
2451 CATGATGGAA GACCTGCCTG GCCTGGCCCC TGGCCCAGCC CCCAGTCCGG
2501 CCCCCAGCCC CACAGTAGCC CCTGACCCAA CCCCAGATGC TTATCGCCCA
2551 GTFFFTCTGA CCAAGGCCGT GCTGTCCCTG CACACACAGA AGGAAGAGCA
2601 AGCCTTCCTC AACCGCTTCA GAGATCTTGG CAGGCTTCGT GGACTTGACA
2651 CCTCTTCTGT GGCCCCCTCA GCCCCTGGCT GCCACCATGG CCCCATTCCC
2701 CCTGGTCGCC GACACCACTG CCGATCTAAA GCAAAGCGTT CCCGCCACCA
2751 CCACCACCAG ACCCCCCGGC CCGAAACTCC CTGCTATGTC TCCCATCCTT
2801 CACCTGTGCC CTCTTCTGGA CCCTGGCCAC CCCCACCAGC CACGACCCCC
2851 TTCCCAGCAA TGGTCCAGCC CTACCCACTC CCAGTATTCT CCCCTCGAGG
2901 AGGACCCCAG CCCCTTCCCC CTGCCCCTAC ATCTGTGTCC CCTGCTACCT
2951 TCCCTTCTCC CTTAGTGACC CCAATGGTGG CCTTGGTGCT CCCTAACTAT
3001 CTATTCCCTA CCCCACCTAG TTATCCATAT GGGGTGTCCC AGGCCCCTGT
3051 TGAGGGGCCA CCCACGCCTG CTTCCCACTC GCCCTCTCCA TCCCTGCCCC
3101 CACCACCTCT CAGCCCCCCC CACCGCCCAG ACTCCCCACT GTTCAACTCG
3151 AGATGCAGCT CCCCACTCCA GCTCAATCTG CTGCAGCTTG AGGAGTCCCC
3201 CCGCACGGAG GGGGCGCTG CTGCAGGAGG CCCAGGAAGC AGTGCTGGGC
3251 CCCTGCCTCC CAGTGAGGAG ACTGCTGAGC CAGAGGCCAG ATTGGTGGAG
3301 GTTACTGAGT CGTCCAATCA GGATGCACTT TCAGGCTCCA GCGACCTGCT
3351 GGAGCTACTG CTCCAAGAAG ACTCTCGCTC GGGCACAGGC TCCGCAGCCT
3401 CAGGCTCCCT GGGCTCTGGC CTGGGCTCTG GTCTGGTTC AGGATCCCAC
3451 GAAGGGGGAA GCACCTCAGC CAGCATCACC CGCAGCAGTC AGAGCAGCCA
3501 TACAAGCAAG TACTTTGGCA GCATCGACTC TTCCGAGGCT GAAGCTGGGG
3551 CTGCTCGGGC CAGGACTGAG CCTGGGGACC AGGTCATTAA GTGTGTGCTC
```

TABLE VI-continued

Mouse RIGUI 4.7 kb cDNA

```
3601 CAGGACCCCA TCTGGCTGCT CATGGCCAAT GCCGACCAGC GTGTCATGAT
3651 GACATACCAG GTGCCGTCCA GGGATGCAGC CTCTGTGCTG AAGCAAGACC
3701 GGGAGAGGCT CCGGGCCATG CAGAAACAGC AGCCACGGTT CTCAGAGGAC
3751 CAGAGGCGGG AACTGGGTGC TGTGCACTCC TGGGTCCGGA AGGGCCAGCT
3801 GCCTCGGGCC CTTGATGTGA TGGCGTGTGT GGACTGTGGC AGCAGCGTTC
3851 AAGATCCTGG CCACTCTGAT GACCCGCTCT TCTCAGAACT GGATGGATTG
3901 GGGCTGGAGC CCATGGAAGA GGGTGGAGGC GAGGGTGGTG GGTGTGGTGT
3951 TGGCGGTGGT GGGGGTGATG GTGGTGAGGA GGCCCAGACC CAAATTGGGG
4001 CTAAGGGTTC AAGCTCTCAG GACTCTGCCA TGGAGGAAGA AGAGCAAGGT
4051 GGGGGCTCAT CCAGCCCAGC TTTACCTGCA GAAGAAAACA GCACCAGCTA
4101 GATCCATTTT GGGGCCGCTT ACAGCAGTCT AATGAGAGGC TTCCTTTCGA
4151 CCATGTTGGG GTTCTTATAA CTCAAGATAC AGCTGGACCA ACCAATAGGA
4201 AACTGCCCCA GCTTCTCCCA ACATAGGGGG CTGGACCCCC ATTACCAGCC
4251 CAGGCACAGG AGCTGCCTCT AGCTTCTTAG CAGAGTGGAA GTTCTCAGCC
4301 CCATTTGGAG GATTGTCCAG GCCCGTCCCA CTGAGGAGAC GGGCGGGTCT
4351 TCGGTTAAGG TTGCTGACAA GCTGCTGAAG TGGTCTGTCC AAATCCCAGC
4401 TGAGCCTGAG TCCCAGTCGC AGGGTTGGGG CTGCACTTAT TTATTTGGGA
4451 GAGACAGCTC ACTCTCCCAC CTCACCCCAA GATGGGAGGA GGGGAACCTG
4501 GGATCTGTGT AGGATCCAGG TCCGTGAACC CCTAGCTGCT CCAGGGTGGG
4551 GGAGGTTGGT GGACCATGGA GTCCCTGGTG CTGCCCCTCA GGTGGGACCC
4601 AGGTGTTCTC AGCTCTACCC TCTACCAATG ACATTTGTGT TTTTGATATT
4651 GTGTCTGTTA TTTTTTTTTT AATACAAAAT GACAAAATGA AAACCAAAA
```

TABLE VII

Mouse rigui amino acid sequence

```
  1 MSGPLEGADG GGDPRPGEPF CPGGVPSPGA PQHRPCPGPS LADDTDANSN
 51 GSSGNESNGP ESRGASQRSS HSSSSGNGKD SALLETTESS KSTNSQSPSP
101 PSSSIAYSLL SASSEQDNPS TSGCSSEQSA RARTQKELMT ALRELKLRLP
151 PERRGKGRSG TLATLQYALA CVKQVQANQE YYQQWSLEEG EPCAMDMSTY
201 TLEELEHITS EYTLRNQDTF SVAVSFLTGR IVYISEQAGV LLRCKRDVFR
251 GARFSELLAP QDVGVFYGST TPSRLPTWGT GTSAGSGLKD FTQEKSVFCR
301 IRGGPDRDPG PRYQPFRLTP YVTKIRVSDG APAQPCCLLI AERIHSGYEA
351 PRIPPDKRIF TTRHTPSCLF QDVDERAAPL LGYLPQDLLG APVLLFLHPE
401 DRPLMLAIHK KILQLAGQPF DHSPIRFCAR NGEYVTMDTS WAGFVHPWSR
451 KVAFVLGRHK VRTAPLNEDV FTPPAPSPAP SLDSDIQELS EQIHRLLLQP
501 VHSSSPTGLC GVGPLMSPGP LHSPGSSSDS NGGDAEGPGP PAPVTFQQIC
551 KDVHLVKHQG QQLFIESRAK PPPRPRLLAT GTFKAKVLPC QSPNPELEVA
601 PVPDQASLAL APEEPERKET SGCSYQQINC LDSILRYLES CNIPSTTKRK
```

TABLE VII-continued

Mouse rigui amino acid sequence

```
 651 CASSSSYTAS SASDDDKQRA GPVPVGAKKD PSSAMLSGEG ATPRKEPVVG

701 GTLSPLALAN KAESVVSVTS QCSFSSTIVH VGDKKPPESD IIMMEDLPGL

751 APGPAPSPAP SPTVAPDPTP DAYRPVGLTK AVLSLHTQKE EQAFLNRFRD

801 LGRLRGLDTS SVAPSAPGCH HGPIPPGRRH HCRSKAKRSR HHHHQTPRPE

851 TPCYVSHPSP VPSSGPWPPP PATTPFPAMV QPYPLPVFSP RGGPQPLPPA

901 PTSVSPATFP SPLVTPMVAL VLPNYLFPTP PSYPYGVSQA PVEGPPTPAS

951 HSPSPSLPPP PLSPPHRPDS PLFNSRCSSP LQLNLLQLEE SPRTEGGAAA

1001 GGPGSSAGPL PPSEETAEPE ARLVEVTESS NQDALSGSSD LLELLLQEDS

1051 RSGTGSAASG SLGSGLGSGS GSGSHEGGST SASITRSSQS SHTSKYFGSI

1101 DSSEAEAGAA RARTEPGDQV IKCVLQDPIW LLMANADQRV MMTYQVPSRD

1151 AASVLKQDRE RLRAMQKQQP RFSEDQRREL GAVHSWVRKG QLPRALDVMA

1201 CVDCGSSVQD PGHSDDPLFS ELDGLGLEPM EEGGGEGGGC GVGGGGDGG

1251 EEAQTQIGAK GSSSQDSAME EEEQGGGSSS PALPAEENST S
```

Figure 4:
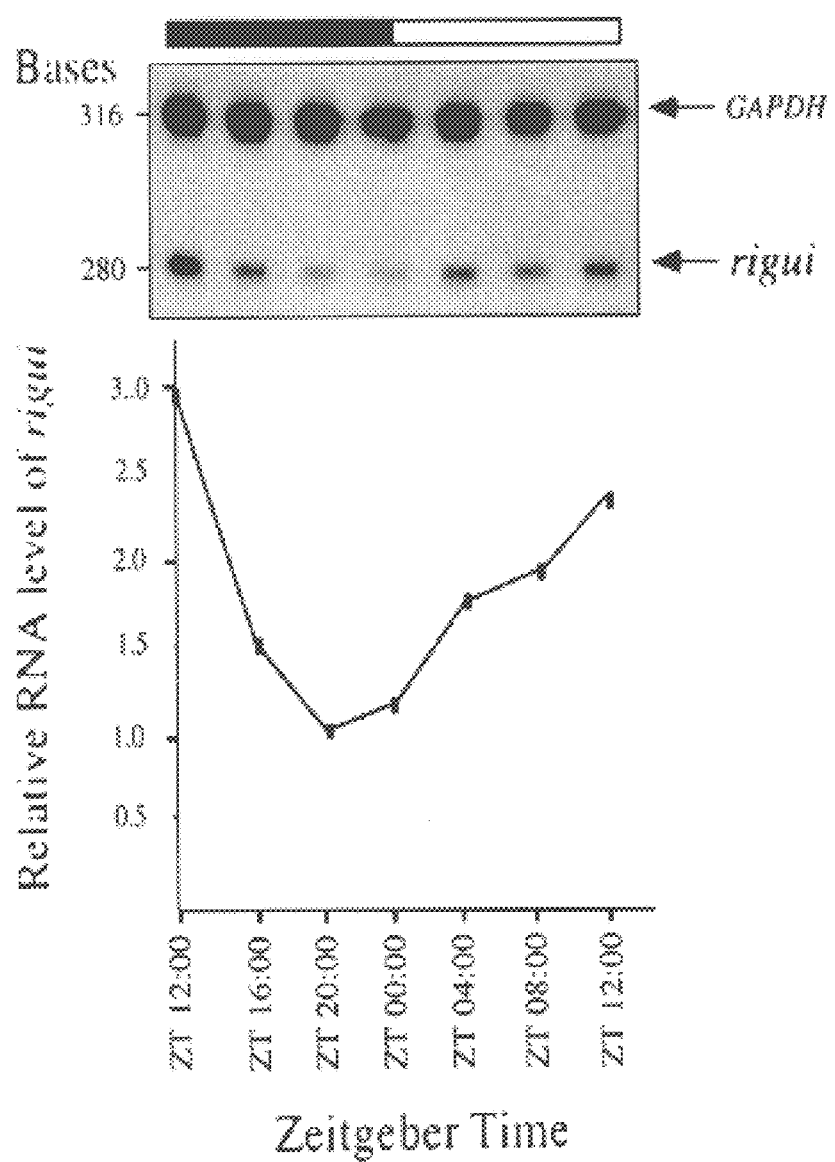
FIG. 4 shows the circadian regulation of m-rigui in the mouse retina of 129/SvEvBrd male mice. Retina RNA were isolated at different zeitgeber times (ZT) indicated on the abscissa. Amount of m-rigui expression was quantified by RNase protection assays and calibrated in reference to GAPDH mRNA levels using a Fuji BAS-100 phosphoimager. The graph illustrates the relative transcript level of m-rigui normalized to GAPDH as a function of circadian times. The smallest value is adjusted as 1 and a peak level of 2.9 is observed at ZT12. The diurnal cycle is indicated by the light and dark bar.

The level of m-rigui mRNA was measured by RNase protection assays using RNA from the retinae of six adult male mice sacrificed every 4 hours during a 12 hours light/12 hours dark cycle. The mammalian retina contains a circadian oscillator not dependent on that from the suprachiasmatic nucleus (Tosini and Menaker, 1996). The level of m-rigui mRNA increased during the light phase from ZT4 to ZT 12 (whereby Zeitgeber time (ZT) ZT0 is the time when lights were turned on and ZT12 is when lights were turned off) and decreased during the dark phase between ZT16 to ZT24/ZT0 (FIG. 4). In contrast, expression of GAPDH, an internal standard, remains constant during the same time span. When the level of m-rigui expression was normalized to that of GAPDH, the m-rigui RNA abundance was found to change 2.9 fold between the highest and the lowest levels in the daily cycle. m-rigui mRNA levels in the retina were also determined over a period of 3 days using reverse transcriptase PCR with circadian rhythms similar to those shown in FIG. 4 (data not shown). These results indicate that the expression of the m-rigui transcript is circadian in nature and that this gene may be part of a molecular clock.

EXAMPLE 8

Oscillation of m-rigui Expression in the Suprachiasmatic Nucleus, the Pars Tuberalis, and the Purkinje Neurons In order to determine whether m-rigui was broadly expressed in specific regions of the brain, expression analysis by in situ hybridization was performed. In situ hybridization was carried out using a 544 nucleotide long riboprobe corresponding to the coding region of m-rigui. Adult male 129/SvEvBrd mice, kept in a 12 hour light/12 hours dark cycle, were sacrificed at 6 hour time intervals, and their brains were rapidly removed and fixed in ice-cold fixative. The four time points chose were ZT6, ZT12, ZT18, and ZT24. To avoid the induction of immediate early genes by light which could occur at ZT0 (Aronin et al., 1990, Kornhauser et al., 1992), the animals were not sacrificed at this time point but at ZT24.

Figure 5:
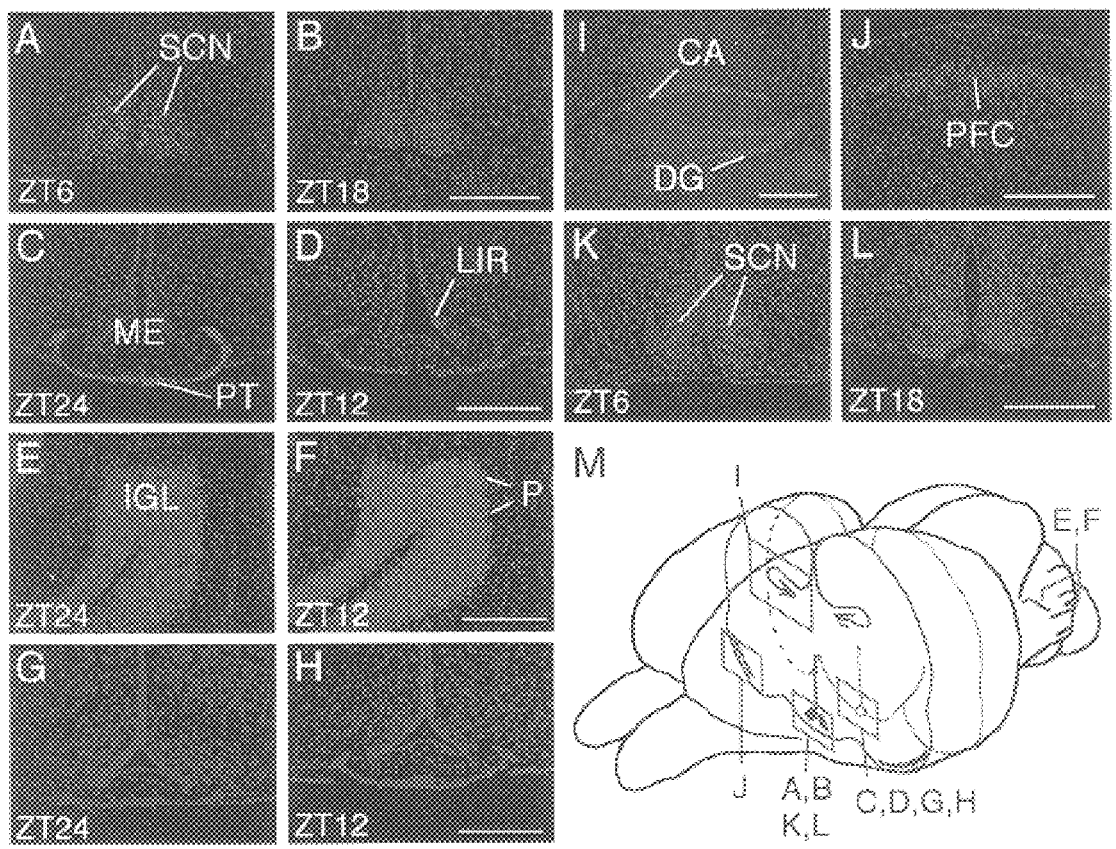
FIGS. 5A–5M show the circadian regulation of m-rigui in the mouse brain. All micrographs were taken from brains of male 129/SvEvBrd mice, except for those shown in G and H, which show tissue from C57BL/6 males.

FIG. 5 shows an analysis of m-rigui expression on coronal and sagittal brain sections. Expression in the suprachiasmatic nucleus was high at CT6 (FIG. 5A), much reduced at CT12 (data not shown), was not detected at CT18 (FIG. 5B) and was very low at CT24 (data not shown). Thus as in the retina, there was a circadian pattern of m-rigui expression in the suprachiasmatic nucleus. Such a temporal profile was also found in the pars tuberalis, that surrounds the hypophysial stalk of the pituitary gland (FIGS. 5C and 5D). However, in this case expression was highest at CT24 (FIG. 5C) and not detected at CT12 (FIG. 5D).

Another site of periodic m-rigui expression was the Purkinje neurons of the cerebellum (FIGS. 5E, F). A high level of expression in Purkinje neurons is seen at ZT12 (FIG. 5F) and expression was minimal at ZT24 (FIG. 5E). This expression profile is similar to that seen in the retina (FIG. 4), but different from the situation in the suprachiasmatic nucleus or the pars tuberalis.

When the expression of m-rigui in C57BL/6 male mice was examined, the circadian nature of m-rigui expression in the suprachiasmatic nucleus was identical to that seen in 129/SvEvBrd males (data not shown). Remarkably, there was no expression of m-rigui in the pars tuberalis at any time point examined. FIGS. 5G and 5H illustrate the absence of m-rigui transcripts at ZT24 and ZT12. This result suggests strain-specific differences in the regulation of m-rigui expression in this tissue.

Other regions of the brain also expressed m-rigui, including the glomerular- and mitral cell layers of the olfactory bulb (data not shown), the internal granular layer of the cerebellum (FIGS. 5E, 5F), the cornu ammonis and dentate gyrus of the hippocampus (FIG. 5I), the cerebral- and piriform (FIG. 5J) cortices. No circadian changes in m-rigui expression could be detected in these structures.

A recently identified mouse circadian gene clock was also examined for changes in expression in the suprachiasmatic nucleus and in other brain tissues. As reported (King et al., 1997) this gene is broadly expressed in the brain including the suprachiasmatic nucleus. Two different probes, one corresponding to the 5' coding region and the other corresponding to the 3' UTR, failed to detect a circadian pattern of expression in the suprachiasmatic nucleus (FIGS. 5K, 5L) or any other brain structure.

Taken together, this data reveals striking diurnal changes in m-rigui expression. Intriguingly, the times of maximal expression are not the same in suprachiasmatic nucleus, retina, Purkinje neurons, and pars tuberalis. The asynchronous, tissue-specific expression of m-rigui may reflect the fact that there are several independent circadian clocks in mammals.

EXAMPLE 9

Figure 6:
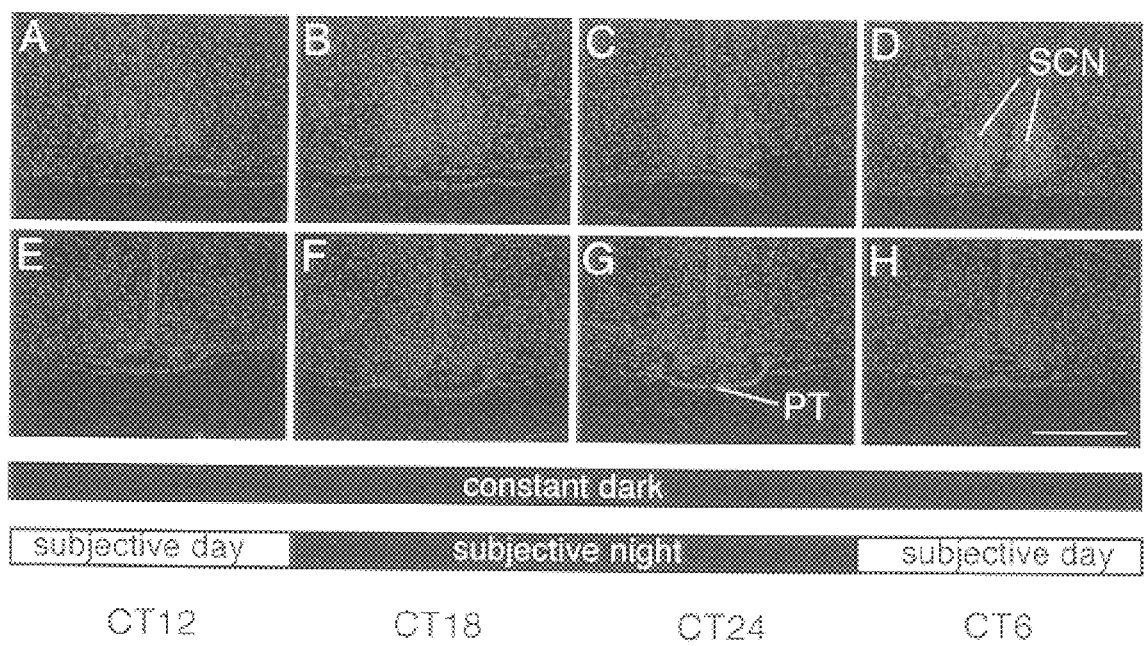
FIGS. 6A–6H show that m-rigui in the suprachiasmatic nucleus (A–D) and pars tuberalis (E–H) in male 129/SvEvBrd mice kept in constant darkness. Animals were transferred from a 12 hour light/12 hour dark cycle to constant darkness. The bar at the bottom of the figure indicates the subjective time. 72 hours after the transfer, animals were sacrificed every 6 hours at the times indicated on the figure. Strongest expression of m-rigui is seen at subjective day ZT6. For abbreviations see FIGS. 5A–5M. Scale bar corresponds to 500 μm.

Expression of m-rigui in the Suprachiasmatic Nucleus Persists Under Free-running Conditions To examine whether the absence of light affects m-rigui expression, 129/SvEvBrd males were transferred from a regular dark/light cycle to a dark/dark cycle. Seventy-two hours later, animals were sacrificed every six hours and dissected under a 15 W safety red light lamp. m-rigui expression in the suprachiasmatic nucleus and the pars tuberalis of these animals is depicted in FIG. 6. At 5 pm, corresponding to the subjective day Circadian Time CT12, expression in the suprachiasmatic nucleus was visible but low (FIG. 6A). Thereafter, transcript levels decreased to background levels (subjective day times CT18 and CT24, FIGS. 6B and C). At subjective CT6 (FIG. 6D), however, expression was very high, comparable to CT6 in FIG. 5A. Expression in the pars tuberalis peaks at CT24 (FIG. 6G), i.e., 6 hours ahead of that in the suprachiasmatic nucleus (FIG. 6D). Thus, the oscillation of m-rigui expression is maintained under free-running conditions. This indicates that this gene is regulated by light-independent, endogenous mechanisms, a feature characteristic of a circadian clock gene.

EXAMPLE 10

Entrainment of m-rigui Expression by Light

Figure 7:
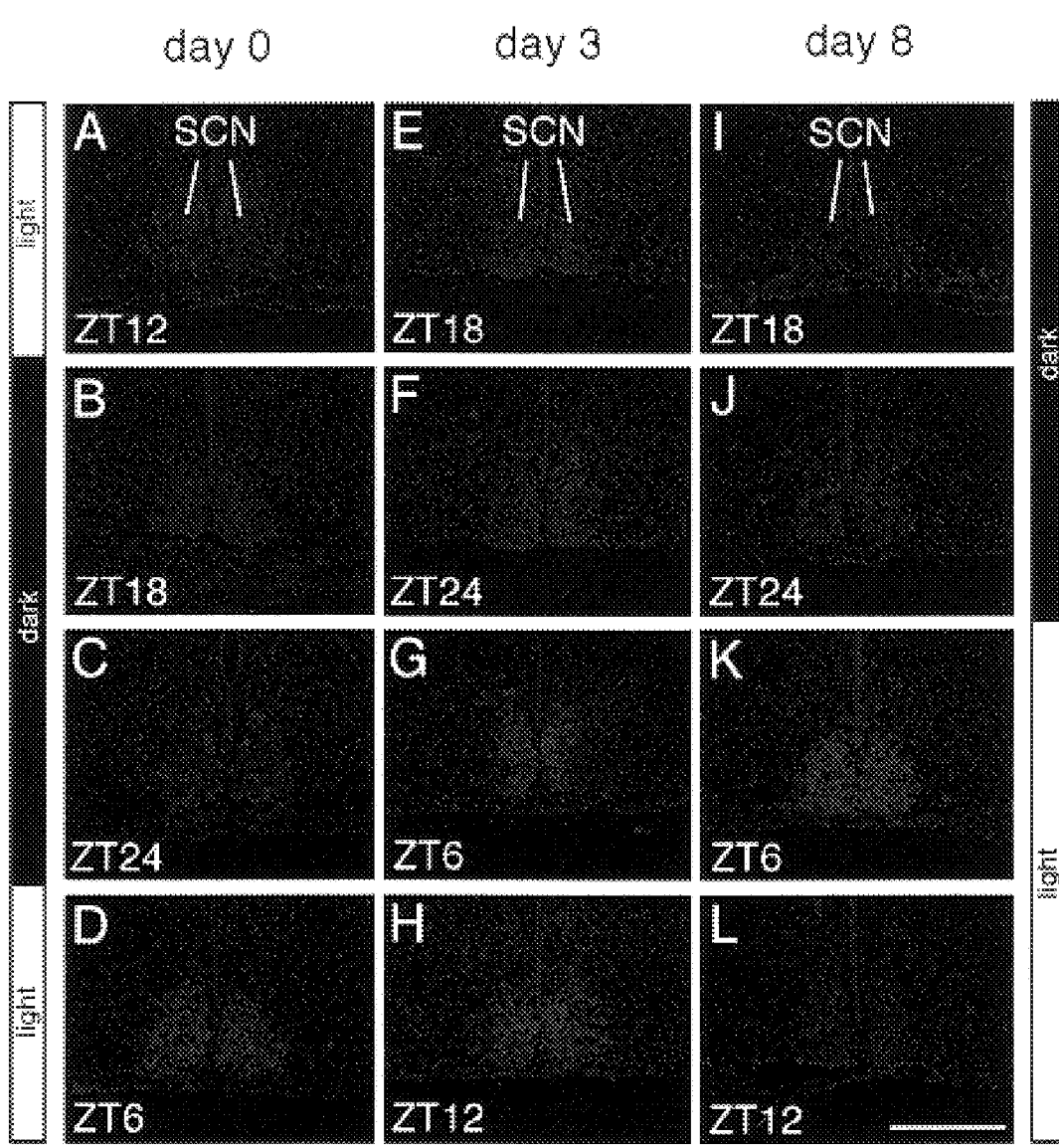
FIGS. 7A–7L show the entrainment in the suprachiasmatic nucleus of m-rigui expression by a forward shift of the 12 hours light/12 hours dark cycle by 6 hours. Data are from C57BL/6 males.

Circadian pace/makers are eventually reset under the influence of a changing light source. To test whether m-rigui expression responds to such a change, C57BL/6 mice were transferred to a 12 hours light/12 hours dark cycle which had been advanced by 6 hours. Animals were analyzed at the day of transfer to the new cycle, and 3 and 8 days thereafter. In each case animals were sacrificed at four 6 hour time intervals. Expression analysis was focussed on the suprachiasmatic nucleus (FIG. 7). A shift of maximal expression is clearly seen. At day 0, expression peaks at ZT6 (FIG. 7D). At day 3 expression is about equal at ZT6 and ZT12 (FIGS. 7G and 7H). By day 8, the entrainment is complete and only ZT6 (FIG. 7K) shows high m-rigui expression. From these data one can conclude that over a period of approximately one week, the regulation of the m-rigui gene is responsive to the circadian rhythm of the environment.

Discussion

Putative mammalian circadian regulator molecules should have the following characteristics. First, their expression should oscillate with a 24 hour rhythm. Second, they must be expressed in the suprachiasmatic nucleus, the master regulator of mammalian circadian rhythms. Third, circadian expression must persist in the absence of environmental cues such as light. Fourth, the intrinsic rhythm of expression should be reset by changes in the oscillation of environmental cues (entrainment). As judged from temporal mRNA expression studies, m-rigui fulfills these criteria.

During a 24 hour period, the level of expression of this gene in the suprachiasmatic nucleus goes through a distinct maximum and minimum. Maximum expression of mouse rigui in the superchiasmatic nucleus occurs at ZT6 whichs suggests that this gene behaves like a "day-type" oscillator (Dunlap, 1996). Moreover, when animals were transferred to constant darkness, such oscillation persists in the suprachiasmatic nucleus for at least four days. Whether the peak of expression is slightly shifted during that period of time cannot be resolved using expression data based on in situ hybridization. If animals are exposed to a dark/light cycle that is advanced by 6 hours, then a shift in the peak expression time in the suprachiasmatic nucleus occurs gradually. Based on these data, one can conclude that the expression of m-rigui can be entrained by a light cue.

An additional piece of evidence suggesting that m-rigui and its human homolog are clock genes comes from the observation of marked amino acid sequence conservation between m-rigui and the *Drosophila melanogaster* gene period. Mutations in period cause abnormal circadian rhythms and its expression oscillates with a circadian rhythm (Konopka and Benzer, 1971, Hardin et al., 1990, Hall, 1996). Sequence analysis identified RIGUI and its mouse homolog as a member of the bHLH-PAS domain gene family which includes genes such as ARNT, SIM, AHR, NPAS1, NPAS2 and the recently identified circadian regulator Clock. When compared with other members of this family, the best alignment within the PAS domain is found between RIGUI and Period. However, sequence identity is relatively low, explaining the difficulty of finding a vertebrate per homolog by cross-species hybridization approaches (Takahashi, 1995).

Several studies using an anti-Period-antibody have suggested the existence of a mammalian Period ortholog (Hall, 1990, Siwicki et al., 1992). It remains to be determined, whether the antigen detected in these immunological analyses is encoded by RIGUI (note, a 14 amino acid long peptide used to generate the anti-Period-antibody had only 24% sequence identity with the corresponding region of mouse Rigui protein). It is important to emphasize that there are many small clusters of amino acid sequence conservation outside the PAS domain, that are conserved between RIGUI and Period. This supports the concept that RIGUI is a mammalian ortholog of Period. Of note, RIGUI but not Period contains a bHLH motif. Whether this discrepancy disqualifies RIGUI from being a Period ortholog remains to be determined by experiments in which these genes are functionally interchanged. Fluorescence in situ hybridization and genomic PCR mapping indicate the presence of a single RIGUI locus. The existence of other per-like genes, not detected by these methods is a possibility. (Nagase et al., 1997) have recently reported a protein sequence which is 40% identical to RIGUI. Taken together, these expression studies, in combination with the presence of Per-like motifs in RIGUI, raise the possibility that RIGUI is an essential regulator of the mammalian clock. It thus appears that an element of the circadian clock is conserved between insects and mammals.

In addition to the suprachiasmatic nucleus, m-rigui is expressed in the internal granular layer and the Purkinje cells of the cerebellum, the hippocampus, the cerebral cortex, the olfactory bulb, the pars tuberalis and the retina. No periodic expression of m-rigui in the internal granular layer, the cerebral cortex and the hippocampus was seen, but the other tissues show oscillatory m-rigui expression. Interestingly, the phases of these cycles are not synchronized to that of the suprachiasmatic nucleus and differ among themselves. The nature of this phenomenon is not clear, but it is possible that there is tissue-autonomous regulation of m-rigui expression. It is tempting to speculate that this reflects the cell-autonomous expression of circadian clocks previously observed in cell and organ cultures and in transplantation studies (Ralph et al., 1990, Welsh et al., 1995, Tosini and Menaker, 1996). The existence of multiple oscillators suggests that m-rigui expression is probably not controlled by a single upstream regulator and raises the possibility of autoregulation, perhaps in conjunction with other proteins such as Clock.

What could be the significance of the oscillation of m-rigui expression in the pars tuberalis? This structure is a glandular epithelium surrounding the hypophysial stalk of the pituitary gland and is in direct contact with the portal blood supply. The pars tuberalis also releases luteinizing hormone which is negatively regulated, in part, by circulating melatonin (Nakazawa et al., 1991). The pars tuberalis has the highest concentration of melatonin receptors in the mammalian brain (de Reviers et al., 1989, Weaver and Reppert, 1990, Stankov et al., 1991, Fraschini and Stankov, 1993). These observations in conjunction with the oscillating expression of m-rigui, suggests that the pars tuberalis is a target site for a melatonin feedback loop and confers a circadian rhythm to the body via hormonal pathways.

Interestingly, expression of m-rigui in the pars tuberalis was observed in 129/SvEvBrd mice but not in the C57BL/6 strain. C57BL/6 and the majority of the inbred mice strains (exceptions are C3H/H and CBA) are known to have a genetic defect for pineal melatonin biosynthesis. Thus C57BL/6 mice do not produce melatonin (Goto et al., 1989). The 129/SvEvBrd strain carries C3H/H alleles as a result of historical backcrosses with that strain (Simpson et al., 1997), and thus it is therefore likely to generate melatonin. The strain-dependence of m-rigui expression in the pars tuberalis may reflect the difference in melatonin production. This would implicate melatonin as a regulator of m-rigui expression in this region of the brain.

The identification of RIGUI as a putative circadian clock gene provides a useful tool to explore the molecular mechanism of the mammalian circadian machinery. Using interaction screening approaches, it should be possible to find interacting proteins, perhaps in the form of a Drosophila Timeless ortholog. Furthermore, promoter analyses of the RIGUI gene should uncover how light cues and possibly other environmental stimuli, regulate the expression of this gene. Lastly, targeted disruption of the m-rigui gene using stem cell technology, may provide a valuable model system to study the various physiological and pathophysiological aspects of disrupting circadian rhythms.

The following references were cited herein:

Albrecht, U., Eichele, G., Helms, J. A., and, and Lu, H. (1997). Visualization of gene expression patterns by in situ hybridization. In Molecular and Cellular Methods in Developmental Toxicology, G. P. Daston, ed. (Boca Raton: CRC Press, Inc.), pp. 23–48.

Arendt, J., and Broadway, J. (1987). Light and melatonin as Zeitgebers in man. Chronobiol. Int. 4, 273–282.

Aronin, N., Sagar, S. M., Sharp, F. R., and Schwartz, W. J. (1990). Light regulates expression of a fos-related protein in rat suprachiasmatic nuclei. Proc. Natl. Acad. Sci. USA 87, 5959–5962.

Aschoff, J. (1969). Desynchronization and resynchronization of human circadian rhythms. Aerosp. Med. 40, 844–849.

Bargiellow, et al., Nature, 312:752–754 (1984).

Chirgwin, J. M., Przybyla, A. E., MacDonald, R. J., and Rutter, W. J. (1979). Isolation of biologically active ribonucleic acid from sources enriched in ribonuclease. Biochemistry 18, 5294–5299.

Citri, Y., Colot, H. V., Jacquier, A. C., Yu, Q., Hall, J. C., Baltimore, D., and Rosbash, M. (1987). A family of unusually spliced biologically active transcripts encoded by a Drosophila clock gene. Nature 326, 42–47.

de Reviers, M., Ravault, J. P., Tillet, Y., and Pelletier, J. (1989). Melatonin binding sites in the sheep pars tuberalis. Neurosci. Lett. 100, 89–93.

Dunlap, J. C. (1993). Genetic analysis of circadian clocks. Annu. Rev. Physiol. 55, 683–728.

Dunlap, J. C. (1994), Genetic and molecular analysis of circadian rhythms. Ann. Rev. Genet., 30:579–601 (1996).

Fraschini, F., and Stankov, B. (1993). Distribution of the melatonin receptor in the central nervous system of the vertebrates. Kinetic parameters and signal transduction pathways. In Light and Biological rhythms in man, L. Wetterberg, ed. (New York: Pergamon Press), pp. 121–131.

Goto, M., Oshima, I., Tomita, T., and Ebihara, S. (1989). Melatonin content of the pineal gland in different mouse strains. J. Pineal Res. 7, 195–204.

Hall, J. C. (1996). Are cycling gene products as internal zeitgebers no longer the zeitgeist of chronobiology. Neuron 17, 799–802.

Hall, J. C. (1990). Genetics of circadian rhythms. Annu. Rev. Genet. 24, 659–597.

Hardin, P. E., Hall, J. C., and Rosbash, M. (1990). Feedback of the Drosophila period gene product on circadian cycling of its messenger RNA levels. Nature 343, 536–540.

Ijdo, J. W., Lindsay, E. A., Wells, R. A., and Baldini, A. (1992). Multiple variants in subtelomeric region of normal karyotypes. Genomics 14, 1019–1025.

Kallioniemi, O. P., Kallioniemi, A., Mascio, L., Sudar, D., Pinkel, D., Deaven, L., and Gray, J. (1994). Physical mapping of chromosome 17 cosmids by fluoresence in situ hybridization and digital image analysis. Genomics 20, 125–128.

King, D. P., Zhao, Y., Sangoram, A. M., Wilsbacher, L. D., Tanaka, M., Antoch, M. P., Steeves, T. D. L., Vitaterna, M. H., Kornhauser, J. M., Lowery, P. L., Turek, F. W., and Takahashi, J. S. (1997). Positional cloning of the mouse circadian Clock gene. Cell 89, 641–653.

Konopka, R. J., and Benzer, S. (1971). Clock mutants of *Drosophila melanogaster*. Proc. Nat. Acad. Sci. USA 68, 2112–2116.

Kornhauser, J. M., Nelson, D. E., Mayo, K. E., and Takahashi, J. S. (1992). Regulation of jun-B messanger RNA and AP-1 activity by light and a circadian clock. Science 255, 1581–1584.

Kraft, M., and Martin, R. J. (1995). Chronobiology and chronotherapy in medicine. Dis. Mon. 41, 501–575.

Lee, C. C., Yazdani, A., Wehnert, M., Zhao, Z., Lindsay, E. A., Bailey, J., Coolbaugh, M., Couch, L., Xiong, M., Chinault, A. C., Baldini, A., and Caskey, C. T. (1995). Isolation of chromosome specific genes by reciprocal probing of arrayed cDNA and cosmid libraries. Hum. Mol. Genet. 4, 1373–1380.

Nagase, T., Ishikawa, K., Nakajima, D., Ohira, M., Seki, N., Miyajima, N., Tanaka, A., Kotani, H., Nomura, N., and Ohara, O. (1997). Prediction of the coding sequences of unidentified human genes. VII. The complete sequences of 100 new cDNA clones from brain which can code for large proteins in vitro. DNA Res 4, 141–150.

Nakazawa, K., Marubayashi, U., and McCann, S. M. (1991). Mediation of the short-loop negative feedback of luteinizing hormone (LH) on LH-releasing hormone release by melatonin-induced inhibition of LH release from the pars tuberalis. Proc. Natl. Acad. Sci. USA 88, 7576–7579.

Pittendrigh, C. S. (1993). Temporal organization: reflections of a Darwinian clock-watcher. Annu. Rev. Physiol. 55, 16–54.

Raju, U., Koumenis, C., Nunez-Regueiro, M., and Eskin, A. (1991). Alteration of the phase and period of a circadian oscillator by reversible transcription inhibitor. Science 253, 673–675.

Ralph, M. R., Foster, R. G., Davis, F. C., and Menaker, M. (1990). Transplanted suprachiasmatic nucleus determines circadian period. Science 247, 975–978.

Reppert, S. M., and Sauman, I. (1995). period and timeless tango: a dance of two clock genes. Neuron 15, 983–986.

Sambrook, J., Fritsch, E. F., and Maniatis, T. (1989). Molecular Cloning. A Laboratory Manual., C. S. H. Laboratory, ed. (Cold Spring Harbor, N.Y.

Schwartz, W. J., and Gainer, H. (1977). Suprachiasmatic nucleus: use of 14C-labeled deoxyglucose uptake as a funtional marker. Science 197, 1089–1091.

Sehgal, A., Price, J. L., Man, B., and Young, M. W. (1994). Loss of circadian behavioral rhythms and per RNA oscillations in the Drosophila mutant timeless. Science 263, 1603–1609.

Simpson, E. M., Linder, C. C., Sargent, E. E., Davisson, M. T., Morbraaten, L. E., and Sharp, J. J. (1997). Genetic variation among 129 substrains and its importance for targeted mutagenesis in mice. Nature Genet. 16, 19–27.

Siwicki, K. K., Schwartz, W. J., and Hall, J. C. (1992). An antibody to the Drosophila period protein labels antigens in the suprachiasmatic nucleus of the rat. J. Neurogenetics 8, 33–42.

Smith, R. F., and Smith, T. F. (1992). Pattern-induced multi-alignment (PIMA) algorythm employing secondary structure-dependent gap penalties for comparative protein modelling. Prot. Engineering 5, 35–41.

Stankov, B., Cozzi, B., Lucini, V., Fumagalli, P., Scaglione, F., and Fraschini, F. (1991). Characterization and mapping of melatonin receptors in the brain of three mammlian species: rabbit, horse, and sheep. Neuroendocrinology 53, 214–221.

Sun, Z. S., Bailey, J., and and Lee, C. C. (1996). Isolation and mapping of five full-length genes on chromosome 17. Am. J. Hum. Genet. 59, A160.

Swaab, D. F., Van Someren, E. J. W., Zhou, J. N., and and Hofman, M. A. (1996). Biological rhythms in the human life cycle and their relationship to functional changes in the suprachaismatic nucleus. In Hypothalamic Integration of Circadian Rhythms, R. M. Buijs, A. Kalsbeek, H. J. Romijn, C. M. A. Pennartz and M. and Mirmiran, eds. (AmsterdamlLuasanne-New York-Oxford-Shannon-Tokyo: ELSEVIER), pp. 349–368.

Takahashi, J. S. (1995). Molecular neurobiology and genetics of circadian rhythms in mammals. In Ann. Rev. Neurosci., pp. 531–553.

Takahashi, J. S., and and Turek, F. W. (1987). Anisomycin, an inhibitor of protein synthesis, perturbs the phase of a mammalian circadian pacemaker. Brain Res 405, 199–203.

Teicher, M. H., Glod, C. A., Magnus, E., Harper, D., Benson, G., Krueger, K., and and McGreenery, C. E. (1997). Circadian rest activity disturbances in seasonal affective disorder. Archives of General Psychiatry 54, 124–130.

Tosini, G., and Menaker, M. (1996). Circadian rhythms in cultured mammalian retina. Science 272, 419–421.

Vignau, J., Dahlitz, J., Arendt, J., English, J., and and Parkes, J. D. (1993). Biological rhythms and sleep orders in man: The delay sleep phase syndrome. In Light and Biological Rhythms in Man, L. Wetterberg, ed. (Oxford-New York-Seoul-Tokyo: Pergamon Press), pp. 261–274.

Weaver, D. R., and Reppert, S. M. (1990). Melatonin receptors are present in the ferret pars tuberalis and pars distalis, but not in brain. Endocrinology 127, 2607–2609.

Wehr, T. A. (1996). A "clock for all seasons" in the human brain. In Hypothalamic Integration of Circadian Rhythms, R. M. Buijs, A. Kalsbeek, H. J. Romijn, C. M. A. Pennartz and M. and Mirmiran, eds. (AmsterdamlLuasanne-New York-Oxford-Shannon-Tokyo: ELSEVIER), pp. 321–342.

Welsh, D. K., Logothetis, D. E., Meister, M., and Reppert, S. M. (1995). Individual neurons dissociated from rat suprachiasmatic nucleus express independently phased firing rhythms. Neuron 14, 697–706.

Zeng, H., Qian, Z., Myers, M. P., and Rosbash, M. (1996). A light-entrainment mechanism for the Drosophila circadian clock. Nature 380, 129–135.

Zhou, et al., (1997). Molecular characterization of two mammalian bHTH-PAS domain proteins selectively expressed in the central nervous system. Proc. Natl. Acad. Sci. USA 94, 713–718.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. Isolated and purified rigui1 protein, wherein said rigui1 protein has an amino acid sequence selected from the group consisting of SEQ ID No. 6, SEQ ID No. 7, SEQ ID No. 8, and SEQ ID No. 10.

2. Isolated DNA encoding a rigui1 protein, wherein said rigui1 protein has an amino acid sequence selected from the group consisting of SEQ ID No. 6, SEQ ID No. 7, SEQ ID No. 8, and SEQ ID No. 10.

3. The DNA of claim 2, wherein said DNA is human DNA.

4. The DNA of claim 3, wherein said DNA has the sequence shown in SEQ ID No. 3.

5. The DNA of claim 3, wherein said DNA encodes a protein having the sequence shown in SEQ ID No. 7.

6. The DNA of claim 3, wherein said DNA has the sequence shown in SEQ ID No. 4.

7. The DNA of claim 6, wherein said DNA encodes a protein having the sequence shown in SEQ ID No. 6.

8. The DNA of claim 3, wherein said DNA has the sequence shown in SEQ ID No. 5.

9. The DNA of claim 8, wherein said DNA encodes a protein having the sequence shown in SEQ ID No. 8.

10. The DNA of claim 2, wherein said DNA is mouse DNA.

11. The DNA of claim 10, wherein said DNA has the sequence shown in SEQ ID No. 9.

12. The DNA of claim 10, wherein said DNA encodes a protein having the sequence shown in SEQ ID No. 10.

13. A vector capable of expressing the DNA of claim 2 adapted for expression in a recombinant cell and regulatory elements necessary for expression of the DNA in the cell.

14. A host cell transfected with the vector of claim 13, said vector expressing a rigui1 protein.

15. The host cell of claim 14, wherein said cell is selected from group consisting of bacterial cells, mammalian cells, plant cells and insect cells.

16. An isolated DNA encoding a protein having rigui1 activity, wherein said DNA hybridizes to isolated DNA comprising the nucleotide sequence depicted SEQ ID NO: 3, SEQ ID NO: 4, SEQ ID NO: 5, or SEQ ID NO:9, wherein said hybridization conditions consist of hybridization in 5× SSC, 1% SDS at 65° C. followed by washing at 65° C. with SSC ranging in concentration from 1× to 0.1× and containing 0.1% SDS.

17. A method of detecting expression of the DNA of claim 1, comprising the steps of:
   (a) contacting mRNA obtained from a cell with a labeled hybridization probe; and
   (b) detecting hybridization of the probe with the mRNA.

18. The method of claim 17, wherein said probe consists of a portion of the DNA of SEQ ID Nos. 3, 4, 5 and 9.

* * * * *

UNITED STATES PATENT AND TRADEMARK OFFICE
CERTIFICATE OF CORRECTION

PATENT NO. : 6,190,882 B1
DATED : February 20, 2001
INVENTOR(S) : Cheng-Chi Lee, Urs Albrecht, Gregor Eichele and Zhong Sheng Sun It is certified that error appears in the above-identified patent and that said Letters Patent is hereby corrected as shown below:

Column 3,
Line 25, "is" should read -- are --.
Line 41, please remove "adult of".
Line 64, please insert -- (SEQ ID NO: 13) -- after "(U77969)".

Column 4,
Line 29, "shows" should read -- show --.
Line 33, "shows" should read -- show --.

Column 5,
Line 40, "acid" should read -- acids --.
Line 48, "nomeclature" should read -- nomenclature --.

Column 7,
Line 15, "effects" should read -- effect --.

Column 10,
Line 26, please delete the closing parentheses after "10".
Line 32, please delete the closing parentheses after "9".

Column 11,
Line 1, please delete the closing parentheses after "9".

Column 14,
Line 9, please insert the word -- these -- between "include" and "consisting".
Line 11, "a" should read -- an --.
Line 37, please insert the word -- on -- between "out" and "the".

Column 15,
Line 15, please insert the word -- to -- between "according" and "the".

Column 19,
Lines 7-8, please insert the following line after the line beginning with "2501", -- 2551 GAAGGAAGAGCAAGCCTTCCTCAGCCGCTT CCGAGACCTG GGCAGGCTGC --
Line 8, "2551 GTGG" should read -- 2601 GTGG --.

Column 29,
Line 64, please insert the following line after the line beginning with "2051", -- 2101 GGAGAGCTGCAACCTCCCCA GCACCACTAA GCGTAAATGT GCCTCCTCCT --.

UNITED STATES PATENT AND TRADEMARK OFFICE
CERTIFICATE OF CORRECTION

PATENT NO.   : 6,190,882 B1
DATED        : February 20, 2001
INVENTOR(S)  : Cheng-Chi Lee, Urs Albrecht, Gregor Eichele and Zhong Sheng Sun It is certified that error appears in the above-identified patent and that said Letters Patent is hereby corrected as shown below:

Column 33,
Lines 47-48, please insert the following line after the line beginning with "651", -- 701 GTLSPLALAN KAESVVSVTS QCSFSSTIVH VGDKKPPESD IIMMEDLPGL --.
Line 48, "701 APG" should read -- 751 APG --.
Line 58, "i.e." should read -- (i.e. --.

Column 41,
Line 60, "hour" should read -- hours --.

Column 44,
Line 4, "whichs" should read -- which --.

Column 45,
Line 52, please remove the first "and,".

Column 46,
Line 29, "659" should read -- 559 --.
Line 52, "messanger" should read -- messenger --.

Column 47,
Line 52, please delete the first "and".

Signed and Sealed this

Sixth Day of August, 2002

Attest:

JAMES E. ROGAN
Director of the United States Patent and Trademark Office

Attesting Officer